(12) United States Patent
Dietz et al.

(10) Patent No.: US 10,239,906 B2
(45) Date of Patent: Mar. 26, 2019

(54) APPARATUS AND METHOD FOR OBTAINING GLYCOGLYCEROLIPIDS AND GLYCOSPHINGOLIPIDS FROM LIPID PHASES

(71) Applicants: Nanoscience for life GmbH & CoKG, Wiesbaden (DE); GEA Westfalia Separator Group GmbH, Oelde (DE)

(72) Inventors: Ulrich Dietz, Wiesbaden (DE); Steffen Hruschka, Oelde (DE)

(73) Assignees: Nanoscience for Life GmbH & CoKG, Wiesbaden (DE); GEA Westfalia Separator Group GmbH, Oelde (DE)

( * ) Notice: Subject to any disclaimer, the term of this patent is extended or adjusted under 35 U.S.C. 154(b) by 1 day.

(21) Appl. No.: 15/316,123

(22) PCT Filed: Jun. 3, 2015

(86) PCT No.: PCT/EP2015/062465
§ 371 (c)(1),
(2) Date: Dec. 2, 2016

(87) PCT Pub. No.: WO2015/185675
PCT Pub. Date: Dec. 10, 2015

(65) Prior Publication Data
US 2017/0121360 A1    May 4, 2017

(30) Foreign Application Priority Data
Jun. 4, 2014 (DE) .................. 10 2014 210 662

(51) Int. Cl.
| C07H 15/04 | (2006.01) |
| C11B 1/10 | (2006.01) |
| C07H 1/06 | (2006.01) |
| C11B 1/02 | (2006.01) |

(52) U.S. Cl.
CPC ............. *C07H 1/06* (2013.01); *C07H 15/04* (2013.01); *C11B 1/025* (2013.01); *C11B 1/10* (2013.01)

(58) Field of Classification Search
None
See application file for complete search history.

(56) References Cited

U.S. PATENT DOCUMENTS

| 3,102,898 A * | 9/1963 | Schmitt .................. C11B 3/001 554/203 |
| 3,943,155 A | 3/1976 | Young |
| 4,112,129 A | 9/1978 | Duensing et al. |
| 4,160,774 A | 7/1979 | Shenoy et al. |
| 4,256,578 A | 3/1981 | Kozar |
| 4,806,269 A | 2/1989 | Shimizu |
| 4,808,426 A * | 2/1989 | Strop .................. C11B 1/00 426/417 |
| 5,962,056 A * | 10/1999 | Melin ..................... C11B 3/001 426/330.6 |
| 5,972,928 A | 10/1999 | Chatterjee |
| 6,111,120 A | 8/2000 | Myers |
| 6,291,579 B1 | 9/2001 | Kalck et al. |
| 6,953,849 B2 | 10/2005 | Vali et al. |
| 7,635,398 B2 | 12/2009 | Bertram |
| 8,647,396 B2 | 2/2014 | Boensch et al. |
| 9,434,755 B2 | 9/2016 | Schilling et al. |
| 2013/0090488 A1 * | 4/2013 | Dietz ..................... C07B 63/04 554/185 |

FOREIGN PATENT DOCUMENTS

| EP | 0730033 A2 | 9/1996 |
| EP | 0831712 B1 | 12/2002 |
| EP | 2389816 A1 | 11/2011 |
| EP | 2592133 A1 * | 5/2013 ............ C11B 3/001 |
| JP | 2002-294274 A | 10/2002 |
| WO | WO 1983003776 A1 | 11/1983 |
| WO | WO 1994021765 A1 | 9/1994 |
| WO | WO 1998001464 A1 | 1/1998 |
| WO | WO 1999064545 A2 | 12/1999 |
| WO | WO 2000068347 A1 | 11/2000 |
| WO | WO 2007/069733 A1 | 6/2007 |
| WO | WO 2015181399 A1 | 12/2015 |

OTHER PUBLICATIONS

CN103396884N, machine translation, Nov. 20, 2013.*
Fanny Adam et al., "Solvent-free ultrasound-assisted extraction of lipids from fresh microalgae cells: A green, clean and scalable process," Bioresource Technology, Elsevier BV, GB, Feb. 18, 2012, vol. 114, pp. 457-465.
International Search Report received in corresponding PCT Application No. PCT/EP2015/062465 dated Aug. 12, 2015 in 4 pages.

* cited by examiner

Primary Examiner — Layla D Berry
(74) Attorney, Agent, or Firm — Knobbe Martens Olson & Bear, LLP

(57) ABSTRACT

The present invention relates to an apparatus and method for separating glycoglycerolipids and also glycoglycerolipids and glycosphingolipids from a lipid phase that contains glycoglycerolipids and acyl glycerides or glycoglycerolipids and glycosphingolipids and acyl glycerides, in mild conditions with no hydrolysis and while at the same time effectively depleting the lipid phase of said glycoglycerolipids, glycoglycerolipids and glycosphingolipids and their accompanying substances using an aqueous extraction process.

15 Claims, 3 Drawing Sheets

APPARATUS AND METHOD FOR OBTAINING GLYCOGLYCEROLIPIDS AND GLYCOSPHINGOLIPIDS FROM LIPID PHASES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field of the Invention

The present invention relates to a device for separating glycoglycerolipids and glycoglycerolipids and glycosphingolipids from a lipid phase containing glycoglycerolipids and acylglycerides, or glycoglycerolipids and glycosphingolipids and acylglycerides, and is also directed to methods for separating glycoglycerolipids and glycoglycerolipids and glycosphingolipids from a lipid phase.

Description of the Related Art

Glycolipids, glycoglycerolipids, glycosphingolipids and phospholipids are biogenic lipids that occur as membrane components in almost all biological systems and, as such they exhibit amphiphilic properties, i.e. a hydrophilic head group and a hydrophobic or lipid tail group. The ubiquitous presence of glycolipids, glycoglycerolipids, glycosphingolipids, and phospholipids in virtually all living things also explains that lipid extracts (for example, vegetable oils or animal oils) thereof inevitably also contain glycolipids, and phospholipids.

Their amphiphilic properties give the glycoglycerolipids and glycosphingolipids a special importance in the solubilization of hydrophilic molecules in lipid phases such as oils.

Glycolipids, glycoglycerolipids, glycosphingolipids, and glycophospholipids are excellent biological emulsifiers with a high emulsion performance due to their amphiphilic properties. But this also explains why such lipids cannot be separated or only to a small extent with standard aqueous extraction methods. On the other hand, glycoglycerolipids and glycosphingolipids have an enormous economic potential due to their suitability as biological emulsifiers or biological surfactants. In practical applications, this relates in particular to the use as a cleaning agent for removal of oily or greasy residues. However, glycoglycerolipids and glycosphingolipids are also suitable for the emulsification of lipophilic active substances, e.g. for pharmaceutical formulations or pesticides, because they improve the absorption of these active substances by the target organism. In addition, evidence exists about immunomodulatory effects of various glycoglycerolipids and glycosphingolipids, which are also part of human cell membranes. Further, some glycoglycerolipids and glycosphingolipids are also attributed to have antibacterial and fungicidal properties. The emulsifying properties of the glycoglycerolipids and glycosphingolipids also cause superior interaction of lipophilic and hydrophilic components in baked goods.

On the other hand, glycoglycerolipids and glycosphingolipids have an enormous economic potential due to the fact that they are a bio-emulsifier. In practical application, this relates in particular to the use as a cleaning agent for removal of oily or greasy residues.

Consequently, the production of glycoglycerolipids and glycosphingolipids from biogenic lipid fractions or oils is of economic interest because they have a wide variety of uses in the food industry and especially in pastries and sweets.

Although it can be assumed that glycoglycerolipids and glycosphingolipids of various types are present in virtually all lipid phases which can be obtained from biogenic materials, few studies for this exist in the scientific literature. In particular, the compositions of such lipid phases, as well as the effects of these compounds on the solubilizing of other compounds also solubilized herein, are substantially unclear.

Glycoglycerolipids and glycosphingolipids have a strong affinity for lipid fractions despite their amphiphilic character due to their long fatty acid residues. Therefore, the distribution in aqueous extraction media from the prior art is only minor. However, liquid extractions were successfully accomplished with mixtures of organic solvents. By doing so, the use of alcohols is crucial in order to achieve a high separation efficiency. On a laboratory scale, the separation of glycoglycerolipids and glycosphingolipids is achieved by chromatography followed by solvent extraction of the adsorbed glycolipids. However, such adsorptive methods are not suitable on the industrial scale for economic and ecological reasons. U.S. Pat. No. 6,953,849 describes the extraction of glycolipids from rice bran oil by means of hot water steam. This cleaves the sugar residues, which means that parts of these compounds can be lightly separated by the steam extraction. In such a treatment of edible oils, a disadvantage is e.g. that at the steam temperatures applied herein and the duration of this steam exposure, an increased proportion of trans-fatty acids can occur in the edible oils, whereby such produced edible oils can become harmful. Furthermore, enzymatic methods for the removal of glycoglycerolipids and glycosphingolipids from lipid phases are known in the prior art. However, the glycoglycerolipids and glycosphingolipids are thereby modified in their structure, which severely restricts the later use of the separated glycolipid fraction or renders them unusable for further applications. Consequently, no process exists so far which permits a continuous and gentle recovery of larger amounts of biogenic glycoglycerolipids and glycosphingolipids.

In lipid phases which must undergo a fining process in order to be freed from accompanying substances, separation of the glycoglycerolipids and glycosphingolipids per se is not necessary since in principle they do not lead to a relevant quality restriction (color, odor, transparency) of the refined product, if they are present in only small amounts. However, problems can arise by their strong binding capacity to water, alkaline earth metal ions and metal ions whose presence in a refined lipoid phase, for example in a vegetable oil is not desired. Also, depletion with conventional techniques of the above mentioned compounds is problematic from a lipoid phase that is heavily contaminated with glycoglycerolipids and glycosphingolipids.

According to the prior art, for the purpose of technical refining, lipid phases are usually subjected to a so-called degumming process in order to convert hydratable compounds into a water phase or to effect aggregation via saponification of fatty acids, whereby the dissolved or aggregated compounds are obtained by processes of phase separation. By these methods, most of the hydratable and some nonhydratable phospholipids are separated off. Glycoglycerolipids and glycosphingolipids are partially degraded by hydrolysis and removed with the phospholipid fraction. In case of lipid phases which have been purified by standard degumming methods, an intensive mixing procedure of the lipid phase with a water phase can effect depending on the content of glycolipid compounds an emulsion that allows a subsequent phase separation by means of centrifugal force only partially or not at all. It could be shown that a further purification step under normal conditions (room temperature and normal pressure) either with an alkali solution or an acid (citric or phosphoric acid) is not sufficient also after an intensive mixing process for the removal of relevant amounts of glycoglycerolipids and glycosphingolipids, when subsequently a repeated separation by a separator is performed.

From the known properties of the glycoglycerolipids and glycosphingolipids, however, it can be assumed that water may bind to the OH groups of the sugar residues. Further, it can be assumed that glycoglycerolipids and glycosphingolipids adhere small amounts of water without formation of micelles. Alkaline earth metal and metal ions are bound by the same mechanism. It can be assumed that glycoglycerolipids and glycosphingolipids having multiple and complex sugar moieties are able to bind larger amounts of water and metal ions. Further it can be assumed that also glycoglycerolipids and glycosphingolipids tend to form micelles in lipoid phases. If water and metal ions are bound to sugar residues, the elimination of these substances by an aqueous medium is largely prevented by the fact that long nonpolar fatty acid residues strongly hinder the penetration of water into these structures and prevent a "rinsing out" of those compounds from the sugar residues to which they are electrostatically bound. This explains why, according to the prior art, it has hitherto been necessary to remove the fraction of the glycoglycerolipids and glycosphingolipids by means of chemical or enzymatic hydrolysis or distillative processes, whereby the content of water, as well as alkaline earth metal ions and metal ions still bound in a lipoid phase can be reduced to the required degree. Therefore, it is all the more surprising that the strongly hydrophilic salt compounds having a water shell in their inventive use form that causes hydrophilisation of glycoglycerolipids and glycosphingolipids, which allows their separation into an aqueous phase. Moreover, it was unexpected and surprising that the separated galactosydiglycerides have a high affinity for the starting lipid medium due to their hydrophilic-lipophilic balance. It is therefore highly probable that, by the introduction of the water-dissolved salts according to the invention and the water entry effected therewith, a combination of glycoglycerolipids and glycosphingolipids as micellar structures is made possible, whereby these can be separated by means of gravitational separation from a lipoid phase. This, however, does not fully explain the unexpectedly significant increase in the extraction efficiency of the process according to the invention when an intensive mixing of the aqueous media according to the invention is used.

Glycoglycerolipids and glycosphingolipids obtained from lipoid phases by extractive processes usually have very different structures and compositions. Often, they are associated with other structures via hydrophobic or hydrophilic interactions, for which they have served as "solubilizers" in the lipoid phase. This could explain why parts of the glycolipid fraction can be dissolved from structures to which they are electrostatically bound, or the glycoglycerolipids and glycosphingolipids are released together with the electrostatically bound structures only by organic solvents. This could also explain the large number of unknown compounds found in some glycolipid-rich extraction phases according to the invention, which have not been elucidated so far. One of these nonglycolipid compounds which are separated by the process according to the invention is e.g. phorbol ester.

From the above-mentioned aspects, it is all the more astonishing that it is possible to remove the glycolipid fractions contained in the lipoid phases by the intensive mixing procedure of the salt solutions according to the invention with a single aqueous extraction step or in lipoid phases having a very high content of glycoglycerolipids and glycosphingolipids, it is possible to remove these with fewer extraction steps than in the case with a low-energy input for the mixing process of the aqueous solutions into the lipoid phases. As a further unexpected and particularly advantageous effect of the removal of the glycolipid fraction is that thereby the binding capacity for water and electrolytes in the thus treated lipoid phase is reduced. Furthermore, there is virtually no foam formation in the case of subsequent separation of the lipoid phases with aqueous media. Surprisingly, it has also been found that aqueous solutions of guanidine or amidino compounds which are mixed with an intensive mixing procedure with a lipoid phase treated according to the invention, can be separated from the oil phase more readily by means of centrifugal separation, when this is done subsequent to the inventive separation of glycoglycerolipids and glycosphingolipids by an intensive mixing procedure of the salt solutions.

In the prior art, the separation of lipids from oils by means of a sodium chloride solution is disclosed, for example in WO 2012/109642 A1. Notwithstanding the undesirable corrosive properties of chloride salts such as sodium chloride which attacks and corrodes the processing devices, the inventors could demonstrate that only a specific selection of anions, as disclosed herein, can be used for the separation of glycoglycerolipids and glycosphingolipids according to the invention, and anions such as, for example chloride, bromide, iodide, nitrate, nitrite, sulfate, phosphate, and many others are not capable of solving the objective according to the invention.

EP 2 735 605 A1 describes the separation of rhamnolipids by extraction using an organic solvent. In this process, the rhamnolipids are transferred from an aqueous phase into an organic phase and are not separated from a lipoid phase. Moreover, no salts are used in the separation.

It is therefore the objective of the present invention to provide a device and a method for separating glycoglycerolipids or glycoglycerolipids and glycosphingolipids from a lipoid phase which comprises, inter alia, glycoglycerolipids and acylglycerides or glycoglycerolipids and glycosphingolipids and acylglycerides.

This objective is achieved according to the invention by the technical teaching of the independent claims. Further advantageous embodiments of the invention result from the dependent claims, the description, the figures, and the examples.

DESCRIPTION OF THE PREFERRED EMBODIMENT

Surprisingly, it has now been found that it is possible to bind and transfer glycoglycerolipids into an aqueous phase by aqueous solutions containing at least one salt which is readily soluble in water at 20° C. and which, when dissociated in water, forms carbonate ($CO_3^{2-}$), bicarbonate ($HCO_3^-$), metasilicate ($SiO_3^{2-}$), orthosilicate ($SiO_4^{4-}$), disilicate ($Si_2O_5^{2-}$), trisilicate ($Si_3O_7^{2-}$), acetate ($CH_3COO^-$), borate ($BO_3^{3-}$), or tartrate ($C_4H_4O_6^{2-}$) ions, when contacting a lipoid phase with the aqueous phase by performing an intensive mixing process, while maintaining their chemical and structural integrity.

"Readily water-soluble" in this context preferably means a solubility of at least 30 g/l in water at 20° C. The introduction of an aqueous solution with the abovementioned compounds, which is necessary for the separation of glycoglycerolipids and glycosphingolipids, can already be carried out by means of a stirrer. It was found that, as a function of the stirring time, without or with only slightly heating of the suspension or emulsion, spontaneous phase separation occurs, whereby turbid substances are dissolved in the water phase.

While after the separation of such a treated lipid phase, there was virtually no further separation of turbid substances by a renewed agitated introduction of an aqueous solution with the above-mentioned compounds, surprisingly, a significant separation of turbid substances in the water phase could be effected by intensive mixing of such a pretreated lipid phase with a solution of the above-mentioned compounds. In case of a repetition of an intensive agitated introduction of a solution with the above-mentioned compounds into the lipid phase that has been pretreated by an intensive mixing process with the respective aqueous solutions, practically no non-triglycerides could be separated off. There was no or very little emulsion formation of the lipid phases when the pretreated lipid phase was mixed again with water. Thus, it was shown for the first time that significant amounts of remaining glycoglycerolipids and glycosphingolipids are dissolved and can be separated off using centrifugal methods by an intensive agitated introduction of an aqueous solution of the above-mentioned compounds into lipid phases, in which a substantial removal of hydratable phospholipids and free fatty acids has already taken place.

Moreover, it was quite unexpected that in case of glycoglycerolipid-containing aqueous fractions obtained by an intensive mixing with salts which have a solubility of preferably at least 30 g/l in water at 20° C., and when dissociated in water form carbonate ($CO_3^{2-}$), bicarbonate ($HCO_3^-$), metasilicate ($SiO_3^{2-}$), orthosilicate ($SiO_4^{4-}$), disilicate ($Si_2O_5^{2-}$), trisilicate ($Si_3O_7^{2-}$), acetate ($CH_3COO^-$), borate ($BO_3^{3-}$) or tartrate ($C_4H_4O_6^{2-}$) ions, a relevant co-separation of triacylglycerides does not occur, as revealed by thin-layer chromatographic analyses. This is all the more surprising as that it is possible to produce a stable non-oily emulsion with the so separated glycoglycerolipid-containing fraction, which has a very high emulsifying capacity for the purified triglyceride phase. Thus, for the first time, an aqueous separation process can be provided by which a nearly complete separation of non-hydrolyzed glycoglycerolipids from lipid phases can be achieved.

The inventive contacting of the aqueous phases with the dissolved salts performed with an intensive introduction resulted in separation of the glycoglycerolipids which are electrostatically bound to other structures; however, this can also be achieved by a low mixing introduction but which is performed at elevated temperatures of the lipid phase. This leads, however, to a rapid hydrolytic degradation of the glycoglycerolipids which is not desired for the recovery and utilization of this fraction. By using the intensive introduction of the dissolved salts according to the invention, it is possible to dissolve out substantially all of the glycoglycerolipids being in a lipid phase without requiring an increase in the temperature of the lipid phase. This allows the production of structurally unaltered glycoglycerolipids.

Since, according to the technical teaching of this invention, long contact times of the glycoglycerolipids to be separated with the aqueous media favor hydrolysis and thereby higher process costs are to be expected, a particularly preferred embodiment for contacting the aqueous and lipoid phase is the application of an intensive mixer which is able to perform an intensive mixing within a short time. It can also be deduced from the technical teaching that, in the context of such an intensive mixture, air or gases (for example by demixing processes) can be introduced, which then lead to formation of a very stable emulsion which largely hinders the separation of the glycoglycerolipids and glycosphingolipids since phase separation of an air/gas-containing emulsion by centrifugation is not possible. It can be assumed that glycoglycerolipids themselves contribute to the formation of stable interfaces between a gas phase and a liquid phase since formation of such emulsions cannot be observed or can only be observed to a small extent after separation of the glycolipid fraction. The invention is also directed to the use of a separation device that allows one to take advantage of the beneficial effects of the intensive mixing process of the aqueous salt solutions according to the invention with a lipid phase containing glycoglycerolipids and glycosphingolipids, namely obtaining a hydrolysis-free glycolipid mixture and conduction of an economical process sequence, by ensuring an exclusion of air entrapment or gas formation during the mixing and separation of the phases.

Therefore, it is particularly advantageous if the intensive mixing process of the aqueous solutions into a lipid phase according to the invention takes place under exclusion of an air/gas introduction.

Furthermore, it is particularly advantageous if a separator separates the mixtures according to the invention consisting of a lipid phase and an aqueous solution according to the invention from each other under exclusion of an air/gas introduction.

The present invention relates to a device for separating glycoglycerolipids from a lipid phase which contains glycoglycerolipids and acylglycerides, where the device comprising an intensive mixer for receiving the lipid phase, a cavity with an inlet to the intensive mixer for receiving an aqueous phase containing anions of at least one salt which has a solubility of at least 30 g/l in water at 20° C. and which, upon dissociation in water, forms carbonate ($CO_3^{2-}$), bicarbonate ($HCO_3^-$), metasilicate ($SiO_3^{2-}$), orthosilicate ($SiO_4^{4-}$), disilicate ($Si_2O_5^{2-}$), trisilicate ($Si_3O_7^{2-}$), acetate ($CH_3COO^-$), borate ($BO_3^{3-}$) and/or tartrate ($C_4H_4O_6^{2-}$), and a centrifuge with a feed line to the intensive mixer.

Of course, the aqueous phase also contains cations so that the present invention relates to a device for separating glycoglycerolipids from a lipid phase, which contains glycoglycerolipids and acylglycerides, wherein the device comprises an intensive mixer for receiving the lipid phase, a cavity having a feed line to the intensive mixer for receiving an aqueous phase containing cations and anions of at least one salt which has a solubility of at least 30 g/l in water at 20° C. and which, upon dissociation in water, forms carbonate ($CO_3^{2-}$), bicarbonate ($HCO_3^-$), metasilicate ($SiO_3^{2-}$), orthosilicate ($SiO_4^{4-}$), disilicate ($Si_2O_5^{2-}$), trisilicate ($Si_3O_7^{2-}$), acetate ($CH_3COO^-$), borate ($BO_3^{3-}$), and/or tartrate ($C_4H_4O_6^{2-}$) ions, and a centrifuge with a feed line to the intensive mixer.

If the lipid phase also contains glycosphingolipids in addition to the glycoglycerolipids, then these can be separated from the lipid phase together with the glycoglycerolipids without the need for any other device. In such a case, the present invention relates to a device for separating glycoglycerolipids and glycosphingolipids from a lipid phase which contains glycoglycerolipids, glycosphingolipids, and acylglycerides, wherein the device comprises an intensive mixer for receiving the lipid phase, a cavity with a feed line to the intensive mixer for receiving an aqueous phase containing anions of at least one salt which has a solubility of at least 30 g/l in water at 20° C. and which, upon dissociation in water, forms carbonate ($CO_3^{2-}$), bicarbonate ($HCO_3^-$), metasilicate ($SiO_3^{2-}$), orthosilicate ($SiO_4^{4-}$), disilicate ($Si_2O_5^{2-}$), trisilicate ($Si_3O_7^{2-}$), acetate ($CH_3COO^-$), borate ($BO_3^{3-}$) and/or tartrate ($C_4H_4O_6^{2-}$), and a centrifuge with a feed line to the intensive mixer.

Accordingly, the present invention relates to a device for separating glycoglycerolipids and glycosphingolipids from a lipid phase which contains glycoglycerolipids, glycosphingolipids, and acylglycerides, wherein the device comprises an intensive mixer for receiving the lipid phase, a cavity with a feed line to the intensive mixer for receiving an aqueous phase containing cations and anions of at least one salt which has a solubility of at least 30 g/l in water at 20° C. and which, upon dissociation in water, forms carbonate ($CO_3^{2-}$), bicarbonate ($HCO_3^-$), metasilicate ($SiO_3^{2-}$), orthosilicate ($SiO_4^{4-}$), disilicate ($Si_2O_5^{2-}$), trisilicate ($Si_3O_7^{2-}$), acetate ($CH_3COO^-$), borate ($BO_3^{3-}$) and/or tartrate ($C_4H_4O_6^{2-}$), and a centrifuge with a feed line to the intensive mixer.

Mixing and Homogenizing

As the technical teaching of this application shows, the efficiency of the process for the separation of glycoglycerolipids from a lipid phase also depends on how complete the mixing of the latter with the compounds dissolved in the water phase is. Since the provision of the aqueous salt solutions according to the invention can already be sufficient in an equimolar ratio with the glycoglycerolipids in order to extract the latter from the lipid phase and to make the separation process technically simple, the addition of a small amount of water containing the compounds according to the invention is sufficient. Since the liquids to be mixed have highly contrasting properties (hydrophilic-hydrophobic), considerable energy expenditure is necessary to produce the largest possible interfaces between the two liquids. According to the state of the art, various techniques are available for this purpose: dynamic mixing methods based on laminar or turbulent flows of the mixing components or static methods in which local pressure/stress gradients are generated, that lead to interface formation. It is known from the literature that the critical Weber number in laminar extensional and shear flows and mixing flows depends on the viscosity ratio $\lambda$ between disperse and continuous phase for individual drops. It follows that a mixture based on a laminar flow is not suitable for the usually highly viscous lipoid phases. In the case of turbulent flows, the progress of the flow is discontinuous, seemingly irregular, random and chaotic, thus a temporal and local resolution cannot be predicted. Based on the model of Kolmogorov (1949), different models were developed to simulate interface interactions in turbulent flows at the individual drops [Rodriguez-Rodriguez et al., 2006; Gordillo et al., 2006] and in the collective [Hinze, 1955; Davies, 1985; Vankova et al., 2007]. The models differ mainly in the equipment and material systems for which they were designed and in the assumptions about the turbulent flow. The variation of the break-up mechanism was achieved by the targeted adjustment of different Reynolds numbers, viscosities of the phases, densities of the phases, interfacial tensions, and disperse phase proportions. Since the Kolmogorov model only allows predicting which droplets cannot be broken up any more, but not how small the droplets will be during the break-up, only an upper particle size can be calculated with this model.

Cavitation occurs in liquids by the production of bubbles, which then collapse again. In general, three cavitation types are distinguished: steam cavitation (hard cavitation), gas cavitation (soft cavitation), and pseudocavitation [Riedel, 1973]. In hard cavitations, bubbles are created by lowering the static pressure below the vapor pressure, whereby the fluid partially evaporates and vapor bubbles are formed. Soft cavitations are created when the solubility of gases is lowered by decreasing the static pressure so that they form bubbles. If bubbles are already present in a liquid, a pressure drop leads to the growth of these bubbles, which is called pseudo-cavitation. Once the pressure rises above the vapor pressure, there is a sudden condensation of the liquid and therefore in extreme cases, bubbles collapse, which leads to high pressure variations. It is still not definitively resolved which forces can result from the cavitation and which mechanism thus leads to droplet breakup. Thus, although different methods are available which allow an intensive mixing process, neither a calculation nor an assumption about the efficiency of such methods for the extractability of dissolved glycoglycerolipids and glycosphingolipids can be made for the mixture of the fluid phases according to the invention and therefore can only be determined empirically.

Methods suitable for generating interfaces between two fluids can be divided into the four main groups: rotor-stator, high-pressure, ultrasonic, and membrane systems [Schubert, 2005]. The simplest variant of a rotor-stator system is the stirrer in a container. Further developments of the rotor-stator systems are toothed-wheel dispersing machines and colloid mills, which are characterized in that they allow significantly defined stresses. A drawback of rotor-stator systems is that the energy is often inhomogeneously introduced, resulting in broad drop-size distributions or long process times. Furthermore, only low specific energy introductions are often possible. High-pressure homogenizers are used in particular when very high specific energy introductions are required. High-pressure homogenizers essentially consist of a high-pressure pump and a crushing unit. As high-pressure pumps, piston pumps that produce homogenizing pressures between 50 and 10,000 bar are usually used. The crushing unit can consist of valves or diaphragms through which the pressurized fluids are pressed. The resulting stresses between the fluids are responsible for drop formation and drop deformation and crushing. The resulting effects on these properties are determined by the material properties of the fluids (such as viscosities of the phases, interface structure, type of surface-active material) as well as the pressure gradient and the geometry of the crushing device. Deformation and break-up are decisively determined by the viscosity ratio $\lambda$ between the disperse and continuous phase [Walstra, 1998; Kaufmann, 2002; Aguilar et al., 2004]. In particular for higher viscosity ratios k, the expansion flow in the inlet of the valve is advantageous because the stresses resulting from the turbulence and the cavitation being more effective on the filaments and thus fine droplets can be produced with the lowest possible energy introduction.

In the case of membranes and micro-structured systems, mostly premixed fluid phases are used, in which the droplets are broken up through the pore passage, by which an even narrower droplet size distribution can be produced than in the case of high-pressure homogenizers, however, high volumetric flows cannot be achieved at reasonable costs so far.

From the prior art, therefore, various methods and devices are known which enable an intensive mixing of fluids. Since the mixing result depends on a large number of influencing parameters, the mixing result and the associated effects on the chemical and physical interactions of compounds contained herein cannot be predicted. It was therefore surprising that a much larger amount of glycoglycerolipids could be extracted from a lipid phase by means of a toothed-wheel dispersing tool than by means of a rotor system. However, this clear difference could only be achieved by the exclusion of air/gas bubble formation.

It is therefore also the objective of this invention to provide a mixing and separator system by which a hydrolysis-poor or hydrolysis-free intensive mixture process of the aqueous salt solutions with a lipid phase can be produced without air/gas entry. Particularly suitable intensive mixers can be those intensive mixers which operate according to the high-pressure or rotor-stator homogenization principle.

The aqueous phase containing the above-mentioned salts or anions in dissolved form is present in a cavity or a storage container which is connected via a feed line with the intensive mixer so that a defined quantity or volume of the aqueous phase can be introduced into the intensive mixer.

Intensive mixing of the lipid phase and the aqueous phase then takes place in the intensive mixer. The intensive mixing is performed at atmospheric pressure and at a temperature in the range from 10 to 90° C., preferably from 15 to 70° C., more preferably from 20 to 60° C. and particularly preferably from 25 to 50° C. Therefore, the mixing and, preferably, intensive mixing at low temperature is preferably below 70° C., more preferably below 65° C., more preferably below 60° C., more preferably below 55° C., even more preferably below 50° C., even more preferably below 45° C. Protective gas, negative pressure or overpressure or also light exclusion is not necessary either during mixing or during subsequent workup. The low temperatures during the mixing as well as during the subsequent separation, for example by means of centrifugation and subsequent work-up ensure that no hydrolysis takes place. Thus, the present invention is also directed to a hydrolysis-free or at least hydrolysis-poor process for the separation of glycoglycerolipids and glycosphingolipids from lipid phases.

The term "hydrolysis-free" means a hydrolysis of the glycoglycerolipids and glycosphingolipids in the lipid phase of less than 1.0 wt %, preferably less than 0.5 wt %.

The term "hydrolysis-poor" means a hydrolysis of the glycoglycerolipids and glycosphingolipids in the lipid phase of less than 10.0 wt %, preferably less than 5.0 wt %, and more preferably less than 3.0 wt %.

Of course, this gentle separation of the fraction according to the invention, containing the glycoglycerolipids or the glycoglycerolipids and glycosphingolipids, also ensures that the other constituents of the lipid phase, for example the glycolipids, phospholipids and triacylglycerides, diacylglycerides and monoacylglycerides are not hydrolyzed.

It is therefore particularly preferred if the entire process according to the invention, preferably including the optional steps, is carried out at temperatures in the range from 10° C. to 90° C., preferably from 13° C. to 80° C., preferably from 15° C. to 70° C., more preferably 18° C. to 65° C., more preferably from 20° C. to 60° C., more preferably from 22° C. to 55° C. and particularly preferably from 25° C. to 50° C. or from 25° C. to 45° C.

The intensely mixed lipid phase and aqueous phase are then transferred to a centrifuge and separated into an aqueous glycoglycerolipid-rich phase to be removed and a lipid glycoglycerolipid-poor phase. An aqueous glycoglycerolipid-rich phase and lipid glycoglycerolipid-poor phase are then separated from each other. The term "intensely mixed" refers to a mechanical/physical mixing with an intensive mixer or such a mixing that the lipid phase and the aqueous phase form a homogeneous emulsion or dispersion.

In a preferred embodiment, the lipoid glycoglycerolipid-poor phase can be mixed again with an aqueous phase containing at least one compound which has at least one amidino group and/or at least one guanidino group, if the lipid glycoglycerolipid-poor phase contains fatty acids or carboxylic acids which are to be separated.

The aqueous phase containing at least one compound which has at least one amidino group and/or at least one guanidino group is fed from a storage container or a cavity which is connected to a feed line. After mixing, the mixture is again transferred to a centrifuge where the aqueous phase (i.e. the fatty acid-rich or carboxylic acid-rich phase) is separated and removed from the lipoid glycoglycerolipid-poor phase (i.e., the fatty acid-poor or carboxylic acid-poor phase) to obtain a further carboxylic acid-poor and glycoglycerolipid-poor lipid phase.

The device (shown schematically) in FIG. 3 has a receiving vessel 1 for receiving the aqueous phase or the salt solution of the salts described herein. From the receiving vessel 1 a line 2 (to which a pump 14 is connected to here) leads to container 3. This container 3 is preferably designed as a constant-pressure buffer container. For this purpose, container 3 can have an overflow return 4, which serves to return liquid from container 2 into receiving vessel 1 when an overflow level is exceeded.

Container 3 also has a discharge line 5 (preferably at its lower end) into which valve 6 is connected. The volume flow in discharge line 5 can be controlled with valve 6. The discharge line opens into mixer 7. In addition, feed line 8 leads into mixer 7, into which pump 13 can be connected to. A further phase, preferably the lipoid-containing (lipid) phase, can be passed into mixer 7 through feed line 8.

Mixer 7 also has discharge line 9 which opens into a feed of centrifuge 10. In mixer 7, the two introduced phases are mixed.

Centrifugal separation takes place in centrifuge 10, separating two phases of differing density, which flow out of the centrifuge through two outlets 11 and 12.

Mixer 7 can be designed in various ways. Thus, a static mixer or a dynamic mixer can be used. Also suitable are special shapes such as a high-shear mixer or a nano-reactor.

It is also conceivable to use the centrifuge itself as a mixer. In this case, the lipid phase and the salt solution (aqueous solution) are passed into the centrifuge through separate feed lines, for example, in distributor 15 of the centrifugal drum, the mixture of these two phases. Such distributors are known per se and are used to transfer the product that is running into the rotating drum.

A separator with a vertical axis of rotation, which is designed to separate two liquid phases of different densities, is preferably used as a centrifuge.

The device may also be designed to be operated under pressure p which is higher than atmospheric pressure. The following applies preferably: 1 bar≤p<10 bar. The discharge pressure in outlets 11 and 12 should be higher than the inlet pressure in the feed line to the centrifuge. An introduction of air is preferably to be avoided in the feed in order to avoid the formation of an emulsion in the mixer and/or in the centrifugal drum.

It has been shown that with this device it is possible to avoid formation of an emulsion with the result that, on the one hand, the separated fraction containing glycoglycerolipids and glycosphingolipids can be separated better because of a better phase separation and on the other hand the depletion of the lipid phase is more complete than with a mixing and separation system which does not prevent the exclusion of an air/gas introduction according to the invention.

The device according to the invention is therefore particularly suitable for realizing large-scale extraction of a hydrolysis-poor and particularly pure fraction of glycoglycerolipids and glycosphingolipids from lipid phases.

These devices according to the invention are designed for carrying out the methods according to the invention described below.

The present invention therefore also relates to a method for the hydrolysis-poor separation of glycoglycerolipids from a lipid phase which contains glycoglycerolipids and acylglycerides, comprising the steps:

A1) providing of a lipid phase containing glycoglycerolipids and acylglycerides,
B1) adding to the lipid phase an aqueous phase containing anions of at least one salt which has a solubility of at least 30 g/l in water at 20° C. and which, upon dissociation in water, forms carbonate ($CO_3^{2-}$), bicarbonate ($HCO_3^-$), metasilicate ($SiO_3^{2-}$), orthosilicate ($SiO_4^{4-}$), disilicate ($Si_2O_5^{2-}$), trisilicate ($Si_3O_7^{2-}$), acetate ($CH_3COO^-$), borate ($BO_3^{3-}$) and/or tartrate ($C_4H_4O_6^{2-}$),
C1) mixing the lipid phase and the aqueous phase,
D1) and separating the aqueous glycoglycerolipid-rich phase and obtaining a lipid glycoglycerolipid-poor phase.

The salt or the salts used are, of course, consist not only of anions but also cations, so that the present invention also relates to a method for the hydrolysis-poor separation of glycoglycerolipids from a lipid phase which comprises glycoglycerolipids and acylglycerides, comprising the steps:

A1) providing a lipid phase containing glycoglycerolipids and acylglycerides,
B1) adding to the lipid phase an aqueous phase containing the cations and anions of at least one salt which has a solubility of at least 30 g/l in water at 20° C. and which, upon dissociation in water, forms carbonate ($CO_3^{2-}$), bicarbonate ($HCO_3^-$), metasilicate ($SiO_3^{2-}$), orthosilicate ($SiO_4^{4-}$), disilicate ($Si_2O_5^{2-}$), trisilicate ($Si_3O_7^{2-}$), acetate ($CH_3COO^-$), borate ($BO_3^{3-}$) and/or tartrate ($C_4H_4O_6^{2-}$),
C1) mixing the lipid phase and the aqueous phase,
D1) and separating the aqueous glycoglycerolipid-rich phase and obtaining a lipid glycoglycerolipid-poor phase.

According to the invention, process steps A1) to D1) of the method disclosed herein are also carried out in the stated sequence A1)=>B1)=>C1)=>D1), or as long as additional process steps should be added, e.g. the steps A2), A2"), D2), and E1), the step sequence is as described herein, and step D2) follows after step D1), step E1) follows after step D1) or if step D2) exists, step E1) follows after step D2) and step A2) follows after A1) or alternatively to step A2) step A2') can follow after step A1).

The following possible step sequences thus result:
A1)=>B1)=>C1)=>D1)
A1)=>B1)=>C1)=>D1)=>D2)
A1)=>B1)=>C1)=>D1)=>E1)
A1)=>B1)=>C1)=>D1)=>D2)=>E1)
A1)=>A2)=>B1)=>C1)=>D1)
A1)=>A2)=>B1)=>C1)=>D1)=>D2)
A1)=>A2)=>B1)=>C1)=>D1)=>E1)
A1)=>A2)=>B1)=>C1)=>D1)=>D2)=>E1)
A1)=>A2')=>B1)=>C1)=>D1)
A1)=>A2')=>B1)=>C1)=>D1)=>D2)
A1)=>A2')=>B1)=>C1)=>D1)=>E1)
A1)=>A2')=>B1)=>C1)=>D1)=>D2)=>E1)

If the lipid phase also contains glycosphingolipids in addition to the glycoglycerolipids, these can be separated from the lipid phase together with the glycoglycerolipids. In such a case, the method according to the invention is as follows:

Method for the hydrolysis-poor separation of glycoglycerolipids and glycosphingolipids from a lipid phase which comprises glycoglycerolipids and glycosphingolipids and acylglycerides, comprising the steps:

A1) providing a lipid phase containing glycoglycerolipids, glycosphingolipids, and acylglycerides,
B1) adding to the lipid phase an aqueous phase containing anions of at least one salt which has a solubility of at least 30 g/l in water at 20° C. and which, upon dissociation in water, forms carbonate ($CO_3^{2-}$), bicarbonate ($HCO_3^-$), metasilicate ($SiO_3^{2-}$), orthosilicate ($SiO_4^{4-}$), disilicate ($Si_2O_5^{2-}$), trisilicate ($Si_3O_7^{2-}$), acetate ($CH_3COO^-$), borate ($BO_3^{3-}$) and/or tartrate ($C_4H_4O_6^{2-}$),
C1) mixing the lipid phase and the aqueous phase,
D1) and separating the aqueous glycoglycerolipid-rich and/or glycosphingolipid-rich phase and obtaining a lipid glycoglycerolipid-poor and/or glycosphingolipid-poor phase.

Accordingly, the present invention relates to a method for the hydrolysis-poor separation of glycoglycerolipids and glycosphingolipids from a lipid phase comprising glycoglycerolipids and glycosphingolipids and acylglycerides, comprising the steps of:

A1) providing a lipid phase containing glycoglycerolipids, glycosphingolipids and acylglycerides,
B1) adding to the lipid phase an aqueous phase containing the cations and anions of at least one salt which has a solubility of at least 30 g/l in water at 20° C. and which, upon dissociation in water, forms carbonate ($CO_3^{2-}$), bicarbonate ($HCO_3^-$), metasilicate ($SiO_3^{2-}$), orthosilicate ($SiO_4^{4-}$), disilicate ($Si_2O_5^{2-}$), trisilicate ($Si_3O_7^{2-}$), acetate ($CH_3COO^-$), borate ($BO_3^{3-}$) and/or tartrate ($C_4H_4O_6^{2-}$),
C1) mixing the lipid phase and the aqueous phase,
D1) and separating the aqueous glycoglycerolipid-rich and/or glycosphingolipid-rich phase and obtaining a lipid glycoglycerolipid-poor and/or glycosphingolipid-poor phase.

The preferred cation of the salt or cations of a mixture of salts are: $Na^+$, $K^+$, $Li^+$, $Mg^{2+}$, $Ca^{2+}$, $Ti^{2+}$, $Ti^{4+}$, $Co^{2+}$, $Co^{3+}$, $Ni^{2+}$, $Cu^{2+}$, $Zn^{2+}$, $Sn^{2+}$ and/or $Sn^{4+}$. Particularly preferred are $Na^+$ and $K^+$.

Acylglycerides are monoacylglycerides, diacylglycerides and triacylglycerides. Triacylglycerides are compounds in which three acyl residues (Ay, Ay', Ay") are attached to glycerol via an ester bond. A general formula for triacylglycerides is shown below. Accordingly, in the case of diacylglycerides, two acyl residuals (Ay, Ay') are attached to glycerol via an ester bond, and in the case of monoacylglycerides, an acyl residual (Ay) is bound to glycerol via an ester bond.

Glycoglycerolipids are understood to be compounds in which two acyl residues (Ay, Ay') are attached to glycerol via an ester bond, and a saccharide is preferably bound to the third hydroxyl group (or the third oxygen atom) of the glycerol via the anomeric carbon atom. A general formula for glycoglycerolipids is shown below.

According to the invention, the acylglycerides are not transferred into the aqueous glycoglycerolipid-rich phase and remain in the lipoid glycoglycerolipid-poor phase. The term "glycoglycerolipid-rich phase" thus denotes the fraction of the lipid phase used which consists of glycoglycerolipids or wherein the glycoglycerolipids are enriched. Accordingly, the term "glycoglycerolipid-poor phase" means the fraction of the lipid phase obtained, wherein the glycoglycerolipids are reduced or from which the glycoglycerolipids have been removed. If the used lipid phase also contains glycosphingolipids in addition to the glycoglycerolipids, the term "glycoglycerolipid-poor phase" accordingly means the fraction of the used lipid phase, wherein the glycosphingolipids and the glycoglycerolipids have been reduced or removed and the term "glycoglycerolipid-rich phase" means thereby the fraction of the used lipid phase, which consists of glycoglycerolipids and glycosphingolipids or wherein the glycoglycerolipids and the glycosphingolipids are enriched.

Glycolipids, on the other hand, denote substances in which an acyl residue (Ay) is bound to a hydroxyl group of a saccharide and preferably to the hydroxyl group on the anomeric carbon atom of the saccharide. A general formula for glycolipids and glycoglycerolipid glycoglycerolipids is shown below.

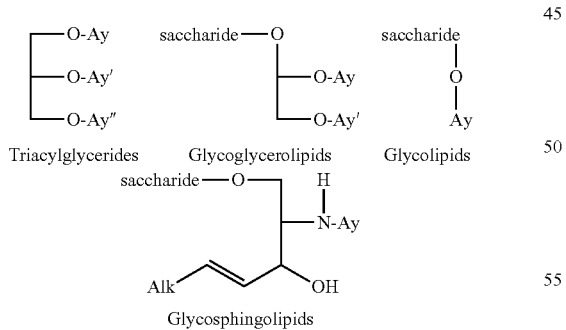

The term "saccharide" means a sugar residue, wherein the sugar residue may be a monosaccharide, oligosaccharide, or polysaccharide. The acyl residues (Ay, Ay' and Ay") are preferably fatty acid residues. The lipids and fatty acid residues are discussed further below.

Glycosphingolipids consist of a saccharide residue which is bound to a ceramide residue. The term "Alk" stands for an alkyl residue and preferably a long-chain alkyl residue with more than 10 carbon atoms. If the saccharide residue is galactose, these monoglycosylceramides are referred to as cerebrosides. An example is shown below:

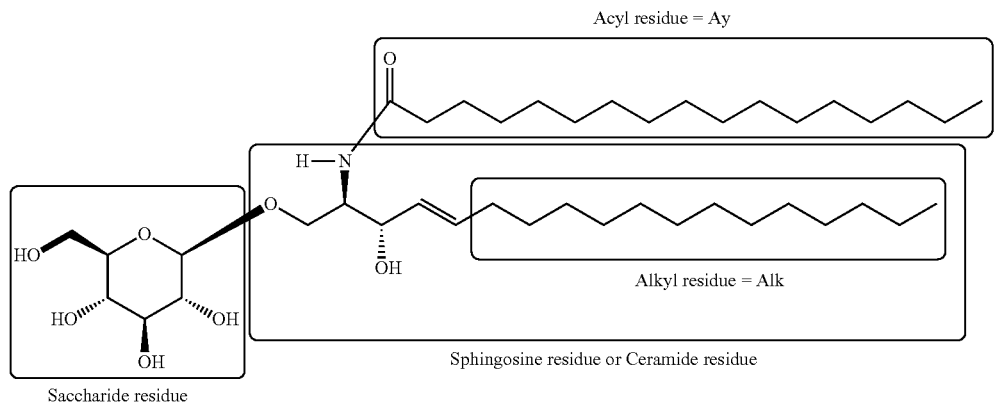

In the following, a diglycosyllipid is shown as an example for a glycolipid and a monoglycosylglycerolipid is shown as an example of a glycoglycerolipid.

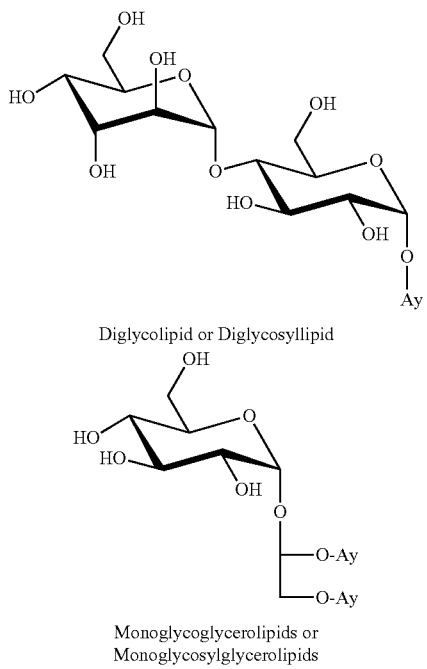

The inventive methods are particularly useful to separate glycoglycerolipids or mixtures of glycoglycerolipids and glycosphingolipids from the lipid phase. If the lipid phases in addition to the glycoglycerolipids or in addition to glycoglycerolipids and glycosphingolipids also contain glycolipids and/or glycophospholipids, then mainly glycolipids but also glycophospholipids and in particular the neutral glycophospholipids together with the glycoglycerolipids or glycoglycerolipids and glycosphingolipids can be separated from the lipid phases. In particular methods of the invention are suitable to separate monoglycosylsphingolipids, diglycosylsphingolipids, triglycosylsphingolipids, tetraglycosylsphingolipids, pentaglycosylsphingolipids, monoacyl-monoglycosylsphingolipids, mono acyldiglycosylsphingolipids, monoacyltriglycosylsphingolipids, monoacyltetraglycosylsphingolipids, monoacylpentaglycosylsphingolipids, diacyldi-glycosylsphingolipids, diacyltriglycosylsphingolipids, diacyltetraglycosylsphingolipids, diacylpentaglycosyl-sphingolipids, triacyltriglycosylsphingolipids, triacyltetraglycosylsphingolipids, triacylpenta-glycosylsphingolipids, tetraacyltetraglycosylsphingolipids, tetraacylpentaglycosyl-sphingolipids, pentaacylpentaglycosylsphingolipids, monoglycosylglycerolipids, diglycosylglycerolipids, triglycosylglycerolipids, tetraglycosyl-glycerolipids, pentaglycosylglycerolipids, hexaglycosylglycerolipids, heptaglycosyl-glycerolipids, octaglycosylglycerolipids, nonaglycosylglycerolipids, decaglycosylglycero-lipids, monoacyldiglycosylglycerolipids, monoacyltriglycosylglycerolipids, monoacyltetraglycosylglycerolipids, monoacylpentaglycosylglycerolipids, monoacylhexa-glycosylglycerolipids, monoacylheptaglycosylglycerolipids, monoacyloctaglycosyl-glycerolipids, monoacylnonaglycosylglycerolipids, monoacyldecaglycosylglycerolipids, diacyltriglycosylglycerolipids, diacyltetraglycosylglycerolipids, diacylpentaglycosyl-glycerolipids, diacylhexaglycosylglycerolipids, diacylheptaglycosylglycerolipids, diacyloctaglycosylglycerolipids, diacylnonaglycosylglycerolipids, diacyldecaglycosyl-glycerolipids, triacyltetraglycosylglycerolipids, triacylpentaglycosylglycerolipids, triacylhexaglycosylglycerolipids, triacylheptaglycosylglycerolipids, triacyloctaglycosyl-glycerolipids, triacylnonaglycosylglycerolipids, triacyldecaglycosylglycerolipids, tetraacylpentaglycosylglycerolipids, tetraacylhexaglycosylglycerolipids, tetraacyl heptaglycosylglycerolipids, tetraacyloctaglycosylglycerolipids, tetraacylnona-glycosylglycerolipids, tetraacyldecaglycosylglycerolipids, pentaacylhexaglycosyl-glycerolipids, pentaacylheptaglycosylglycerolipids, pentaacyloctaglycosylglycerolipids, pentaacylnonaglycosylglycerolipids, pentaacyldecaglycosylglycerolipids, hexaacyl heptaglycosylglycerolipids, hexaacyloctaglycosylglycerolipids, hexaacylnonaglycosyl-glycerolipids, hexaacyldecaglycosyl-glycerolipids, heptaacyloctaglycosylglycerolipids, heptaacylnonaglycosylglycerolipids, heptaacyldecaglycosyl-glycerolipids, octaacyl-nonaglycosylglycerolipids, octaacyldecaglycosylglycerolipids and/or nonaacyldecaglycosylglycerolipids from a lipoid phase.

It was very surprising that, with the methods according to the invention, the rather lipoid glycoglycerolipids and glycosphingolipids could be transferred into the aqueous phase. The lipophilic glycoglycerolipids and glycosphingolipids are compounds which cannot be transferred into the aqueous phase, or are only poorly transferred into the aqueous phase by extraction with water or by hydrophilic compounds. In this context, the term "poor" means that only less than 10% by weight of the total amount of glycoglycerolipids or glycoglycerolipids and glycosphingolipids can be separated from the lipoid phase by an extraction step with water. Therefore, it is also preferred that the glycoglycerolipids contain no carboxylate, sulfate, sulfonate, or phosphate group(s). It is also preferred that the glycosphingolipids contain no carboxylate, sulfate, sulfonate, or phosphate group(s).

Thus, the present invention is directed in particular to methods for separating glycoglycerolipids, wherein the glycoglycerolipids are lipophilic glycoglycerolipids having a lipophilicity index GL of $1.0 \leq GL \leq 6.0$, wherein the lipophilicity index GL is calculated according to the following formula:

$$GL = \frac{\text{Sum of the carbon atoms of the acyl residues}}{\text{Sum of hydroxy and amino groups}}$$

The "sum of the carbon atoms of the acyl group" means the sum of all the carbon atoms of all acyl groups. When two acyl residues (Ay and Ay') are located on the glycerol residue one or more further acyl residues can be located on the saccharide residues. However, it is also possible that a further acyl residue is present on an acyl residue. The carbonyl carbon atom of the acyl residues is also included in the calculation.

The "sum of the hydroxyl and amino groups" means all hydroxyl groups and amino groups in the molecule including the hydroxyl and amino groups which are on an acyl residual. For example, the following diglycosylglycerolipid, wherein R is an alkyl residual having 16 carbon atoms, has a lipophilicity index GL of 4.9.

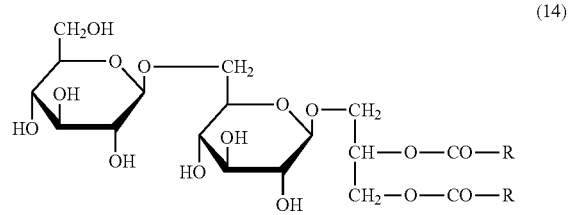

(14)

If glycosphingolipids are also present in the lipoid phase, the present invention preferably relates to methods for separating glycoglycerolipids and glycosphingolipids, wherein the glycosphingolipids are lipophilic glycosphingolipids having a lipophilicity index SL of $1.0 \leq SL \leq 7.0$, wherein the lipophilicity index SL is calculated according to the following formula:

$$SL = \frac{\text{Sum of carbon atoms of the ceramide residue}}{\text{Sum of hydroxy and amino and amido groups}}$$

The "sum of the carbon atoms of the ceramide residue" means the sum of all the carbon atoms in the ceramide residue, including the carbon atoms of the acyl residue in the ceramide residual. If further acyl residue should be attached to the saccharide residue or to the acyl residue in the ceramide residue, the carbon atoms of these acyl residues are added to the sum of the carbon atoms of the ceramide residue. In the case of the acyl residue, the carbonyl carbon atom and the ceramide residue also include the amide carbon atom. The "sum of the hydroxy and amino and amide groups" means all hydroxy groups, amino groups and amide groups in the molecule including the hydroxyl and amino groups which are on an acyl residue. The hydroxy group is the —OH group, the amino group is the —NH$_2$ group, and the —NH—CO— or the —CO—NH— group is referred to as the amide group. For example, the following glycosphingolipid, wherein R is an alkenyl residue having 15 carbon atoms, has a lipophilicity index SL of 5.7.

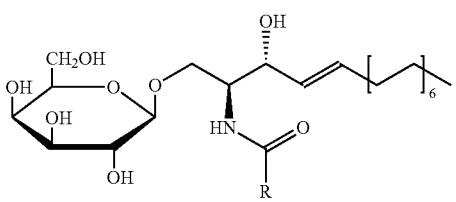

As an alternative to the lipophilicity index, the HLB lipophilicity index can also be used which is shown in FIG. 2 and where over a range of 0 to 20, lipophilic substances are at the lower end of the range, hydrophilic substances are at the upper region of the range, and equi-amphiphilic substances (equally lipophilic as hydrophilic) are grouped in the region around 10; the scale is especially intended for characterization of emulsifying agents.

Since the methods according to the invention are useful for the separation and recovery of glycoglycerolipids from lipid phases, it is preferred when the methods according to the invention for the separation of glycoglycerolipids comprise the following step D2) after step D1):

D2) recovering the glycoglycerolipids from the separated aqueous phase.

In the event that the lipid phase in addition to the glycoglycerolipids also includes glycosphingolipids, it is preferred when the methods according to the invention for separating glycoglycerolipids and glycosphingolipids comprise the following step D2) after step D1):

D2) recovering the glycoglycerolipids and the glycosphingolipids from the separated aqueous phase.

In the event that the lipid phase contains in addition to the glycoglycerolipids, or in addition to the glycoglycerolipids and glycosphingolipids also glycolipids and/or glycophospholipids, it is preferred when the inventive methods for the separation of glycoglycerolipids and glycosphingolipids comprises the following step D2) after step D1):

D2) recovering the glycoglycerolipids and glycolipids and/or glycophospholipids or recovery of the glycoglycerolipids and glycosphingolipids and glycolipids and/or glycophospholipids from the separated aqueous phase.

Because of their diverse suitability as bio-surfactants, it is an objective of the present invention to isolate from the lipid phases glycoglycerolipids or mixtures containing glycoglycerolipids and glycophospholipids and provide them for other uses. Depending on the composition and ingredients of the lipid phase, which for the major part (preferably >80 wt %) consists of acyl glycerides and especially of triacylglycerides, fractions can be separated from the lipid phases, where the fractions containing glycophospholipids or fractions containing glycosphingolipids, or fractions containing sterylglycosides, or fractions containing glycophospholipids and glycosphingolipids, or fractions containing glycophospholipids and sterylglycosides, or fractions containing glycosphingolipids and sterylglycosides, or fractions containing glycophospholipids and sterylglycosides and glycosphingolipids from which the glycophospholipids, glycosphingolipids, sterylglycosides or mixtures of the above-mentioned substances can be obtained. Thus, the present invention also relates to aqueous glycoglycerolipid-rich phases, aqueous sterylglycosid-rich phases, and lipid glycoglycerolipid-poor phases obtainable or obtained by any of the methods disclosed herein.

The term glycophospholipids refers to a glycerophospholipid wherein a saccharide residue is attached to the phosphate group, e.g. in the case of phosphatidylinositol.

In the aforesaid nomenclature, e.g. "monoacyltetraglycosylglycerolipids" means that an acyl residue is located on one of the 4 saccharide residues. The acyl residue is preferably not located on the saccharide residue on which the diacylglycerol residue is located. If an amino sugar is among the saccharide residues, the acyl residue can also be located on the amino group of the amino sugar. Thus, the term "triacylhexaglycosylglycerolipids" refers to a hexasaccharide wherein on three hydroxy groups of the hexasaccharide an acyl residue is attached. The acyl residues can be different acyl residuals, of course. It is not necessary and is also the exception that these acyl residues are the same. The acyl residues on the glycerol residue are also usually not identical and are, as a rule, other acyl residues than the acyl residues which are bound directly to the saccharide residues. In the aforementioned example, the glycoglycerolipid consists of a diacylglycerol residue and a hexasaccharide, with three acyl radicals being attached to the hexasaccharide. Here, preference is given to when no more than one acyl residue is present per saccharide residue and the saccharide residue is not an acyl residue to which the diacylglycerol residue is attached. If amino sugars are present in the hexasaccharide, the acyl residue may be bound to the amino group of the amino sugar.

Furthermore, the term "glycoglycerolipids" also includes those which carry an alkyl residue, alkenyl residue, or alkynyl residue on the glycerol residue instead of an acyl residue, and those which contain two residues on the glycerol residue instead of both acyl residues selected from the group consisting of alkyl residue, alkenyl residue, and alkynyl residue. These compounds can be represented by the following general formulas in which Alk and Alk' are independently of each other, an alkyl residue, alkenyl residue, or alkynyl residue:

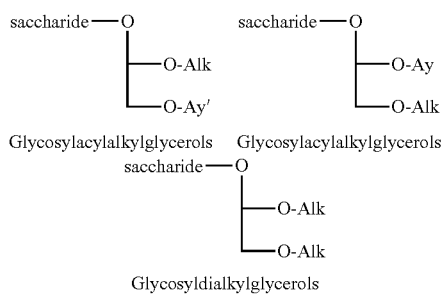

Thus, the present invention concerns preferably a method for separating glycosyldiacylglycerides, glycosylacylalkylglycerides, and glycosyldialkylglycerides from a lipid phase, and more preferably for separating monoglycosylsphingolipids, diglycosylsphingolipids, triglycosylsphingolipids, tetraglycosylsphingolipids, pentaglycosylsphingolipids, monoglycosylglycerolipids, diglycosylglycerolipids, triglycosylglycerolipids, tetraglycosylglycerolipids, pentaglycosylglycerolipids, hexaglycosylglycerolipids, heptaglycosylglycerolipids, monoacyldiglycosylglycerolipiden, monoacyltriglycosylglycerolipids, monoacyltetraglycosylglycerolipids, monoacylpentaglycosylglycerolipids, monoacylhexaglycosylglycerolipids, and/or monoacylheptaglycosyl glycerolipids.

Among acyl residues are preferred acyl residues of fatty acids and among the alk residues preferably alkyl residues, alkenyl residues, or alkynyl residues of fatty acids. The term "alkenyl" includes not only monoolefinic residues, but also di-, tri- and polyolefinic residues and carbon residues with at least one double bond and at least one triple bond. The term "alkynyl residue" includes carbon residues having one, two, three, or more triple bonds.

Examples of preferred acyl residues are: Dodecanoyl, hexadecanoyl, octadecanoyl, eicosanoyl, docosanoyl, tetracosanoyl, cis-9-tetradecenoyl, 9-cis-hexadecenoyl, cis-6-octadecenoyl, cis-9-octadecenoyl, cis-11-octadecenoyl, 9-cis-eicosenoyl, cis 11-eicosenoyl, cis-13-docosenoyl, cis-15-tetracosenoyl, 9,12-octadecadienoyl, 6,9,12-octadecatrienoyl, 8,11,14-eicosatrienoyl, 5,8,11,14-eicosatetraenoyl, 7,10,13,16-docosatetraenoyl, 4,7,10,13,16-docosapentaenoyl, 9,12,15-octadecatrienoyl, 6,9,12,15-octadecatetraenoyl, 8,11,14,17-eicosatetraenoyl, 5, 8,11,14,17-eicosapentaenoyl, 5,8,11,14,17-ecosapentaenoyl, 7,10,13,16,19-docosapentaenoyl, 4,7,10,13,16,19-docosahexaenoyl, 5,8,11-eicosatrienoyl, 1,2-dithiolan-3-pentanoyl, 6,8-dithianoctanoyl, docosaheptadecanoyl, eleostearoyl, calendoyl, catalpoyl, taxoleoyl, pinolenoyl, sciadonoyl, retinoyl, 14-20 methylpentadecanoyl, pristanoyl, phytanoyl, 11,12-Methyleneoctadecanoyl, 9,10-methylenehexadecanoyl, 9,10-epoxystearoyl, 9,10-Epoxyoctadec-12-enoyl, 6-octadecinoyl, t11-octadecen-9-inoyl, 9-octadecinoyl, 6-octadecen-9-inoyl, t10-heptadecen-8-inoyl, 9-octadecen-12-inoyl, t7,t11-octadecadiene-9-inoyl, t8,t10-octadecadiene-12-inoyl, 5,8,11,14-eicosatetrainoyl, 2-hydroxytetracosanoyl, 2-hydroxy-15-tetracosenoyl, 12-hydroxy-9-ynloyl, octadecenoyl, and 14-hydroxy-11-eicosenoyl.

The preferred alkyl, alkenyl, or alkynyl residues are the carbon residues (i.e. without the COOH group) of the following acids: hexanoic acid, octanoic acid, decanoic acid, dodecanoic acid, tetradecanoic acid, hexadecanoic acid, heptadecanoic acid, octadecanoic acid, eicosanoic acid, docosanoic acid, tetracosanoic acid, cis-9-tetradecenoic acid, cis-9-hexadecenoic acid, cis-6-octadecenoic acid, cis-9-octadecenoic acid, cis-11-octadecenoic acid, cis-9-eicosenoic acid, cis-11-eicosenoic acid, cis-13-docosenoic acid, cis-15-tetracosenoic acid, t9-octadecenoic acid, t11-octadecenoic acid, t3-hexadecenoic acid, 9,12-octadecadienoic acid, 6,9,12-octadecatrienoic acid, 8,11,14-eicosatrienoic acid, 5,8,11,14-eicosatetraenoic acid, 7,10,13,16-docosatetraenoic acid, 4,7,10,13,16-docosapentaenoic acid, 9,12,15-octadecatrienoic acid, 6,9,12,15-octadecatetraenoic acid, 8,11,14,17-eicosatetraenoic acid, 5,8,11,14,17-eicosapentaenoic acid, 7,10,13,16,19, docosapentaenoic acid, 4,7,10,13,16,19-docosahexaenoic acid, 5,8,11-eicosatrienoic acid, 9c11t13t-eleostearic acid, 8t10t12c-calendic acid, 9c11t13c-catalpic acid, 4,7,9,11,13,16,19-docosaheptadecanoic acid, taxoleic acid, pinolenic acid, sciadoic acid, 6-octadecinoic acid, t11-octadecen-9-inoic acid, 9-octadecinoic acid, 6-octadecen-9-inoic acid, t10-heptadecen-8-inoic acid, 9-octadecen-12-inoic acid, t7,t11-octadecadien-9-inoic acid, t8,t10-octadecadien-12-inoic acid, 5,8,11,14-eicosatetrainoic acid, retinoic acid, isopalmitic acid, pristanic acid, phytanic acid, 11,12-methylene-5-octadecanoic acid, 9,10-methylenehexadecanoic acid, coronaric acid, (R, S)-lipoic acid, (S)-lipoic acid, (R)-(methylsulfanyl)-hexanoic acid, 2,4-bis (methylsulfanyl)-butanoic acid, 1,2-dithiolane-carboxylic acid, (R,S)-6.8-dithian-octanoic acid, tariric acid, santalbic acid, stearic acid, 6,9-octadeceninoic acid, pyrulic acid, crepenic acid, heisteric acid, t8, t10-octadecadien-12-inoic acid, ETYA, cerebronic acid, hydroxynervic acid, ricinoleic acid, lesquerolic acid, brassylic acid and thapsic acid.

A further aspect of the present invention is directed to the separated substances so that the present invention also relates to the mixtures containing the glycoglycerolipids or the glycoglycerolipids and glycosphingolipids or the glycoglycerolipids and glycosphingolipids and the glycolipids and/or the glycophospholipids. These substance mixtures of various glycoglycerolipids or of various glycoglycerolipids and glycosphingolipids or of various glycoglycerolipids and glycosphingolipids and glycolipids and/or glycophospholipids can be obtained by the processes according to the invention and in particular by extraction from the separated aqueous phase.

The glycoglycerolipids and, if present in the lipoid phase, the glycosphingolipids are recovered from the lipoid phase by adding to the lipoid phase an aqueous phase containing anions that contains anions of at least one salt which has a solubility of at least 30 g/l in water at 20° C. and which, upon dissociation, forms carbonate ($CO_3^{2-}$), bicarbonate ($HCO_3^-$), metasilicate ($SiO_3^{2-}$), orthosilicate ($SiO_4^{4-}$), disilicate ($Si_2O_5^{2-}$), trisilicate ($Si_3O_7^{2-}$), acetate ($CH_3COO^-$), borate ($BO_3^{3-}$) and/or tartrate ($C_4H_4O_6^{2-}$), followed by preferably intensive mixing of both phases and separation of the aqueous phase by centrifugation. The term "at least one salt" as used herein is intended to illustrate that, of course, also a plurality of salts, i.e. mixtures of salts can be used as well as salts of the same anions and different cations, e.g. sodium acetate and potassium acetate as well as salts of identical cations and different anions, e.g. sodium bicarbonate and sodium silicate. Of course, mixtures of salts of different cations and different anions, e.g. sodium carbonate and potassium tartrate, and on the other hand, salts with different anions and/or different cations in a salt, e.g. sodium carbonate can be used.

It is unusual to use salts with different anions and/or different cations in a salt, e.g. sodium potassium carbonate.

Suitable salts which form the abovementioned anions in water are preferably $Na_2CO_3$, $K_2CO_3$, $NaHCO_3$, $KHCO_3$, $Na_2SiO_3$, $K_2SiO_3$, $Na_4SiO_4$, $K_4SiO_4$, $Na_2Si_2O_5$, $K_2Si_2O_5$, $Na_2Si_3O_7$, $K_2Si_3O_7$, $NaOOCCH_3$, $KOOCCH_3$, $Cu(OOCCH_3)_2$, $Na_2C_4H_4O_6$, $K_2C_4H_4O_6$, $Na_3BO_3$, and $K_3BO_3$. These salts are added at least in stoichiometric amounts relative to the glycoglycerolipids. If glycosphingolipids are also present in the lipoid phase in addition to glycoglycerolipids, these salts are added in at least stoichiometric amounts, based on the total amount of the glycoglycerolipids and glycosphingolipids. Furthermore, at least an excess of 0.2 to 1.0 molar equivalents should be used. An excess of 1.0 molar equivalent corresponds to a 100% excess. Preference is generally given to an excess of 1.0 molar equivalent to 10.0 molar equivalents, more preferably from 2.0 molar equivalents to 9.0 molar equivalents, more preferably 3.0 molar equivalents to 8.0 molar equivalents, more preferably 4.0 molar equivalents to 7.0 molar equivalents.

According to the invention, the glycoglycerolipids, and if present the glycosphingolipids in the lipoid phase, are transferred from a lipoid phase into the aqueous phase and not from an aqueous phase containing salts as disclosed herein to an aqueous phase, and can be separated from lipoid phase by separation of the aqueous phase and can be obtained from the aqueous phase. In the process according to the invention, the organic compounds to be separated are always in a lipoid phase. An aqueous solution of one or more salts which forms anion(s) in water comprising carbonate ($CO_3^{2-}$), bicarbonate ($HCO_3^-$), metasilicate ($SiO_3^{2-}$), orthosilicate ($SiO_4^{4-}$), disilicate ($Si_2O_5^{2-}$), trisilicate ($Si_3O_7^{2-}$), acetate ($CH_3COO^-$), borate ($BO_3^{3-}$) and/or tartrate ($C_4H_4O_6^{2-}$) is added to the lipoid phase, and by this means the glycoglycerolipids, and if present the glycosphingolipids, are transferred into the aqueous phase together with this anion or by these anions. In this extraction step, preferably no additional organic solvents are used. Thus, the additional use of organic solvents can also be excluded.

In addition, a variety of salts with different anions have been tested and, according to the invention, only the anions disclosed herein are capable of transferring the glycoglycerolipids and glycosphingolipids into the aqueous phase. Anions such as chloride, bromide, iodide, nitrate, nitrite, nitride, sulfate, sulfite, sulfide, phosphate and many others are not capable of this and therefore cannot be used according to the invention.

In a preferred embodiment of the present invention, the aqueous phase added in step B1) contains the abovementioned anions in the form of their sodium salts. In a preferred embodiment of the present invention, the aqueous phase added in step B1) does not contain further anions in addition to the above-captioned anions except chloride and/or bromide ions.

It is therefore preferred according to the invention that the aqueous phase added in step B1) containing carbonate ($CO_3^{2-}$), bicarbonate ($HCO_3^-$), metasilicate ($SiO_3^{2-}$), orthosilicate ($SiO_4^{4-}$), disilicate ($Si_2O_5^{2-}$), trisilicate ($Si_3O_7^{2-}$), acetate ($CH_3COO^-$), borate ($BO_3^{3-}$) or tartrate ($C_4H_4O_6^{2-}$) does not contain any further anions, i.e. no phosphate, no iodide, no fluoride, no nitrite, no nitrate, no hydrogen phosphate, no dihydrogen phosphate and no cyanide. The aqueous phase preferably contains $Na^+$, $K^+$, $Li^+$, $Mg^{2+}$, $Ca^{2+}$, $Ti^{2+}$, $Ti^{4+}$, $Co^{2+}$, $Co^{3+}$, $Ni^{2+}$, $Cu^{2+}$, $Zn^{2+}$, $Sn^{2+}$ and/or $Sn^{4+}$, and especially preferred only $Na^+$ and/or $K^+$.

However, the person skilled in the art is aware that, depending on the source and quality of the water used for preparing the aqueous phase added during step B1) or also under step A2) or step A2') or step E1), unavoidable impurities may be present in the form of other anions or cations.

It is also preferred if one or more of the following cations is/are present in the added aqueous phase: $Li^+$, $Mg^{2+}$, $Ca^{2+}$, $Ti^{2+}$, $Ti^{4+}$, $Co^{2+}$, $Co^{3+}$, $Ni^{2+}$, $Cu^{2+}$, $Zn^{2+}$, $Sn^{2+}$ or $Sn^{4+}$. The lipoid phase is therefore preferably treated in step B1) with an aqueous phase which contains cations of a salt which has a solubility of at least 30 g/l in water at 20° C. and which, when dissociated in water, contains of $Li^+$, $Mg^{2+}$, $Ca^{2+}$, $Ti^{2+}$, $Ti^{4+}$, $Co^{2+}$, $Co^{3+}$, $Ni^{2+}$, $Cu^{2+}$, $Zn^{2+}$, $Sn^{2+}$ or $Sn^{4+}$ ions. Of course, these aqueous phases can also contain anions to the abovementioned cations, e.g. sulfate, bromide, acetate. The addition of iron ions should be avoided.

Suitable salts which can be added to the aqueous phase to be added are, for example LiOAc, LiBr, $MgBr_2$, $CaBr_2$, $Mg(OAc)_2$, $Ca(OAc)_2$, $MgCO_3$, $CaCO_3$, $Ti(OAc)_2$, $Ti(OAc)_4$, $Ni(OAc)_2$, $TiBr_2$, $TiBr_4$, $CoBr_2$, $CoBr_3$, $NiBr_2$, $CuBr_2$, $Cu(OAc)_2$, $ZnBr_2$, $Zn(OAc)_2$, $Sn(OAc)_2$, $SnBr_2$, $Sn(OAc)_4$ or $SnBr_4$.

The use of chloride salts such as NaCl should be avoided because chloride salts are known to have corrosive effects and attack the processing devices which are preferably made of steel. Thus, the use of chloride salts, e.g. LiCl, $MgCl_2$, $CaCl_2$, NaCl, $TiCl_2$, $TiCl_4$, $CoCl_2$, $CoCl_3$, $NiCl_2$, $CuCl_2$, KCl, $ZnCl_2$, $SnCl_2$ and $SnCl_4$ should be avoided. The use of chloride salts is preferably excluded according to the invention.

The aqueous phase to be added in step B1) preferably has a pH in the range from 7.0 to 13.5, more preferably from 7.5 to 12.0, more preferably from 8.0 to 11.0. The pH can be adjusted, if necessary, by addition of e.g. acetic acid. The pH also depends, of course, on the added salt. When using metasilicate (MS), the pH is preferably in the range from 12.0 to 13.5, preferably 12.5 to 13.5.

When using carbonate (sodium carbonate: NC), the pH is preferably in the range from 10.0 to 12.0, preferably 10.5 to 11.5.

When using acetate (Ac; sodium acetate: NAc) the pH is preferably in the range of 7.0 to 9.0, preferably 7.5 to 8.5.

When using hydrogen carbonate (HC; sodium hydrogen carbonate: NHC), the pH is preferably in the range from 7.0 to 9.0, preferably 7.5 to 8.5.

The aqueous phase to be added in step E1) preferably has a pH in the range from 10.0 to 14.0, more preferably from 11.0 to 13.7, more preferably from 12.0 to 13.5. The pH can be adjusted, if necessary, by the addition of, for example, acetic acid.

The aqueous phase is added to the lipoid phase preferably at room temperature or at a temperature in the range from 10 to 50° C.

The mixing takes place at atmospheric pressure and at a temperature in the range from 10° C. to 90° C., preferably from 15° C. to 70° C., more preferably from 20° C. to 60° C. and particularly preferably from 25° C. to 50° C. The separation of the aqueous phase after the mixing procedure is preferably carried out at atmospheric pressure and at a temperature in the range from 10° C. to 90° C., preferably from 15° C. to 70° C., more preferably from 20° C. to 60° C. and particularly preferably from 25° C. to 50° C.

Since the separation of glycoglycerolipids and glycosphingolipids according to the invention can be carried out from lipoid phases in which, for the aforementioned reasons, hydratable, easily water-soluble compounds can also be present, it may be of interest to separate these compounds separately. Before the addition of the aqueous phase described in the previous paragraphs according to step B1), after step A1) the following step A2) can be carried out A2) adding water as aqueous phase to the lipoid phase, followed by mixing the lipoid phase and the aqueous phase and separating the aqueous phase.

Thus, one aspect of the present invention is directed to a method comprising the following step A2) after step A1) and before step B1):

A2) adding water as aqueous phase to the lipoid phase, followed by mixing the lipoid phase and the aqueous phase and separating the aqueous phase.

Instead of water as an aqueous phase or neutral aqueous phase, an acidic aqueous phase which contains, for example, citric acid, phosphoric acid, acetic acid, formic acid, or oxalic acid can also be used. Therefore, a further possible variant of the present invention is directed to a method which comprises, after step A1) and before step B1), the following step A2'):

A2') adding to the lipoid phase an aqueous carboxylic acid solution or an aqueous solution of an inorganic acid having a pH between 3.0 and 5.0 as aqueous phase, followed by mixing the lipoid phase and the aqueous phase and separating the aqueous phase.

Suitable inorganic acids are, for example phosphoric acid, sulfuric acid and hydrochloric acid. In some embodiments of the present invention, it may be advantageous and thus it is preferred to carry out step A2) or A2') as the first step after the provision of a lipoid phase containing acyl glycerides, glycolipids, glycoglycerolipids, glycophospholipids, phospholipids, and free fatty acids. This is particularly true for lipoid phases which contain, in addition to acyl glycerides, glycolipids, glycoglycerolipids, and glycophospholipids, a particularly large number of phospholipids, which can be separated off well by a step A2) or A2'). After mixing the lipid phase with an aqueous phase in the form of distilled water or a weak acid, the resulting aqueous phase is separated from the lipid phase and can be discarded or collected for further use. Hydrophilic substances such as salts but also readily hydrolysable phospholipids (for example, phosphatidylcholine, also referred to as lecithin) or glycolipids with carboxylate, sulfate and/or sulfonate group(s) can be separated. Fatty acids, glycoglycerolipids and glycophospholipids are thereby not separated or only to a very small degree.

The recovery of a purer form of glycoglycerolipids and glycophospholipids is possible by separating hydratable compounds from a lipid phase, which substantially facilitates the further processing of the separated fraction of the glycoglycerolipids and glycophospholipids. Therefore, the process steps A1) and A2) are particularly preferred embodiments in order to obtain a purer form of glycoglycerolipids and glycophospholipids with the process steps B1) and B2) according to the invention. Thus, the present invention also relates to mixtures comprising glycoglycerolipids, glycosphingolipids, sterylglycosides or combinations of the aforementioned substances, e.g. glycoglycerolipids and glycosphingolipids or glycoglycerolipids and glycosphingolipids and sterylglycosides, obtainable by any of the methods disclosed herein.

However, with the process steps according to A), A1), and A2), other nonhydratable compounds such as free fatty acids or carboxylic acids in addition to glycoglycerolipids and glycosphingolipids are not removed from the lipid phases. Free fatty acids and phospholipids or glycophospholipids may be separated while separating the glycoglycerolipids and glycosphingolipids according process steps B), B1), and B2), which adversely affects the quality of the separated glycoglycerolipids and glycosphingolipids. It has been shown that, in particular, the coseparation of free fatty acids, carboxylic acids, and phospholipids can be controlled by a suitable selection of process parameters. This relates, in particular, to the adjustment of the pH value of the described aqueous salt solutions. Thus, it was shown that even in the case of a high content of the free fatty acids in the lipid phase, the content of the free fatty acids and phospholipids or glycophospholipids remains substantially unchanged during the separations of the glycoglycerolipids and glycosphingolipids carried out with the process steps B), B1), and B2) when the pH of the aqueous solution was adjusted to a neutral level. This makes it possible for the first time to obtain a particularly advantageous and pure fraction of glycoglycerolipids and glycosphingolipids with an aqueous separation process, so that a particularly preferred embodiment of process steps B), B1), and B2) using aqueous solutions of the anions or salts mentioned herein having a pH value which is neutral or which lies in a neutral range.

In some industrial applications, the lipid phases are also mixtures of economic interest which can be treated with the apparatuses and methods according to the invention for recovering a hydrolysis-poor and pure fraction of glycoglycerolipids and glycosphingolipids are. This relates in particular to vegetable oils. It was shown now for the first time that the removal of glycoglycerolipids and glycophospholipids is relevant to the further processing of these lipid phases. A depletion of free fatty acids from lipid phases that consists of >90 wt %, preferably >95 wt %, and more preferably >98 wt % of triacylglycerols, to values <0.1 wt % was not shown hitherto Surprisingly, it could be found now that by means of an extraction with an aqueous solution of guanidine- or amidino-compounds that is carried out following the aqueous extraction of glycoglycerolipids and glycosphingolipids according to steps B1) to D1), a virtually complete removal of free fatty acids and phospholipids still remaining in an alkane or triglyceride mixture is possible. Such a reduction of fatty acids and phospholipids could not be achieved with the same amidino or guanidino compounds which have been brought together with an alkane or triglyceride mixture following a conventional process from the prior art. Therefore, the combination of an aqueous extraction according to the invention according to steps B1) to D1) and the additional aqueous extraction with an amidino or guanidine compound represents a particularly advantageous process for obtaining an optimal reduction of fatty acids and phospholipids.

At the same time, an extremely advantageous further reduction of the lipid phase treated with the devices and methods according to the invention can thereby be made possible so that the invention is also directed to obtaining a highly refined glycoglycerolipid-poor lipid phase.

As a result, triglyceride and alkane mixtures can be obtained which have residual contents of free fatty acids and phospholipids which are clearly below the current standards required by German authorities for e.g. the quality of biogenic fuels, such as biodiesel. This also applies to the allowed maximum values of alkaline earth metals and metal ions, which, however, are already reduced after the extraction method according to steps B1) to D1). Nevertheless, further reduction is possible by the additional aqueous extraction with an amidino or guanidine compound.

A particularly preferred embodiment of the present invention therefore relates to processes which comprise the following step E1) after step D1):

E1) adding an aqueous phase containing at least one compound having at least one amidino group and/or at least one guanidino group to the glycoglycerolipid-poor lipid phase, followed by mixing the glycoglycerolipid-poor lipid phase and the aqueous phase and separating the aqueous phase.

If the method according to the invention comprises step D2), an especially preferred embodiment of the present invention is directed to processes which comprise the following step E1) after step D2):

E1) adding an aqueous phase containing at least one compound having at least one amidino group and/or at least one guanidino group to the glycoglycerolipid-poor lipid phase, followed by mixing the glycoglycerolipid-poor lipid phase and the aqueous phase and separating the aqueous phase.

Examples of suitable compounds having at least one guanidino group (also called guanidino compounds) and/or having at least one amidino group (also called amidino compounds) are disclosed in detail in International Patent Application WO 2011160857 A2. The chemical residue is the guanidino group $H_2N$—C(NH)—NH— as well as its cyclic forms, and the chemical residue $H_2N$—C(NH)— as the amidino group, as well as its cyclic forms (see examples below). Preference is given to guanidino compounds which have at least one carboxylate group (—COOH) in addition to the guanidino group. It is also preferred that the carboxylate group(s) is/are separated from the guanidino group in the molecule by at least one carbon atom. Preference is also given to amidino compounds which have at least one carboxylate group (—COOH) in addition to the amidino group. It is also preferred that the carboxylate group(s) is/are separated from the amidino group in the molecule by at least one carbon atom.

These guanidino compounds and amidino compounds preferably have a distribution coefficient $K_{OW}$ between n-octanol and water of <6.3 ($K_{OW}$<6.3).

Particular preference is given to arginine derivatives. Arginine derivatives are defined as compounds having a guanidino group and a carboxylate group or an amidino group and a carboxylate group wherein guanidino group and carboxylate group or amidino group and carboxylate group are separated from each other by at least one carbon atom, that means that at least one of the following groups is located between the guanidino group or the amidino group and the carboxylate group: —$CH_2$—, —CHR—, —CRR'—, where R and R' are independently from each other any chemical residues. Of course, the distance between the guanidino group and the carboxylate group or the amidino group and the carboxylate group can also be more than one carbon atom, for example, by the following groups —$(CH_2)_n$—, —$(CHR)_n$—, —$(CRR')_n$— with n=2, 3, 4, 5, 6, 7, 8 or 9 as it is the case for such as example, amidinopropionic acid, amidinobutyric acid, guanidinopropionic acid or guanidinobutyric acid. Compounds having more than one guanidino group and more than one carboxylate group are, for example, oligoarginine, and polyarginine.

Examples of preferred compounds having a guanidino group or an amidino group and a carboxylate group are shown below.

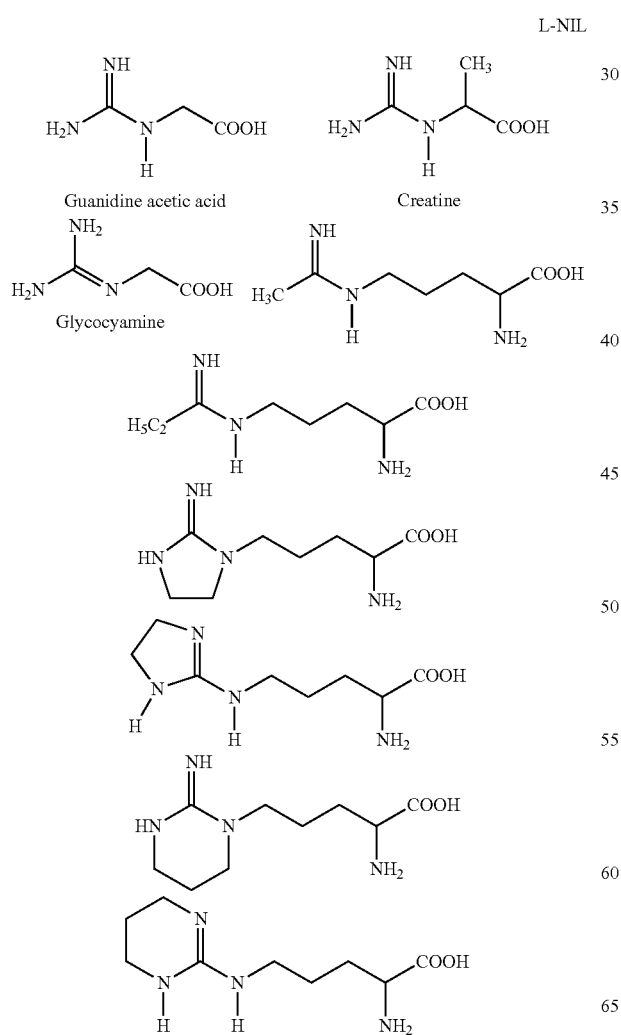

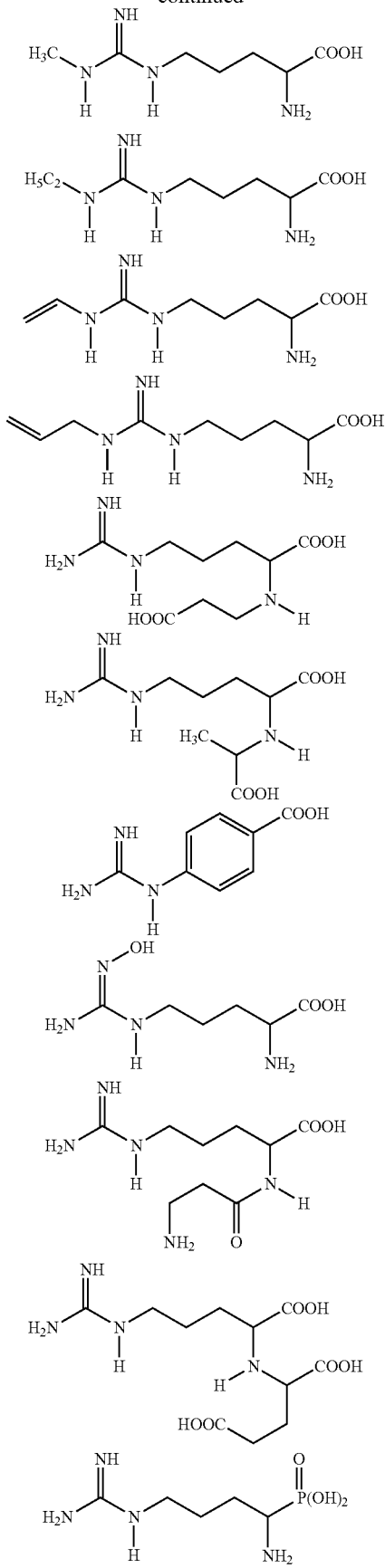

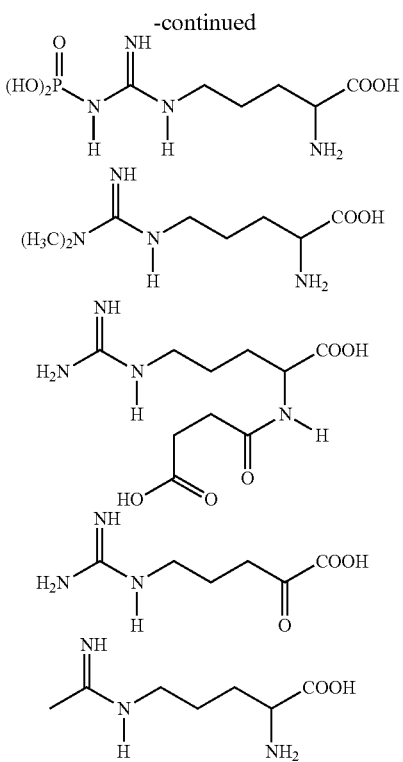

Preferred arginine derivatives are compounds of the following general formula (I) or (II)

$$RR'N\underset{X}{\overset{NR''}{\bigvee}}L \quad (I)$$

$$R'HN\underset{X}{\overset{NR''}{\bigvee}}L \quad (II)$$

wherein
R', R", R'" and R"" mean independently from each other:
—H, —OH, —CH=CH$_2$, —CH$_2$—CH=CH$_2$, —C(CH$_3$)=CH$_2$, —CH=CH—CH$_3$, —C$_2$H$_4$—CH=CH$_2$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, cyclo-C$_3$H$_5$, cyclo-C$_4$H$_7$, cyclo-C$_5$H$_9$, cyclo-C$_6$H$_{11}$, —PO$_3$H$_2$, —PO$_3$H$^-$, —PO$_3{}^{2-}$, —NO$_2$, —C≡CH, —C≡C—CH$_3$, —CH$_2$—C≡CH, —C$_2$H$_4$—C≡CH, —CH$_2$—C≡C—CH$_3$, or
R' and R" together create one of the following groups:
—CH$_2$—CH$_2$—, —CO—CH$_2$—, —CH$_2$—CO—, —CH=CH—, —CO—CH=CH—, —CH=CH—CO—, —CO—CH$_2$—CH$_2$—, —CH$_2$—CH$_2$—CO—, —CH$_2$—CO—CH$_2$— or —CH$_2$—CH$_2$—CH$_2$—;
X is —NH—, —NR"—, —O—, —S—, —CH$_2$—, —C$_2$H$_4$—, —C$_3$H$_6$—, —C$_4$H$_8$— or —O$_5$H$_{10}$— or for one C1 to C5 carbon chain, which can be substituted by one or more residues: —F, —Cl, —OH, —OCH$_3$, —OC$_2$H$_5$, —NH$_2$, —NHCH$_3$, —NH(C$_2$H$_5$), —N(CH$_3$)$_2$, —N(C$_2$H$_5$)$_2$, —SH, —NO$_2$, —PO$_3$H$_2$, —PO$_3$H$^-$, —PO$_3{}^{2-}$, —CH$_3$, —C$_2$H$_5$, —CH=CH$_2$, —COOH, —COOCH$_3$, —COOC$_2$H$_5$, —COCH$_3$, —COC$_2$H$_5$, —O—COCH$_3$, —O—COC$_2$H$_5$, —CN, —CF$_3$, —C$_2$F$_5$, —OCF$_3$, —OC$_2$F$_5$;
L represents a hydrophilic substituent, selected from a group consisting of: —NH$_2$, —OH, —PO$_3$H$_2$, —PO$_3$H$^-$, —PO$_3{}^{2-}$, —OPO$_3$H$_2$, —OPO$_3$H$^-$, —OPO$_3{}^{2-}$, —COOH, —COO$^-$, —CO—NH$_2$, —NH$_3{}^+$, —NH—CO—NH$_2$, —N(CH$_3$)$_3{}^+$, —N(C$_2$H$_5$)$_3{}^+$, —N(C$_3$H$_7$)$_3{}^+$, —NH(CH$_3$)$_2{}^+$, —NH(C$_2$H$_5$)$_2{}^+$, —NH(C$_3$H$_7$)$_2{}^+$, —NHCH$_3$, —NHC$_2$H$_5$, —NHC$_3$H$_7$, —NH$_2$CH$_3{}^+$, —NH$_2$C$_2$H$_5{}^+$, —NH$_2$C$_3$H$_7{}^+$, —SO$_3$H, —SO$_3{}^-$, —SO$_2$NH$_2$, —CO—COOH, —O—CO—NH$_2$, —C(NH)—NH$_2$, —NH—C(NH)—NH$_2$, —NH—CS—NH$_2$, —NH—COOH,

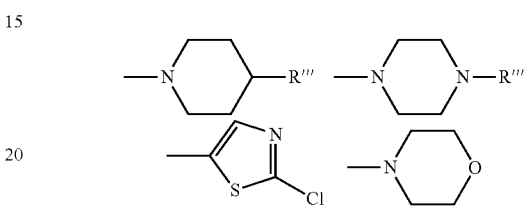

Process step E1) is particularly suitable for obtaining further purified glycolipid-poor and carboxylic acid-poor lipoid phases which at the same time have only minimal residual amounts of potassium, phosphorus, iron, calcium, free fatty acids, glycoglycerolipids, and glycosphingolipids. Thus, a further aspect of the present invention is directed to a carboxylic acid-poor lipoid phase and a glycolipid- and carboxylic acid-poor lipoid phase which are obtained by a process according to the invention.

The step E1) can also be carried out as step A2) instead of the washing step with water or the washing step with an aqueous carboxylic acid solution or an aqueous phosphoric acid solution, or as step A3) after a washing step with water [step A2)] or as step A3) after a washing step with aqueous carboxylic acid solution or with aqueous phosphoric acid solution, sulfuric acid solution or hydrochloric acid solution [step A2')]. The use of step E1) is particularly advantageous after the initial step A2), since the acids introduced for the recovery of a particularly advantageous hydrolysis-poor and phospholipid-poor fractions of glycoglycerolipids and glycosphingolipids can be completely removed under particularly careful conditions, so that a carboxylic acid-poor lipoid phase can be obtained simultaneously under particularly gentle conditions.

According to the invention it is therefore preferred to carry out step A2) or A2') in order to remove readily water-soluble constituents of the lipoid phase, which are substances with an HLB value of preferably >18, preferably >16, more preferably >15, and then conduct step B1) according to the invention in order to obtain an aqueous phase with a purity of the recoverable glycoglycerolipids and glycosphingolipids as high as possible.

If it is desired to further separate glycoglycerolipids and glycosphingolipids having charged groups, e.g. phosphate, sulfonate, sulfate from those without a charged group (e.g. without phosphate, sulfonate, sulfate), then step B1) is preferably carried out by means of an aqueous phase containing anions of at least one salt which has a solubility of at least 30 g/L in water at 20° C. and upon dissociation in water forming carbonate (CO$_3{}^{2-}$), bicarbonate (HCO$_3{}^-$), metasilicate (SiO$_3{}^{2-}$), orthosilicate (SiO$_4{}^{4-}$), disilicate (Si$_2$O$_5{}^{2-}$), trisilicate (Si$_3$O$_7{}^{2-}$) ions, and then the obtained separated aqueous phase containing the glycoglycerolipids and glycosphingolipids is extracted by means of suitable organic solvents such as, for example, dimethylether or chloroform. If desired, it may be helpful to additionally use polar solvents for separation, such as methanol. In this further separation step, the glycoglycerolipids and glycosphingolipids with charged groups, e.g. phosphate groups, sulfonate groups, or sulfate groups remain in the aqueous phase, and the glycoglycerolipids and glycosphingolipids without ionic groups are transferred into the organic phase.

If, on the other hand, it is desired to obtain a fraction of glycoglycerolipids and glycosphingolipids without ionic groups, then a washing step is preferably carried out by means of water [step A2)] or acid solution [step A2'].

According to the invention, the following glycoglycerolipids can preferably be obtained from a lipid phase:

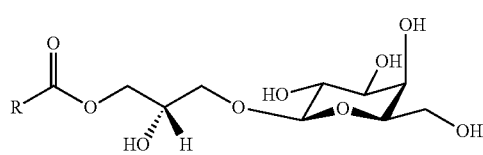

1-acyl-3-O-β-D-galactosyl-sn-glycerol

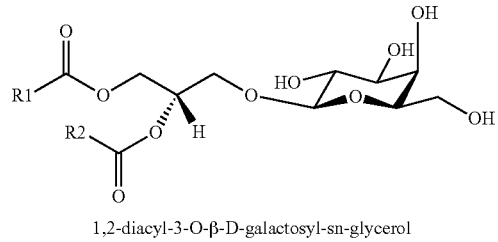

1,2-diacyl-3-O-β-D-galactosyl-sn-glycerol

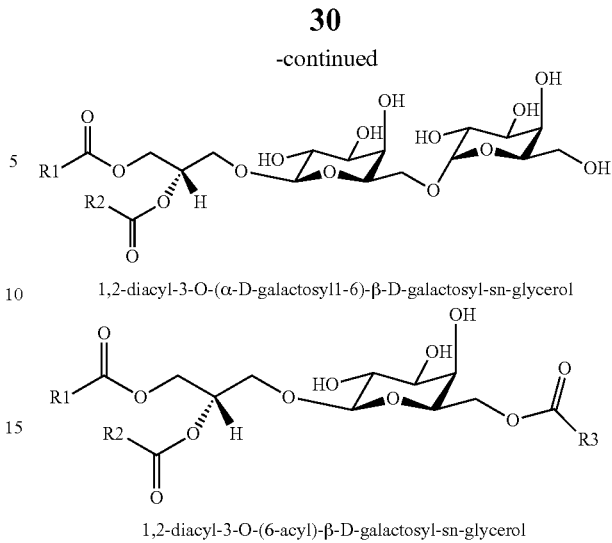

1,2-diacyl-3-O-(α-D-galactosyl1-6)-β-D-galactosyl-sn-glycerol 1,2-diacyl-3-O-(6-acyl)-β-D-galactosyl-sn-glycerol The residues R, R$^1$, and R$^2$ here represent the carbon residues of fatty acids, the formulas RCOOH, R$^1$COOH and R$^2$COOH being the corresponding fatty acids. In particular, fatty acid residues (RCOO—, R$^1$COO— and R$^2$COO—) having 14 to 24 carbon atoms, preferably 16 to 22 carbon atoms and more preferably 18 to 20 carbon atoms are preferred. In addition, fatty acid residues with an even number of carbon atoms are preferred.

Examples of glycoglycerolipids without ionic groups which can be obtained according to the invention from lipoid phases are, for example,

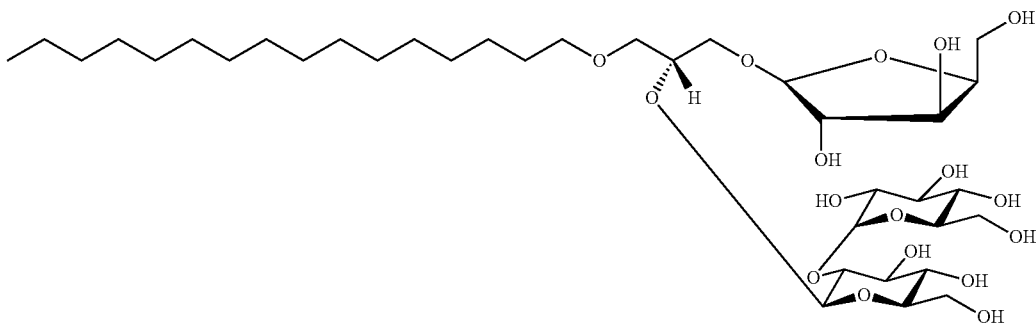

1-hexadecanyl-2-((2'-α-glucosyl)-β-glucosyl)-3-β-xylosyl-sn-glycerol

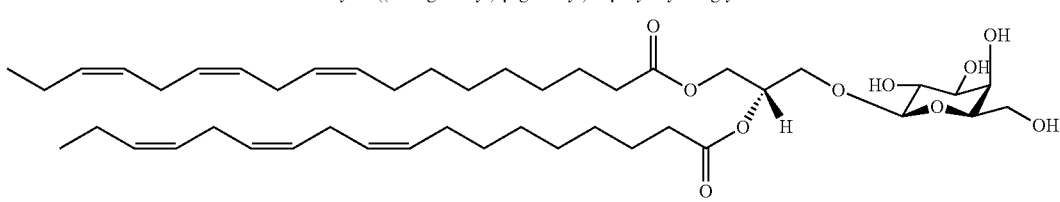

1,2-di(9Z,12Z,15Z-octadecatrienoyl)-3-O-β-D-galactosyl-sn-glycerol

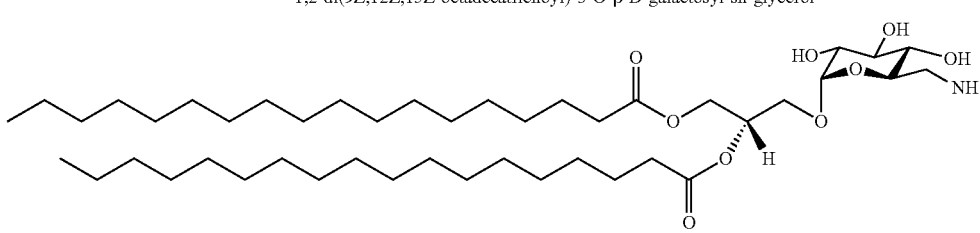

1,2-dioctadecanoyl-3-O-(6-deoxy-6-amino-α-D-glucosyl)-sn-glycerol

-continued

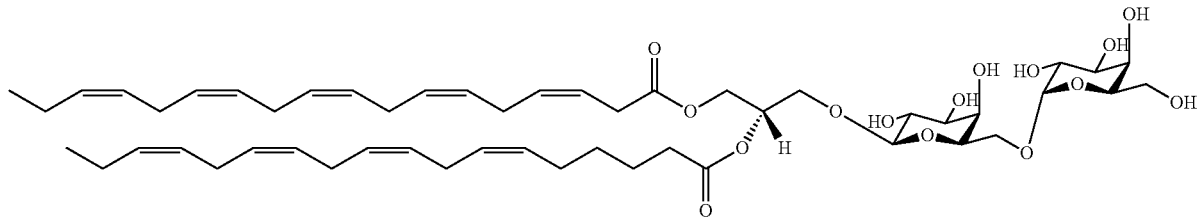

1-(3Z,6Z,9Z,12Z,15Z-octadecapentaenoyl)-2-(6Z,9Z,12Z,15Z-octadecatetraenoyl)-3-
O-(6'-O-α-D-galactosyl-β-D-galactosyl)-sn-glycerol

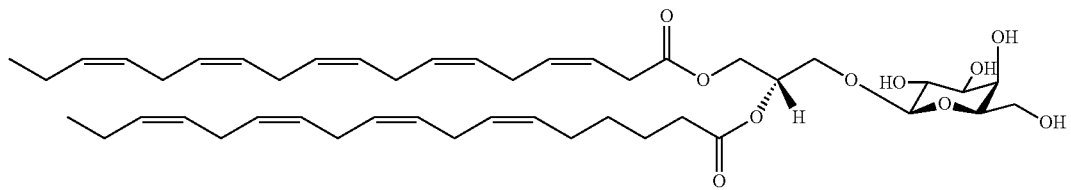

1-(3Z,6Z,9Z,12Z,15Z-octadecapentaenoyl)-2-(6Z,9Z,12Z,15Z-octadecatetraenoyl)-3-
O-β-D-galactosyl-sn-glycerol

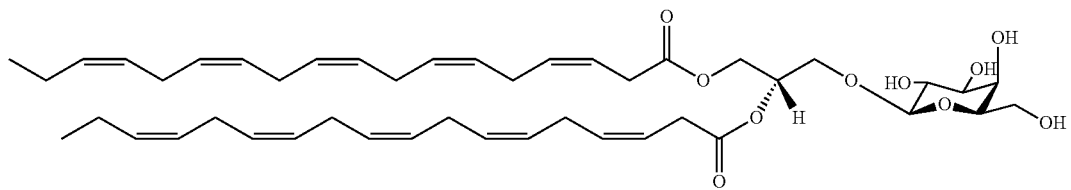

1,2-di-(3Z,6Z,9Z,12Z,15Z-octadecapentaenoyl)-3-O-β-D-galactosyl-sn-glycerol

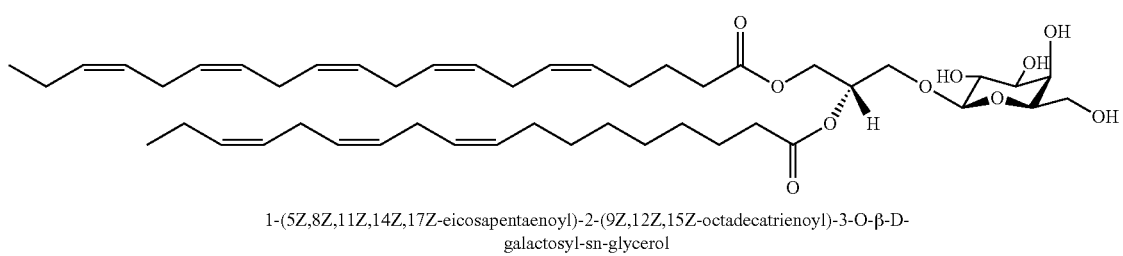

1-(5Z,8Z,11Z,14Z,17Z-eicosapentaenoyl)-2-(9Z,12Z,15Z-octadecatrienoyl)-3-O-β-D-
galactosyl-sn-glycerol

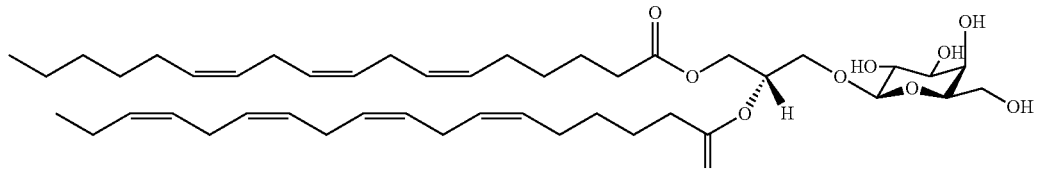

1-(9z,12z,15z-octadecatrienoyl)-2-(6Z,9Z,12Z,15Z-octadecatetraenoyl)-3-O-β-D-
galactosyl-sn-glycerol

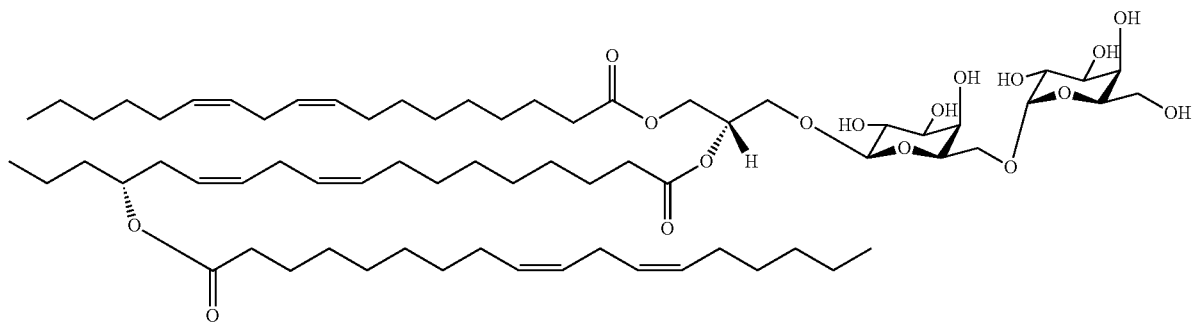

1-(9Z,12Z,-octadecadienoyl)-2-(15R-[9Z,12Z-octadecadienoyloxy]-9Z,12Z-
octadecadienoyl)-3-(α-D-galactosyl-1-6-β-D-galactosyl)-sn-glycerol -continued

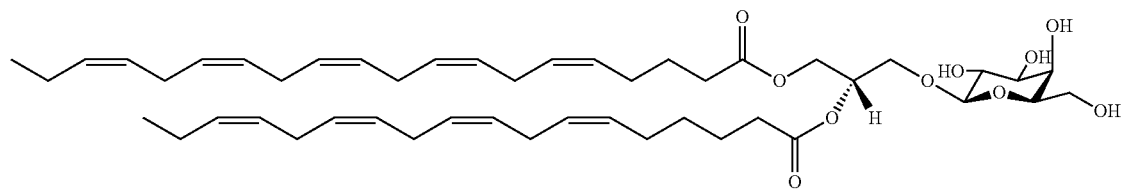

1-(5Z,8Z,11Z,14Z,17Z-eicosapentaenoyl)-2-(6Z,9Z,12Z,15Z-octadecatetraenoyl)-3-
O-β-D-galactosyl-sn-glycerol

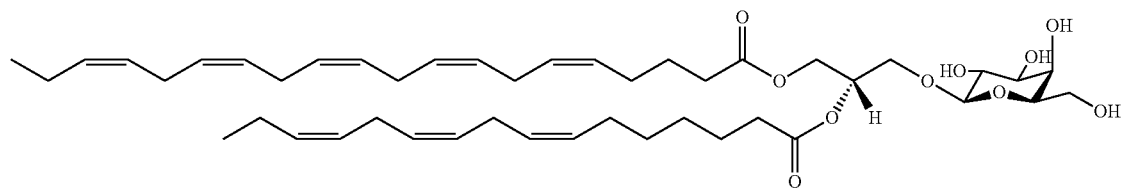

1-(5Z,8Z,11Z,14Z,17Z-eicosapentaenoyl)-2-(7Z,10Z,13Z-hexadecatrienoyl)-3-O-β-D-galactosyl-sn-glycerol

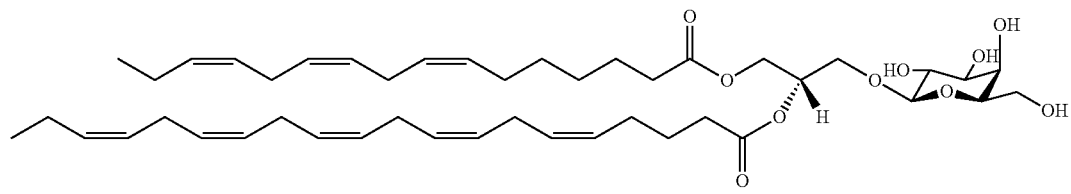

1-(7Z,10Z,13Z-hexadecatrienoyl)-2-(5Z,8Z,11Z,14Z,17Z-eicosapentaenoyl)-3-O-β-D-
galactosyl-sn-glycerol

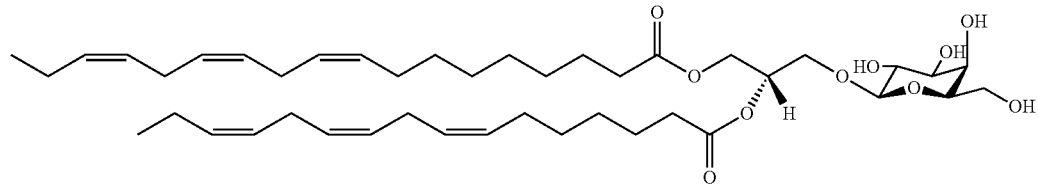

1-(9Z,12Z,15Z-octadecatrienoyl)-2-(7Z,10Z,13Z-hexadecatrienoyl)-3-O-β-D-
galactosyl-sn-glycerol

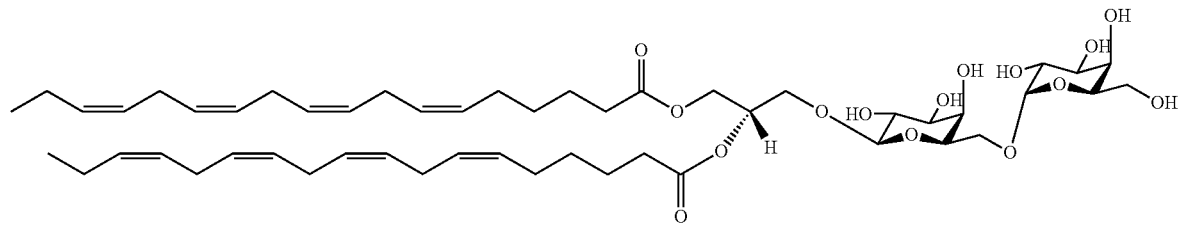

1,2-di-(6Z,9Z,12Z,15Z-octadecatetraenoyl)-3-O-β-D-galactosyl-sn-glycerol

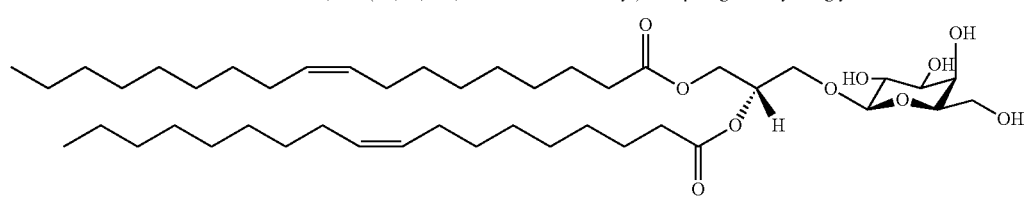

1,2di-(9Z-octadecenoyl)-3-O-β-D-galactosyl-sn-glycerol

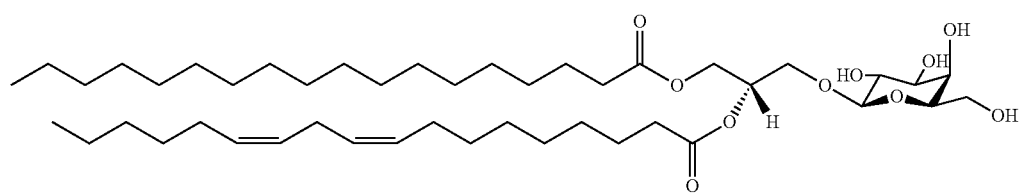

1-octadecanoyl-2-(9Z,12Z-octadecadienoyl)-3-O-β-D-galactosyl-sn-glycerol

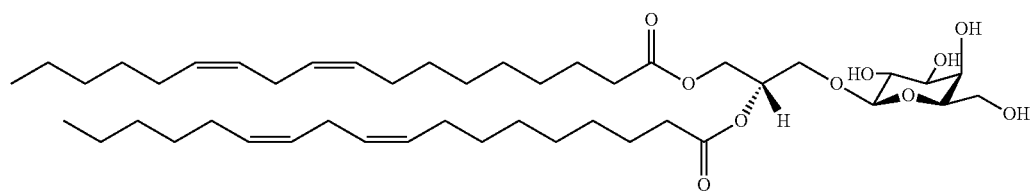

1,2-di-(9Z,12Z-octadecadienoyl)-3-O-β-D-galactosyl-sn-glycerol

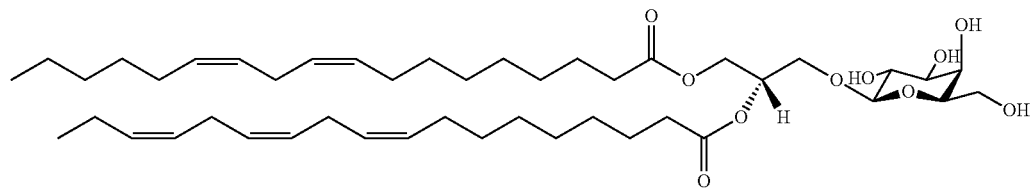

1-(9Z,12Z-octadecadienoyl)-2-(9Z,12Z,15Z-octadecatrienoyl)-3-O-β-D-galactosyl-sn-glycerol

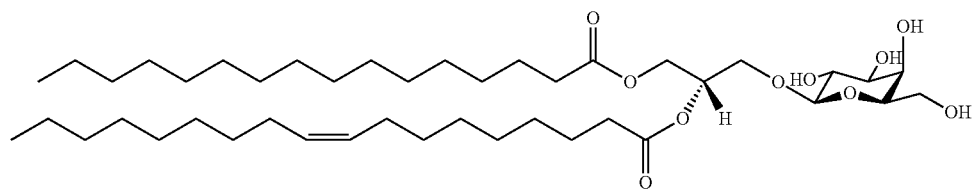

1-hexadecanoyl-2-(9Z-octadecenoyl)-3-O-β-D-galactosyl-sn-glycerol

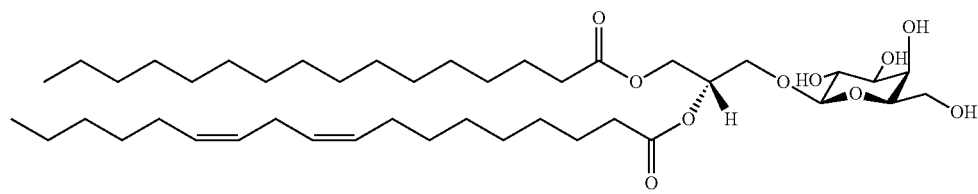

1-hexadecanoyl-2-(9Z,12Z-octadecadienoyl)-3-O-β-D-galactosyl-sn-glycerol

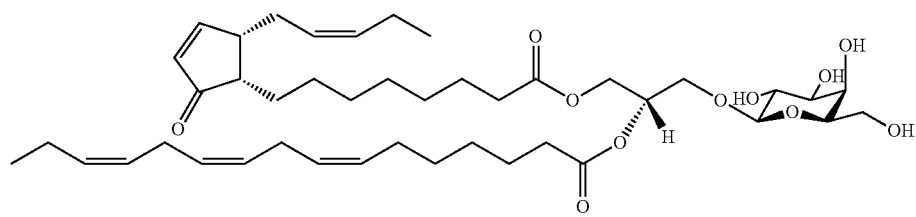

1-(9S,13S-12-oxo-11,15Z-phytodienoyl)-2-(7Z,10Z,13Z-hexadecatrienoyl)-3-O-(β-D-galactosyl)-sn-glycerol

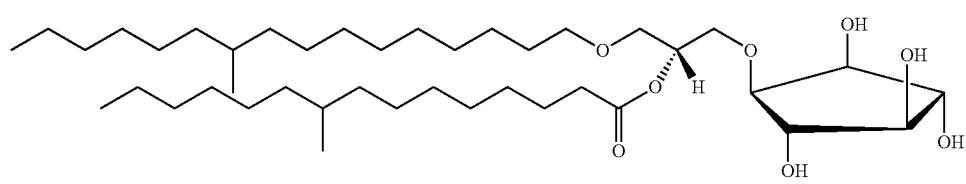

1-O-(1′S,2′S,3′R,4′R,5′S-tetrahydroxycyclopentyl)-2-(9-methylpentadecanoyl)-3-(10-methyl-hexadecanyl)-sn-glycerol Examples of glycoglycerolipids having ionic groups (such as phosphate, sulfate, and sulfonate) obtainable according to the invention from lipoid phases are:

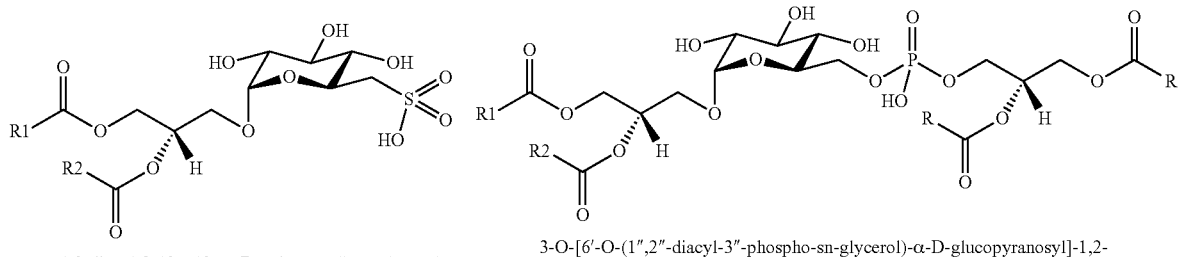

1,2-diacyl-3-(6-sulfo-α-D-quinovosyl)-sn-glycerol

3-O-[6'-O-(1'',2''-diacyl-3''-phospho-sn-glycerol)-α-D-glucopyranosyl]-1,2-diacyl-sn-glycerol

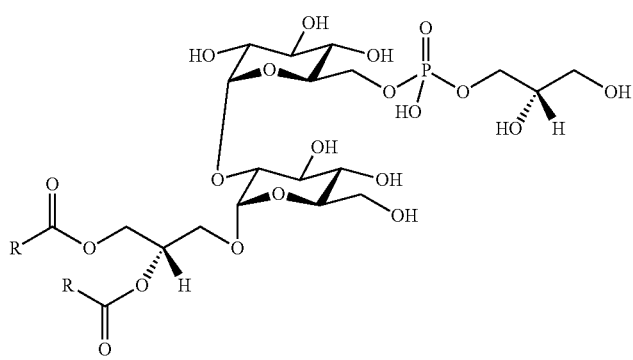

1,2-diacyl-3-[6''-(sn-glycero-1-phospho-)-α-D-kojibiosyl]-sn-glycerol

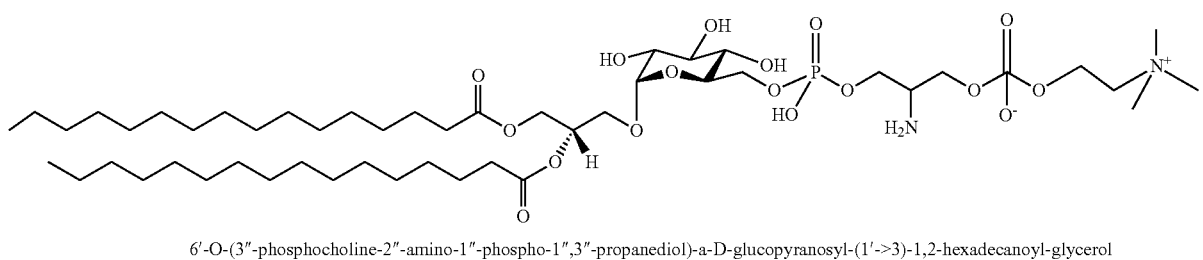

6'-O-(3''-phosphocholine-2''-amino-1''-phospho-1''',3'''-propanediol)-a-D-glucopyranosyl-(1'->3)-1,2-hexadecanoyl-glycerol

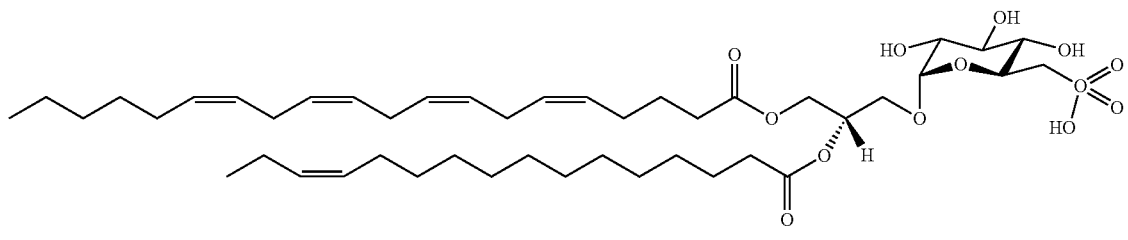

1-(5Z,8Z,11Z,14Z-eicosatetraenoyl)-2-(13Z-hexadecenoyl)-3-(6'-sulfo-α-D-quinovosyl)-sn-glycerol

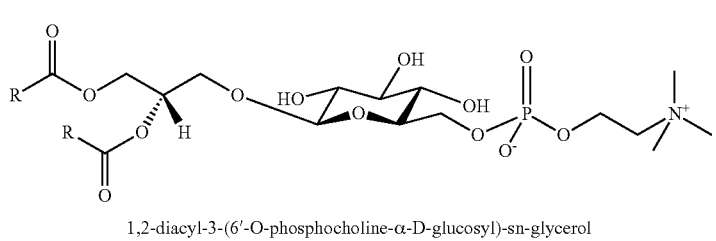

1,2-diacyl-3-(6'-O-phosphocholine-α-D-glucosyl)-sn-glycerol

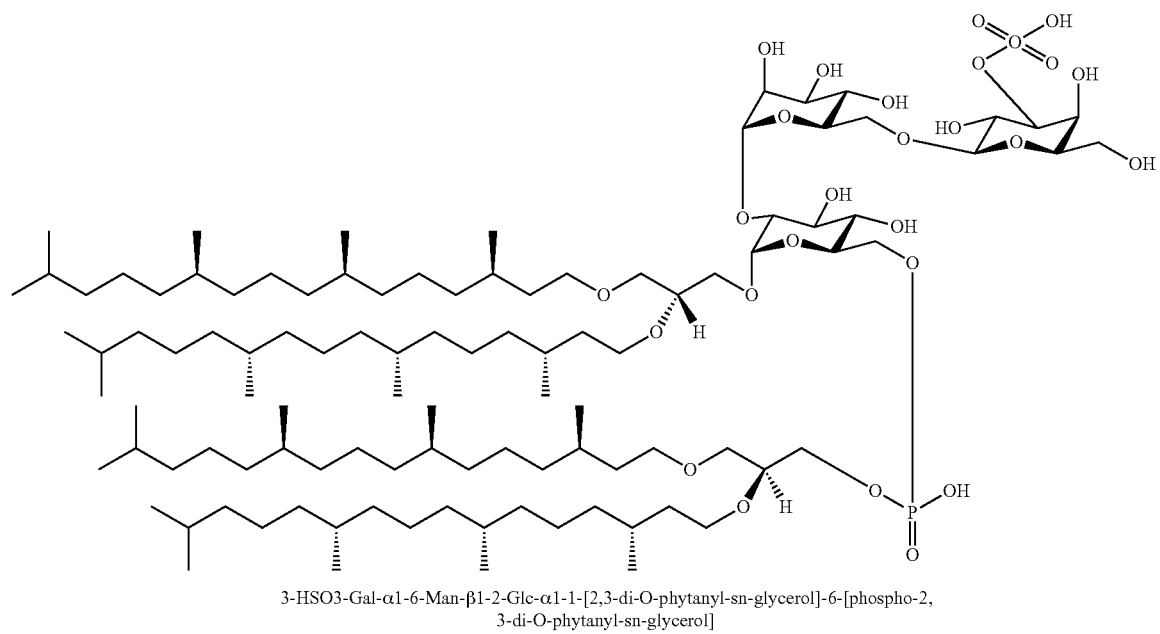
3-HSO3-Gal-α1-6-Man-β1-2-Glc-α1-1-[2,3-di-O-phytanyl-sn-glycerol]-6-[phospho-2,
3-di-O-phytanyl-sn-glycerol]
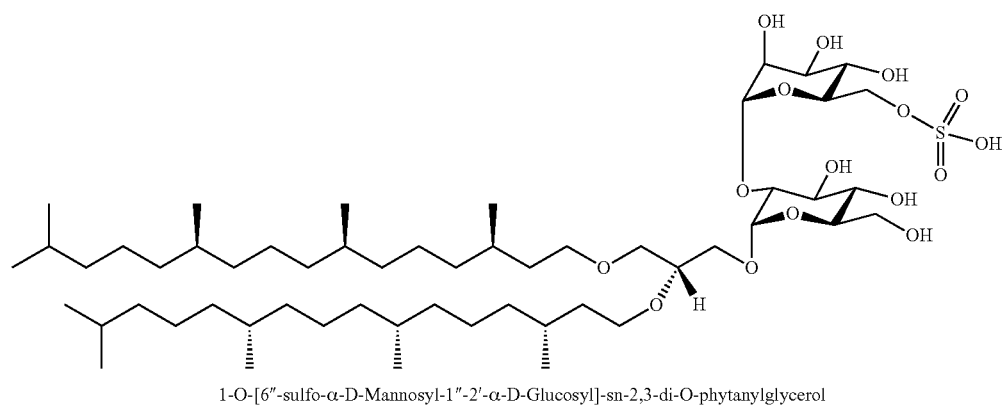
1-O-[6″-sulfo-α-D-Mannosyl-1″-2′-α-D-Glucosyl]-sn-2,3-di-O-phytanylglycerol
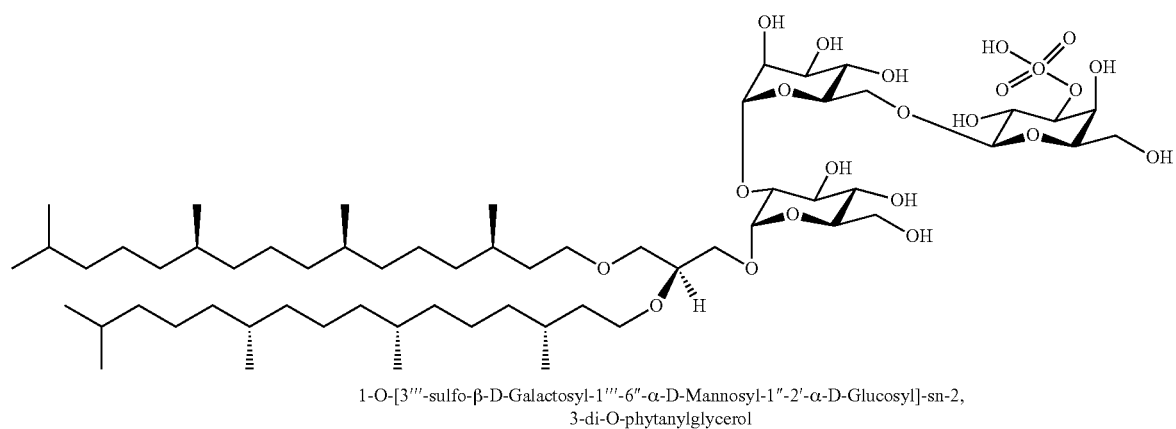
1-O-[3‴-sulfo-β-D-Galactosyl-1‴-6″-α-D-Mannosyl-1″-2′-α-D-Glucosyl]-sn-2,
3-di-O-phytanylglycerol -continued

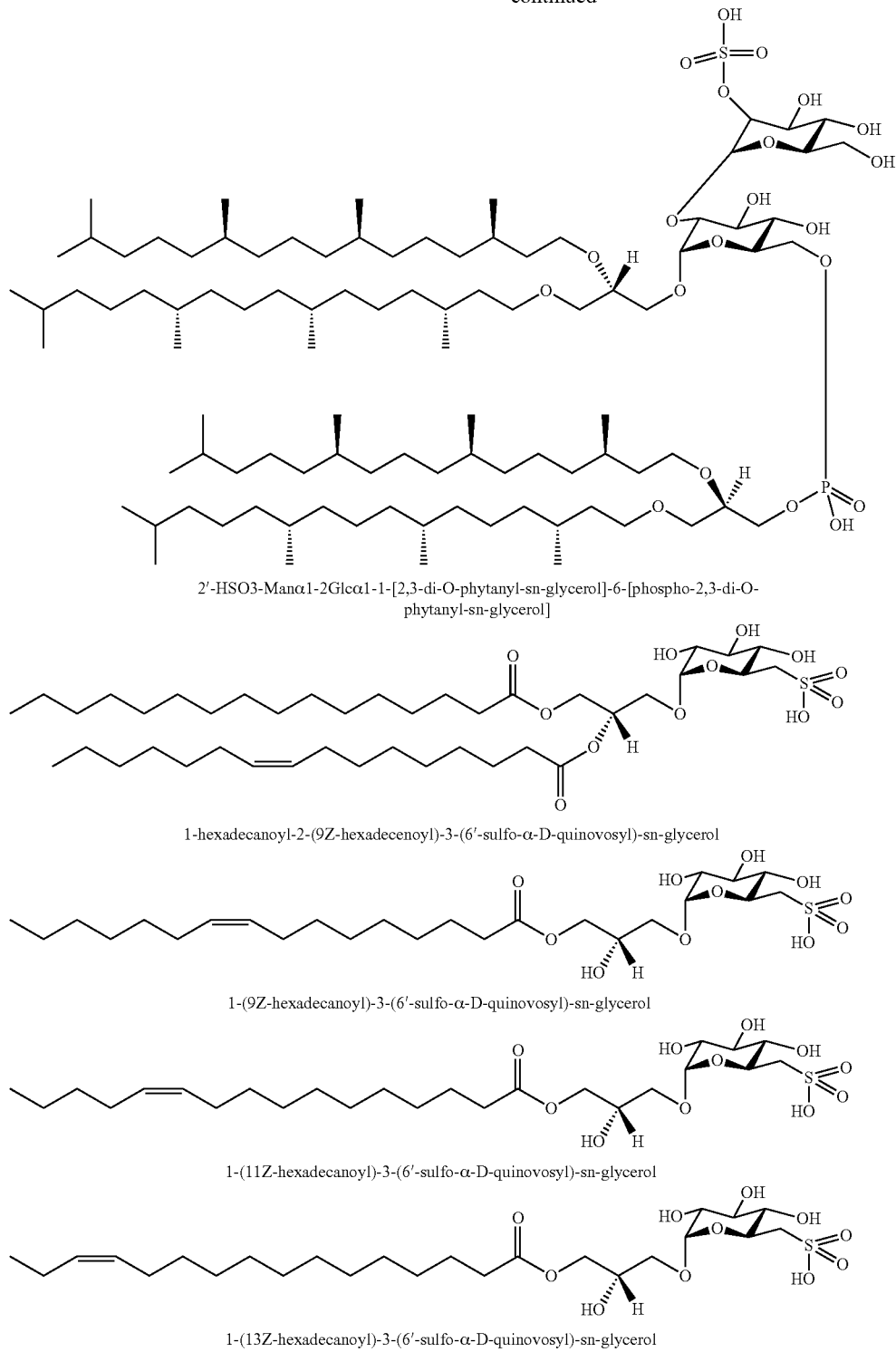

The aforementioned compounds are examples of glycoglycerolipids which are contained in the lipoid phase. According to the invention, glycoglycerolipids without ionic groups are preferably obtained from the lipoid phase. The term lipoid phase therefore designates the starting material or an educt which is treated according to steps A1), B1), C1), and D1) or according to steps A1), A2), B1), C1), and D1) or according to steps A1), A2'), B1), C1), and D1). This results in an aqueous phase which is also referred to as a separated aqueous phase from which the separated glycoglycerolipids and, if present in the lipoid phases, the glycosphingolipids, glycolipids, and/or glycophospholipids can be obtained according to step D2). This recovering of a hydrolysis-poor fraction of glycoglycerolipids and glycosphingolipids is preferably carried out by extraction from the aqueous phase obtained according to steps D1) or D2) with solvents such as, e.g., chloroform, methylene chloride and/or methanol. In addition, a glycoglycerolipid-poor lipid phase is obtained, which also has low contents of potassium, iron, calcium, and, if present of glycolipids due to treatment with the steps A1), B1), C1), and D1) optionally combined with step A2) or A2'). The term "glycoglycerolipid-poor" lipid phase is referred to the lipid phase obtained immediately after step D1). This lipid glycyclerolipid-poor phase is already a refined lipid phase and can then be further purified after step E1) in order to obtain a highly refined lipid glycoglycerolipid-poor phase. The highly refined lipid glycoglycerolipid-poor phase obtained after step E1) is referred to as a glycoglycerolipid- and carboxylic acid-poor lipid phase or for better differentiation from the glycoglycerolipid-poor lipid phase obtained after step D1), a further purified glycoglycerolipid-poor lipid phase.

The present invention therefore also relates to glycoglycerolipid- and carboxylic acid-poor lipid phases consisting of at least 90 wt % from a mixture of triacylglycerides, diacylglycerides, and monoacylglycerides with a content of K<5 ppm, P<5 ppm, preferably P<4 ppm, more preferably P<3 ppm, more preferably P<2 ppm, and more preferably P<1 ppm, Fe<5 ppm, preferably Fe<4 ppm, more preferably Fe<3 ppm, more preferably Fe<2 ppm, more preferably Fe<1 ppm, and more preferably Fe<0.1 ppm, Ca<5 ppm, and free fatty acids <0.30 wt %, preferred <26 wt %, more preferably <0.23 wt %, further preferred <0.21 wt %, further preferred <19 wt %, further preferred <17 wt %, further preferred <15 wt % and in particular preferred <0.13 wt %.

The present invention furthermore relates to a lipid glycoglycerolipid and/or carboxylic acid-poor phase, preferably consisting of at least 90% by weight of acylglycerides, that means a mixture of triacylglycerides, diacylglycerides and monoacylglycerides, with contents of P<0.8 mg/kg, preferably P<0.7 mg/kg, preferably P<0.6 mg/kg, preferably Fe<0.015 mg/kg, preferably Fe<0.15 mg/kg, preferably Fe<0.013 mg/kg, preferably Fe<0.011 mg/kg, preferably Fe<0.009 mg/kg, Ca<0.5 mg/kg, preferably Ca<0.4 mg/kg, preferably Mg<0.12 mg/kg, preferably Mg<0.11 mg/kg, preferably Mg<0.10 mg/kg, Cr<0.01 mg/kg, preferably Cr<0.009 mg/kg, preferably Cr<0.008 mg/kg, preferably Cr<0.007, Zn<0.01 mg/kg, preferably Zn<0.009 mg/kg, Zn<0.008 mg/kg, preferably Zn<0.007 mg/kg, Mn<0.005 mg/kg, preferably Mn<0.004 mg/kg, preferably Mn<0.003 mg/kg, and/or FFA<0.3 wt %, preferably FFA<0.28 wt %, preferably FFA<0.26%, preferably FFA<0.24 wt %, preferably FFA<0.22 wt %, preferably FFA<0.20 wt %.

Furthermore, the present invention relates to lipid glycoglycerolipid-poor phases consisting of at least 90 wt % of acyl glycerides with contents of P<1 ppm, Fe<0.04 ppm, Ca<0.4 ppm, Mg<0.1 ppm, Pb<0.02 ppm, Cu<0.02 ppm, Cr<0.02 ppm, Ni<0.02 ppm, Cd<0.02 ppm, Zn<0.02 ppm and FFA<0.3 wt. %.

The lipid glycoglycerolipid-poor phases according to the invention can be even prepared from qualitatively poor starting materials, i.e. lipid phases. Lipid phases with a poor quality may contain up to 50 wt % of free fatty acids and amounts of K between 50 and 500 ppm, P between 100 and 1,500 ppm, Fe between 50 and 500 ppm, and Ca between 50 and 500 ppm, respectively.

The term "fatty acids" is used synonymously with the term "free fatty acids". The addition "free" is intended to make clear that these are unbound fatty acids, since the majority of the components in the lipid phase contains bounded fatty acids. Aliphatic monocarboxylic acids having at least 8 carbon atoms are denoted as fatty acids.

Acids having at least one carboxylate group are referred to as "carboxylic acids". Thus, carboxylic acids also comprise fatty acids.

The term "lipid phase" as used herein comprises mixtures of substances of biological origin, which can be obtained from plants, algae, animals, and/or microorganisms and have a water content of <10 wt % and a content of lipophilic substances comprising monoacylglycerides, diacylglycerides, and/or triacylglycerides of a total of >70 wt %, or >75 wt %, or >80 wt %, or >85 wt %, or >90 wt %, or >95 wt %. For example, the lipid phases can be extracts of oleaginous plants such as kernels of rape, soya, camelina, jatropha, palm, but also of algae and microorganisms, as well as animal fats and oils.

The lipid phases preferably have a water content of <10% and a content of alkanes and/or cyclic aromatics and/or mono-/di-/triglycerides (acylglycerides) of >75 wt %. It is irrelevant whether the lipid phase is a suspension, emulsion, or colloidal liquid.

If the lipid phases are extracts or extraction phases of lipid substances from a separation or extraction carried out beforehand, the lipid phase may also consist of >50% organic solvents or hydrocarbon compounds.

The term "lipid phase containing glycoglycerolipids and acylglycerides" only states that the lipid phases which can be used, in addition to several other substances, also contain glycoglycerolipids and acylglycerides, but are in no way only composed of glycoglycerolipids and acylglycerides. The same applies to the term "lipid phase which contains glycoglycerolipids and glycosphingolipids and acylglycerides". In addition, this term only means that the lipid phases which can be used according to the invention contain glycoglycerolipids and glycosphingolipids and acylglycerides but are in no way only composed of glycoglycerolipids and glycosphingolipids and acylglycerides. Some exemplary substances or substance classes which may also be present in the lipid phases that can be used are, for example, glycolipids other than glycoglycerolipids and glycosphingolipids, glycophospholipids, phospholipids, free fatty acids, fatty acid esters, sterylglycosides and many other substances.

The main constituent of the lipid phase is represented by acylglycerides, apart from organic solvents eventually used for their extraction. Acylglycerides are not transferred into the aqueous phase or only to a very small extent, i.e. <0.1 wt %, preferably <0.05 wt %, and most preferably <0.01 wt % of all acylglycerides of the lipid phase, by use of the processes according to the invention. In so far, they do not exist in the aqueous phase containing glycoglycerolipids and glycosphingolipids or only to a very small extent.

Being a natural component of virtually all cells of plant and animals, phospholipids, glycolipids, along with glycoglycerolipids and glycosphingolipids are also inevitably present in lipid phases (such as vegetable oils or animal fats) that derive from these animals or plants. The extent to which this is actually the case depends not only on the source of the extraction material, but also on the extraction method. Table 1 summarizes compositions of lipid phases obtained from various crops. It can already be seen here that, as a rule, the neutral lipids form the main part of the lipid phases, but the proportion of phospholipids and glycolipids/glycoglycerolipids/glycosphingolipids is variable. For example, the proportion of glycolipids, glycoglycerolipids and glycosphingolipids ranges from 0.2 wt % in coconut oil, approximately 2 wt % in borage oil, and 6.3-7 wt % in rice bran oil to 19.4 wt % in avocado oil.

Table 1: Content of lipids without ionic groups (NL), acylglycerides (AG), phospholipids (PL), and glycolipids together with glycoglycerolipids and glycosphingolipids (GL) in the seeds (S) and the oils obtained therefrom. The content of AG, PL, and GL is expressed as a percentage of the total oil. In the case of seeds, in addition to the percentage of the oil (total), the relation to the seed mass is given.

| Source | Oil | S | total | NL | PL | GL |
|---|---|---|---|---|---|---|
| Soja: *Glycine soya* | X | | | 88 | 10 | 2 |
| Palm: *Elaieis guineensis* | X | | | 96 | 2.4 | 1.4 |
| Rice bran: *Oryza sativa* | | X | 21.9-23.0 | 88.1-89.2 | 4.5-4.9 | 6.3-7.0 |
| Corn *Zea mays* | X | | | 96.8-97.5 | 0.8-0.95 | 1.5-1.66 |
| Rapeseed | | X | | 95.8 | 3.2 | 0.9 |
| *Brassica napus* | | | | 95.5 | 3.6 | 0.9 |
| Rape - Variant "Golden": *Brassica* | X | | 34.8 | 98.8 | 3.0 | |
| Rape - Variant "Zero Eruca": *Brassica* | X | | 35.9 | 98.1 | 1.8 | |
| Sunflower seed: *Helianthus annuus* | X | | | <4 | | |
| Jatropha: *Jatropha curcus* | X | | 32 | 97.6 | 1.45 | 0.95 |
| Coconut *Cocos nucifera* | X | | | 93.6-98.2 | 0.03-0.4 | 0.2-0.35 |
| Cacaobutter | X | | | 98.75 | 0.037 | 0.89 |
| Safflower: *Carthamus tinctorius* | X | | | 94 | 1.2 | 4.5 |
| Borage: *Borago officinalis* | | X | 34.0 | 95.7 | 2.3 | 2.0 |
| Crambe: *Crambe abyssinica* | | X | 32.2 | 98.5 | 1.1 | |
| Crambe: *Crambe abyssinica* | X | | 75 | 88.6 | 11 | — |
| Black cumin: *Nigella sativa* | X | | | 97.2 | 0.3 | 2.18 |
| Corianderoil: *Coriandrum sativum* | X | | | 96.0 | 0.85 | 2.39 |
| Nigerseed: *Guizotia abyssinca* | X | | | 97.0 | 0.28 | 1.90 |
| Nalta jute: *Corchorus olitorius* | X | | | 93.2 | 1.9 | 3.7 |
| Hibiscus: *Hibiscus sabdariffa* | X | | | 94.1 | 2.1 | 2.6 |
| Avocado: *Persea americana* | | X | 10.8 | 60.2 | 20.4 | 19.4 |
| African star apple: *Chrysophyllum albidum* | | X | 7.7 | 546 | 23.4 | 22 |
| Bitter melon: *Mormodica charantia* | X | | | 86.8-91.1 | 3.22-4.62 | 4.37-7.43 |
| Sesame: *Sesamum indicum* | X | | 42.5-46.2 | 91.7-93.3 | 0.08-0.1 | 5.6-5.8 |
| Mexican prickly poppy: *Argemone mexicana* | X | | 35 | 92.1-92.3 | 1.5-1.7 | 5.5-5.8 |
| Shiso: *Perilla frutescens* | | X | 38.6-47.8 | 91.2-93.9 | 2.0-3.0 | 3.5-5.8 |
| Mango: *Mangifera indica* | | X | 7.1-10 | 58.5-96.8 | 0.11-0.8 | 0.6-1.2 |
| Narrowleaf lupin: *Lupinus angustifolius* | | X | 8.6 | 76.3 | 14.9 | 3.5 |
| Paprica: *Capsicum annum* | | X | 37.5 | 82 | 11.9 | 6.1 |
| | | | 26.4 | 82 | 13.2 | 4.8 |
| Guinea-pepper: *Atremomum melequeta* | | X | | 67.72 | 13.68 | 3.75 |
| | | | | 50 | 10.12 | 2.38 |

Although above-mentioned fatty acid glycosides comprising trehalose lipids, mannosylerythritol lipids, cellobiose lipids, rhamnolipids, and sophorolipids are not synthesized from animals or plants, but from bacteria, fungi, and yeasts, and thus are not appear as natural component in plant or animal oils, hydrocarbon sources are needed for the generation of these emulsifiers. A significant disadvantage of emulsifiers of natural origin (bio-emulsifiers) compared to industrially synthesized emulsifiers is the higher production costs. In biotechnology, large scale production of bio-emulsifiers is based on hydrocarbon sources such as vegetable oils (e.g. sunflower oil, rapeseed oil, palm oil, jatropha oil, castor oil) and waste products (e.g. press cakes of coconut, soy, peanut, or soap stock rape press cake). Likewise, waste products from the production of animal foods (e.g. tallow, fish oils, and whey) can be used as a low-cost source of hydrocarbons. Thus, lipid phases are formed which, in addition to vegetable oils or animal oils, also contain bio-emulsifiers from the group of glycolipids formed by microorganisms.

Since approx. 60% of the production costs for bio-emulsifiers produced by microorganisms arise from the purification processes thereof, there is a need of an efficient and cost-effective process for separation and purification of glycolipids such as trehalose lipid, mannosylerythritol lipids, cellobiose lipids, rhamnolipids, and sophorolipids from lipoid phases.

The lipoid phases in the sense of the definition used herein include, inter alia, acai oil, acrocomia oil, almond oil, babassu oil, currant seed oil, borage seed oil, rapeseed oil, cashew oil, castor oil, coconut oil, coriander oil, corn oil, cottonseed oil, stinging oil, linseed oil, grape seed oil, hazelnut oil, other nut oils, hemp seed oil, jatropha oil, jojoba oil, macadamia nut oil, manganese oil, meadowscreen oil, mustard oil, claw oil, olive oil, palm oil, palm kernel oil, palm olein oil, peanut oil, pecan oil, pine kernel oil, pistachio oil, poppy oil, rice sprout oil, thistle oil, *camellia* oil, sesame oil, shea butter oil, soybean oil, sunflower oil, tall oil, tsubaki oil, walnut oil, varieties of "natural" oils with altered fatty acid compositions via genetically modified organisms (GMOs) or traditional breeds, neo-chloris *oleoabundans* oil, *scenedesmus dimorphus* oil, *euglena gracilis* oil, *phaeodactylum tricornutum* oil, *pleurochrysis carotene* oil, *prymium parvum* oil, *tetraselmis chui* oil, *tetraselmis suecica* oil, *isochrysis galbana* oil, *nannochloropsis salina* oil, *botryococcus brownii* oil, *dunaliella tertiolecta* oil, nannochloris oil, *spirulina* oil, chlorophyceae oil, bacilliarophyta oil, a mixture of the previous oils as well animal oils (especially marine animals) and biodiesel.

The lipid phases that are provided at the beginning of the process according to the invention for separating of glycoglycerolipids, and, if present, in the lipid phase of glycosphingolipids, glycolipids, and/or glycophospholipids can also be referred to as a lipid crude phase. Still, this phase may also high content of accompanying substances such as metal ions, ionic lipids, fatty acids, and possibly other substances (e.g., herbicides, essential oils). Of course, the composition of the crude lipid phase changes during the course of the aqueous extraction step(s) according to the invention. Consequently, the lipid phases remaining after each aqueous extraction step have a different composition from the corresponding initial phase because substances which pass from the lipid phase into the aqueous phase during the aqueous extraction are separated off together with this aqueous phase. In addition to the glycoglycerolipids, possibly together with glycosphingolipids, glycolipids, and/or glycophospholipids (if present), other compounds especially metal ions, ionic lipids, and/or free fatty acids are also removed from the lipid phase by a process according to the invention. This reduction does not necessarily have to be achieved to a major extent in step D1), but preferably also are accomplished in step A2) and A2'), and in particular also in step E1).

The aqueous phase obtained according to the invention, containing the glycoglycerolipids or the glycoglycerolipids and glycosphingolipids, can be further separated. According to the invention, aqueous phases containing glycoglycerolipids and possibly glycosphingolipids are preferably obtained that account for a solids content of preferably >40 wt %.

It was shown that direct extraction of the lipophilic solid constituents from the obtained aqueous extraction medium by means of organic solvents is possible. Thus, most of the glycoglycerolipids and glycosphingolipids dissolved in the water phase can be directly separated, e.g. by chloroform. The separation result can be further improved by the addition of a small portion of methanol to achieve a transparent organic and aqueous phase. A basically equal result is obtained when the water phase is first removed under mild conditions and then the solid is dissolved in $CHCl_3$, $CHCl_3$/MeOH, or acetone. The compounds can be separated and recovered in further fractions by means of established methods such as thin-layer chromatography.

The term "fatty acids" as used herein refers to free fatty acids (also abbreviated FFAs), so fatty acids which are free and non-glyceridic (i.e. to glycerol) or glycosidic (i.e. to sugar residues) bound.

The term "fatty acids" preferably comprises the following compounds: hexanoic acid, octanoic acid, decanoic acid, dodecanoic acid, tetradecanoic acid, hexadecanoic acid, heptadecanoic acid, octadecanoic acid, eicosanoic acid, docosanoic acid, tetracosanoic acid, cis-9-tetradecenoic acid, cis-9-hexadecenoic acid, cis-6-octadecenoic acid, cis-9-octadecenoic acid, cis-11-octadecenoic acid, cis-9-eicosenoic acid, cis-11-eicosenoic acid, cis-13-docosenoic acid, cis-15-tetracosenoic acid, t9-octadecenoic acid, t11-octalecenoic acid, t3-hexadecenoic acid, 9,12-octadecadienoic acid, 6,9,12-octadecatrienoic acid, 8,11,14-eicosatrienoic acid, 5,8,11,14-eicosatetraenoic acid, 7,10,13,16-docosatetraenoic acid, 4,7,10,13,16 Docosapentaensäure, 8,11,14,17-eicosatetraenoic acid, 5,8,11,14,17-eicosapentaenoic acid, 7,10,13,16,19-docosapentaenoic acid, 4,7,10,13,16,19-docosahexaenoic acid, 5,8,11-eicosatrienoic acid, 9c11t13t-eleostearic acid, 8t10t12c-calendic acid, 9c11t13c-catalpic acid, 4,7,9,11,13,16,19-docosaheptadecanoic acid, taxoleic acid, pinolenic acid, sciadoic acid, 6-octadecinoic acid, t11-octadecene-9-inoic acid, 9-octadecinoic acid, 6-octadecene-9-inoic acid, t10-heptadecene-8-inoic acid, 9-octadecene-12-inoic acid, t7,t11-octalecadien-9-ionic acid, t8,t10-octadecadienoic-12-inoic acid, 5,8,11,14-eicosatetrainoic acid, retinoic acid, isopalmitic acid, pristanic acid, phytanic acid, 11,12-methylene octadecanoic acid, 9,10-methylenehexadecanoic acid, coronaric acid, (R,S)-lipoic acid, (S)-lipoic acid, (R)-lipoic acid, 2,4-bis (methylsulfonyl)-butanoic acid, 1,2-dithiolane carboxylic acid, (R,S)-6,8-dithian-octanoic acid, tariric, santalbic acid, stearic acid, 6,9-octalecenoic acid, pyrulic acid, crepenic acid, heisteric acid, t8,t10-octadecadien-12-inoic acid, ETYA, cerebronic acid, hydroxynervic acid, ricinoleic acid, lesquerolic acid, brassylic acid, and thapsic acid.

The term "acylglycerides" as used herein describes compounds wherein at least one hydroxyl group of a glycerol moiety is esterified with a fatty acid. The acylglycerides include the monoacylglycerides in which a hydroxyl group of the glycerol is esterified with a fatty acid, the diacylglycerides in which two hydroxyl groups of the glycerol are esterified with a fatty acid, and the triacylglycerides in which all three hydroxyl groups of the glycerol are esterified each with a fatty acid.

The term "glycolipid", as used herein, encompasses compounds in which one or more monosaccharide residues are linked via a glycosidic bond to a hydrophobic acyl residue.

"Glycoglycerolipids" are compounds in which a saccharide residue is attached to a primary hydroxy group of glycerol and the other two hydroxy groups of the glycerol are esterified with lipophilic acyl residues and in particular fatty acid residues.

"Glycosphingolipids" are compounds wherein a saccharide residue is glycosidically bound to a sphingolipid.

"Glycophosphatidylinositols" are compounds in which saccharides are linked glycosidically to the inositol group of phosphatidylinositol.

"Phospholipids" as understood herein, are amphiphilic lipids containing a phosphate group bound either to a phosphoglyceride or to a phosphosphingolipid. "Phosphoglycerides" (also referred to as glycerophospholipids or phosphoglycerolipids) consist of a diacylglyceride where the remaining terminal hydroxy group is bound to a phosphate residue which is either not further modified (phosphatidic acid) or esterified with an alcohol. The most common representatives of the latter group are phosphatidylcholines (also referred to as lecithins), phosphatidylethanolamines, and phosphatidylserines. The "phosphosphingolipids" include lipids with a sphingosine skeleton, and where the C2-amino group is bound to a fatty acid via an amide bond and whose C1-hydroxy group is linked to a phosphate group via a phospho-ester bond, where (as with the phospholipids) this phosphate group can in turn be esterified with an alcohol. The terms "phospholipids" and "phosphatides" can be used synonymously.

Neutral Glycoglycerolipids

The neutral glycoglycerolipids include glycosyldiacylglycerols, glycosylylalkylglycerols, glycosyldialkylglycerols, and glycoglycerolipids whose saccharide residue is acylated at position 6, 2, and/or 3. In addition, at position 1 or 2 of the glycerol residue there are deacetylated glycoglycerolipids, so-called glycosylmonoacylglycerols. In plants, galactose is the predominant sugar residue in glycoglycerolipids, with prominent examples being monogalactosyldiacylglycerols (MGDG, 1,2-di-O-acyl-3-O-β-D-galactopyranosyl-sn-glycerins) and digalactosyldiacylglycerols (DGDG, 1,2-di-O-acyl-3-O-(6'-O-α-D-galactopyranosyl-(3-D-galactopyranosyl)-sn-glycerols)) and trigalactosyldiacylglycerols and tetragalactosyldiacylglycerols. In most angiosperms, linolenic acid (18:3n−3) is the almost exclusively occurring fatty acid residues at positions 1 and 2 of the glycerol residue of both MGDG and DGDG. In some angiosperms (Solanaceae, Brassicaceae and Chenopodiaceae) and lower plants, however, a special trienoic acid (16:3n−3) frequently occurs at position 2 of the glycerol residue. MGDG and its lyso-forms are of great importance for the baking behavior of wheat flour products and are thus of great industrial interest. In oat grains, so-called DGDG monoestolides could be detected, which contain a linoleic acid as a fatty acid at the glycerol and a linoleic acid hydroxylated at position 15, wherein the hydroxy group at position 15 being esterified with another linoleic acid. Similarly, there are DGDG diestolides, DGDG triestolides, and even DGDG tetraestolides in which the first linoleic acid hydroxylated at position 15 at the glycerol moiety is esterified with one to three other linoleic acids hydroxylated at position 15 before the final esterification with linoleic acid takes place. In addition, plants have glycoglycerolipids with a galactose residue acylated at position 6. Although, as already mentioned, galactose is the predominant sugar residue in plant glycoglycerolipids, there are also glucose-based plant glycoglycerolipids, e.g. 1,2-di-O-acyl-3-O-β-D-glucopyranosyl-sn-glycerol from rice bran. Monogalactosyldiacylglycerols, digalactosyldiacylglycerols, monogalactosylacylalkylglycerols, digalactosylacylalkylglycerols and glucosylylalkylglycerols have also been found in animals.

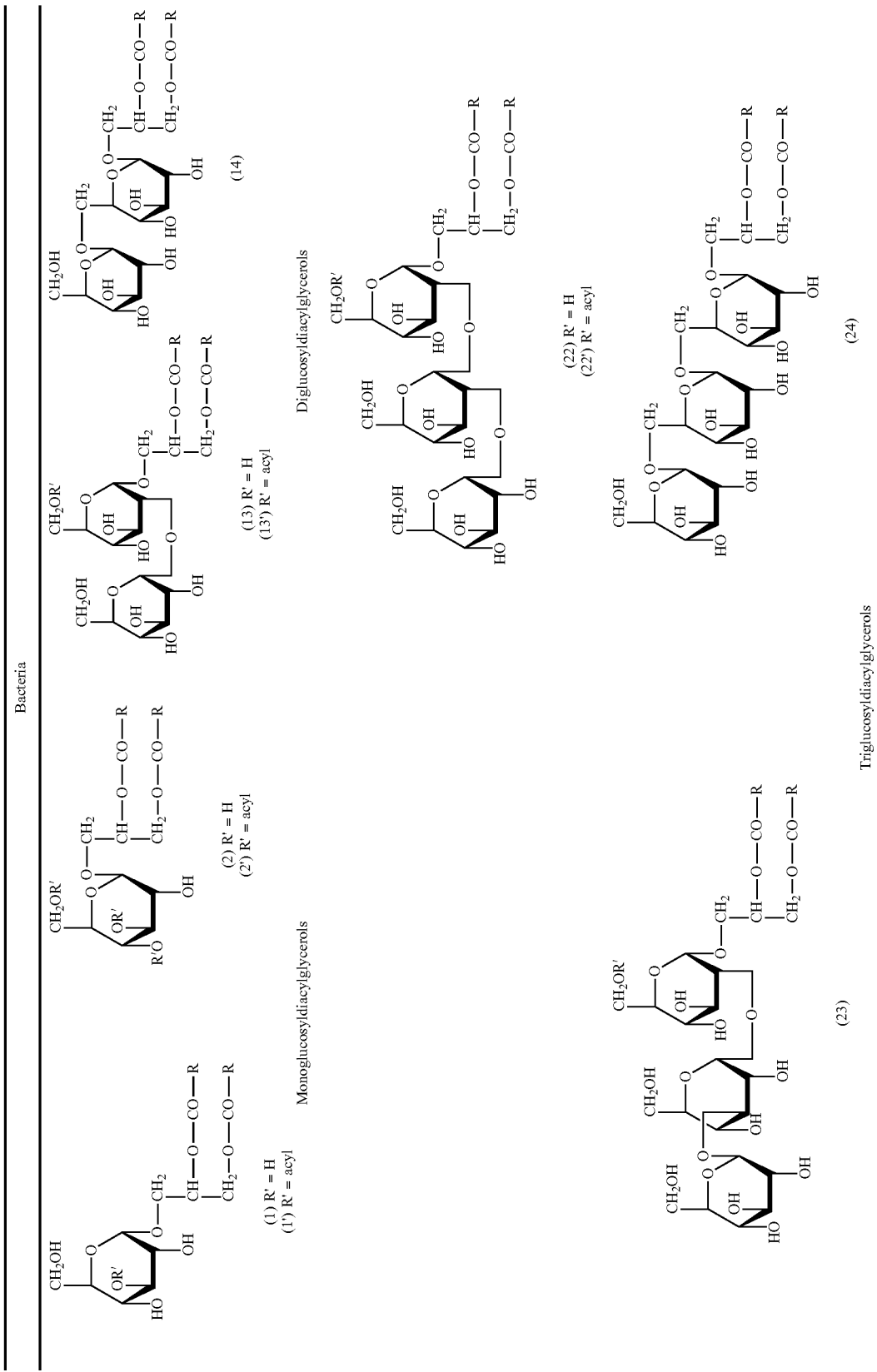

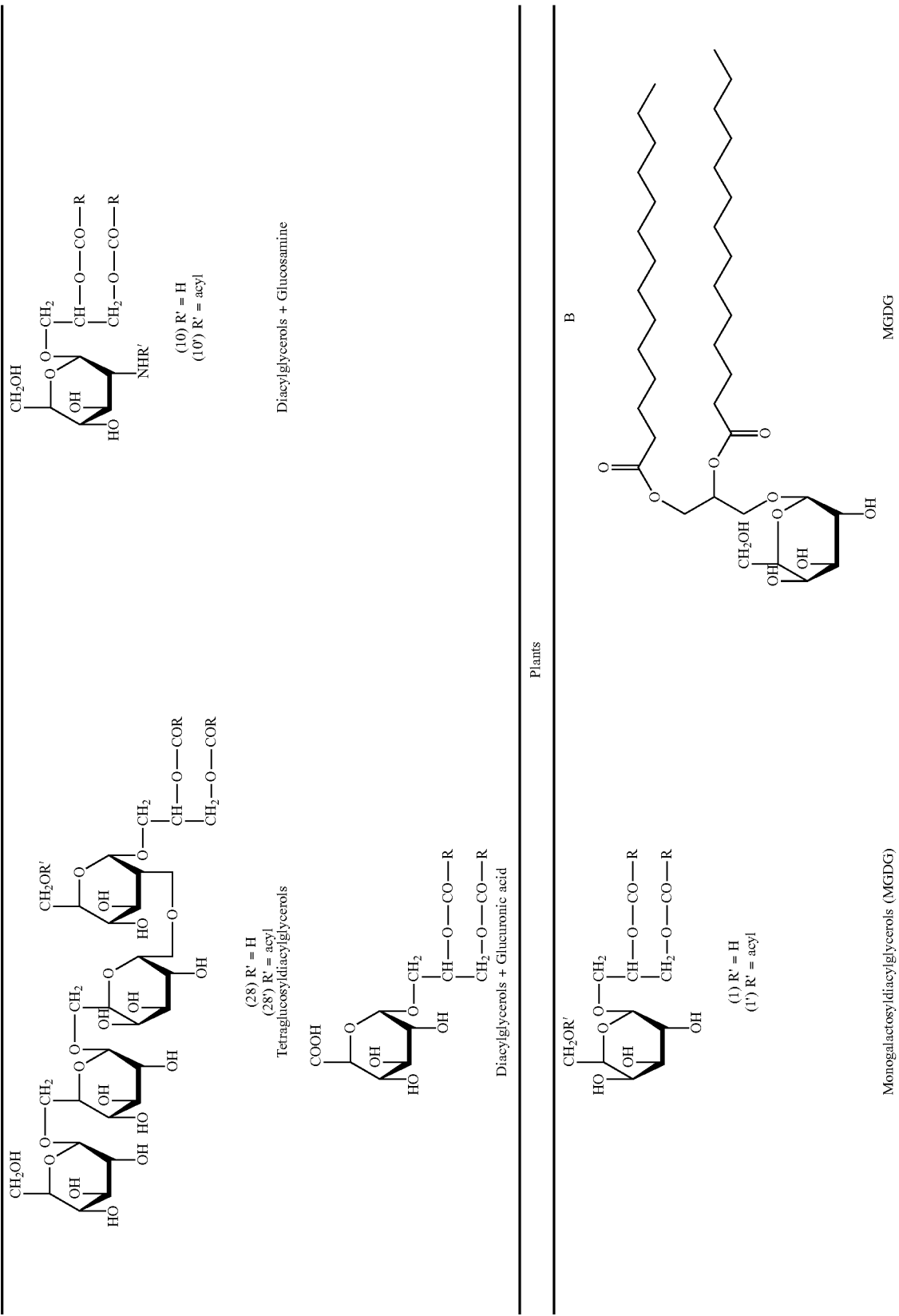

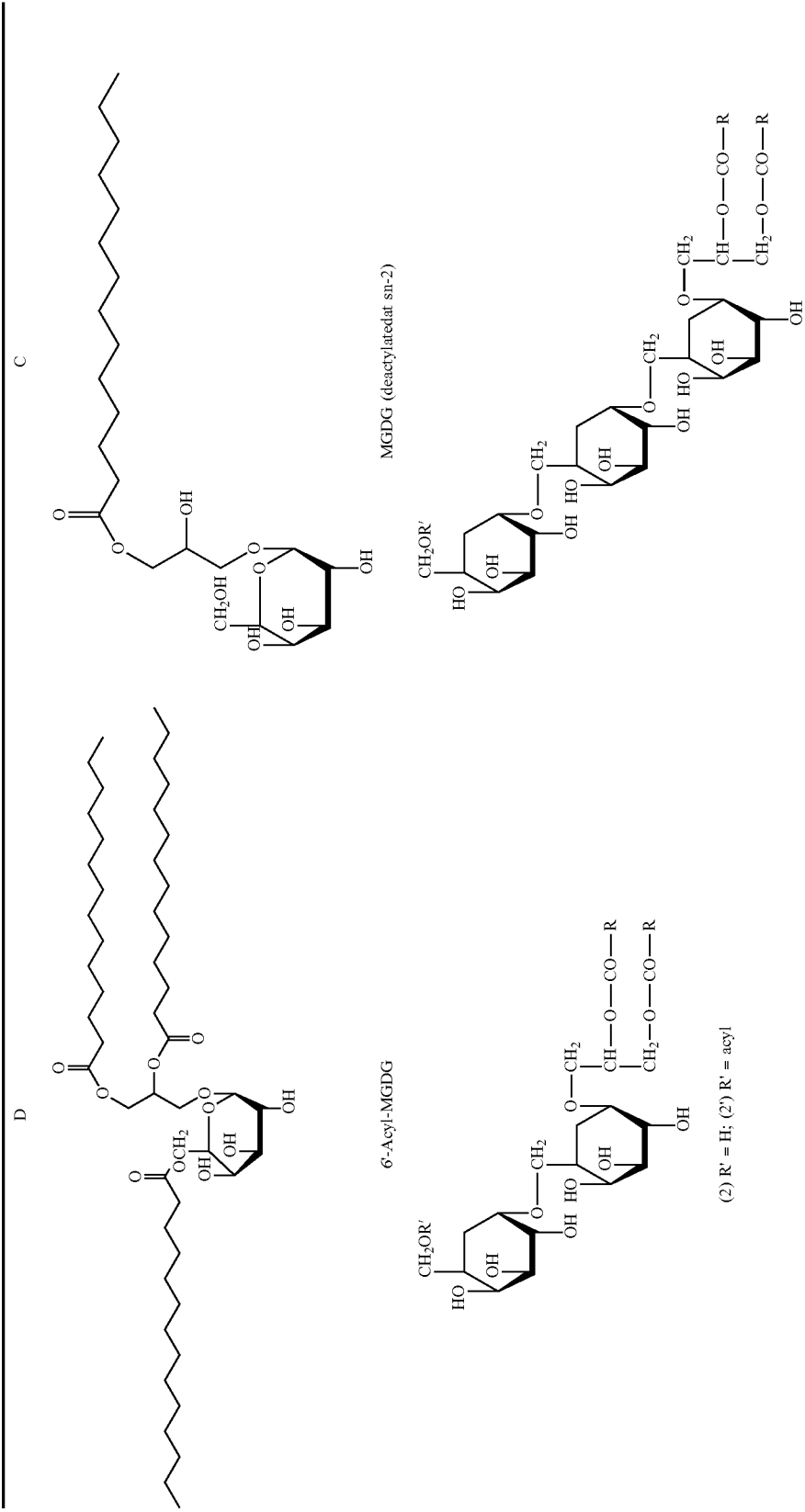

-continued
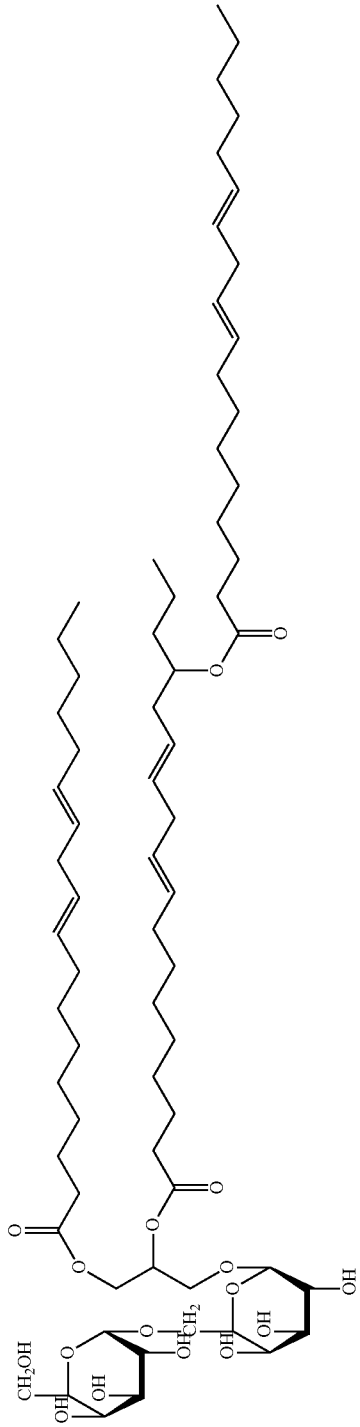
DGDG-Monoestolid
Animals
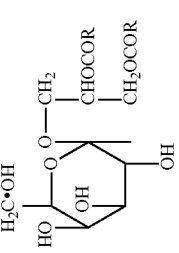
(1)
Monogalactosyldiacylglycerols
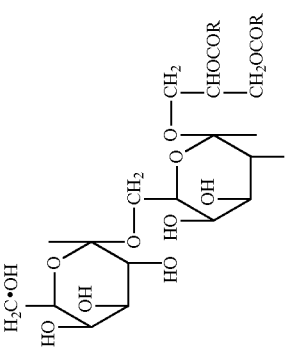
(3)
Digalactosyldiacylglycerols -continued
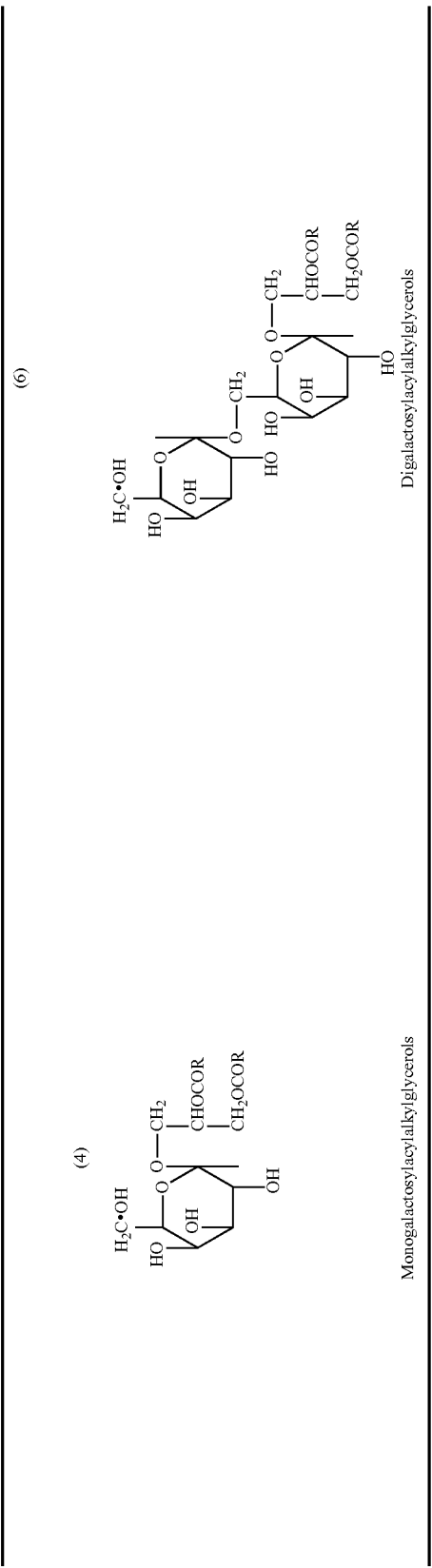

Acidic Glycoglycerolipids

In addition to the neutral glycoglycerolipids, there are also acidic glycoglycerolipids, the acidity of which is due to the fact that their saccharide residue is esterified with sulfuric acid or sulfonic acid, also named sulfoglycoglycerolipids. Examples for this are

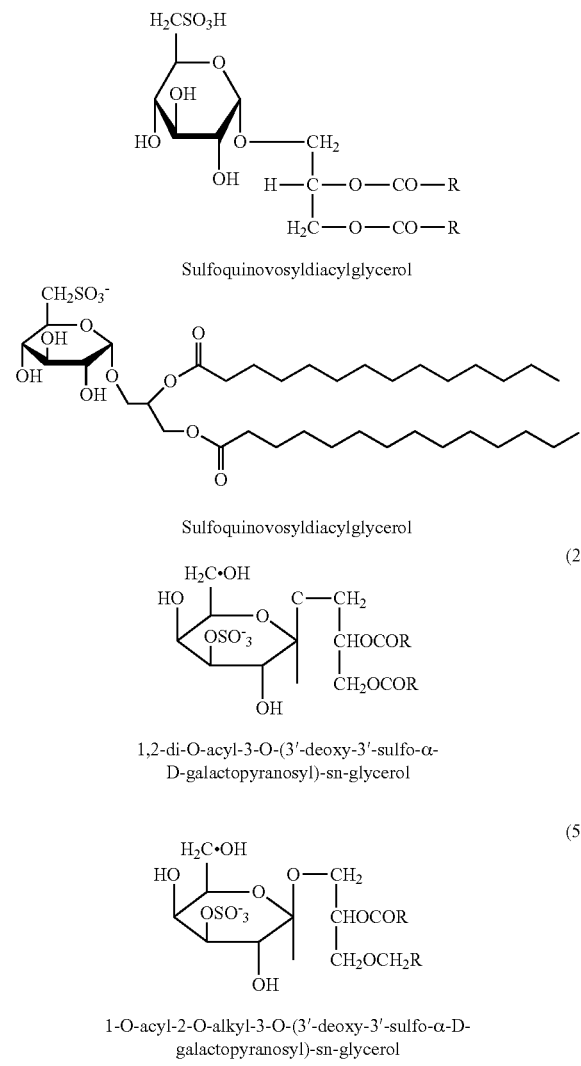

Glycosphingolipids

Glycosphingolipids are glycolipids which contain at least one mono-, oligo-, or polysaccharide residue, which preferentially is linked glycosidically to a sphingoid backbone.

The sphingoid backbone preferably comprises the following amino alcohols: sphingosine (d18:1, also 4-sphingin), dihydrosphingosine (d18:0, also sphinganine), C20 dihydrosphingosine (d20:0, also eicosasphinganine), phytosphingosine (t18:0, also 4-hydroxysphinganine), C20 phytosphingosine (t20:0, also 4-hydroxyeicosasphinganine), dehydrophytosphingosine (t18:1, also 4-hydroxy-8-sphingenin), sphingadienine (d18:2, also 4,8-sphingadienine) as well as their structural analogues.

When the amino group of the sphingoid backbone is linked with a fatty acid, the term "ceramides" is used.

Neutral Glycosphingolipids

I) Mono-, oligo-, and polyglycosylceramides:

Analogous to the abovementioned definitions, glycosylceramides are glycolipids which contain at least one mono-, oligo-, or polysaccharide residue, which is glycosidically linked to a ceramide. The monoglycosylceramides are also referred to as "cerebroside".

The most common monoglycosylceramides in vertebrate animals are the galactocerebrosides in which a galactose residue is linked glycosidically to a sphingoid backbone of sphingosine or dihydrosphingosine, which is linked to its amino group with a non-hydroxylated fatty acid or fatty acid hydroxylated at the position 2 with a chain length of 20 to 24 carbon atoms. It was also possible to detect glucocerebroinsides, which contain glucose as the saccharide residue instead of galactose, in vertebrates (especially in blood and spleen). In plants, in comparison to the galactocerebrosides which are also present, there are mainly cerebrosides which have glucose as a saccharide residue. These are preferably glucocerebroinsides whose sphingoid backbone consists of phytosphingosine and have a fatty acid hydroxylated at position 2 (saturated or monounsaturated) having a chain length of 16 to 24 carbon atoms. Glucocerebrosides with 4,8-sphingadienin as a sphingoid backbone were detected in lipid phases extracted from soybeans or almonds. Glucocerebrosides with dehydrophytosphingosine as a sphingoid backbone and hydroxylated fatty acids of variable length were detected in spurge plants.

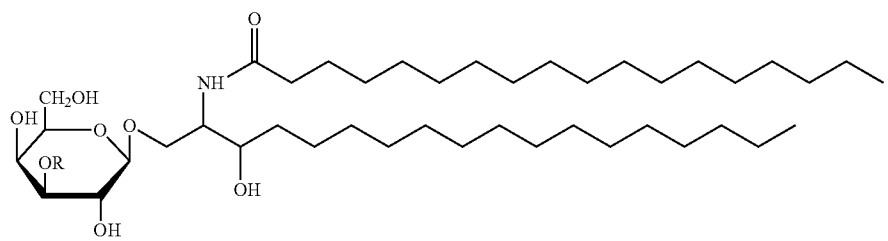

Galactocerebroside (R=H) with ceramide from dihydrosphingosine backbone and stearic acid In addition to the monoglycosylceramides, there are also a large number of higher glycosylated glycosylceramides. The neutral oligoglycosylceramides include digalactosylceramides, lactosylceramides, triglycosylceramides (formerly referred to as globotriaosylceramides), and tetraglycosylceramides which occur in animal as well as in plant tissues. The tetraglycosylceramides include human N-acetylgalactosaminyl-galactosyl-galactosyl-glucosylceramide.

A selection of animal neutral glycosphingolipids (mono-, oligo-, and polyglycosylceramides) is shown in Table 2.

TABLE 2

List of neutral glycosphingolipids in mammals (Source: Glycoscience III: Chemistry and Chemical Biology) Reiner, B.; Tatsuta, K; Thiem, J. (Ed.), Springer Verlag, 2001, ISBN 3-540-67765-8).

| Structure | Trivial name | Symbol[1] | Abbreviation |
|---|---|---|---|
| Glcβ1 → 1Cer | Glucoxylceramide | GlcCer | — |
| Galβ1 → 4Glcβ1 → Cer | Lactosylceramide | LacCer | — |
| GalNAcβ1 → 3Galβ1 → 4Glcβ1 → 1Cer | Gangliotriaosylceramide | GgOse$_3$Cer | Gg3 |
| Galβ1 → 4GalNAcβ1 → 4Galβ1 → 4Glcβ1 → 1Cer | Gangliotetraosylceramide | GgOse$_4$Cer | Gg4 |
| GalNAcβ1 → 4Galβ1 → 3GalNAcβ1 → 4Galβ1 → 4Glcβ1 → 1Cer | Gangliopentaosylceramide | GgOse$_5$Cer | Gg5 |
| Galα1 → 4Galβ1 → 4Glcβ1 → 1Cer | Globotriaosylceramide | GbOse$_3$Cer | Gb3 |
| GalNAcβ1 → 3Galα1 → 4Galβ1 → 4Glcβ1 → 1Cer | Globotetraosylceramide | GbOse$_4$Cer | Gb4 |
| GalNAcβ1 → 3GalNAcβ1 → 3Galα1 → 4Galβ1 → 4Glcβ1 → 1Cer | Globopentaosylceramide | GbOse$_5$Cer | Gb5 |
| GalNAcα1 → 3GalNAcβ1 → 3Galα1 → 4Galβ1 → 4Glcβ1 → 1Cer | Forsman GSL | — | — |
| GlcNAcβ1 → 3Galβ1 → 4Glcβ1 → 1Cer | Lactotriarosylceramide | LcOse$_3$Cer | Lc3 |
| Galβ1 → 3GlcNAcβ1 → 3Galβ1 → 4Glcβ1 → 1Cer | Lactotetraosylceramide | LcOse$_4$Cer | Lc4 |
| Galβ1 → 4GlcNAcβ1 → 3Galβ1 → 4Glcβ1 → 1Cer | Neolactotetraosylceramide | nLcOse$_4$Cer | nLc4 |
| Galβ1 → 4GlcNAcβ1 → 3Galβ1 → 4GlcNAcβ1 → 3Galβ1 → 4Glcβ1 → 1Cer | Neolactohexaosylceramide | nLcOse$_6$Cer | nLc6 |
| Galβ1 → 4GlcNAcβ1 → 3Galβ1 → 4GlcNAcβ1 → 3Galβ1 → 4GlcNAcβ1 → 3Galβ1 → 4Glcβ1 → 1Cer | Neolactooctaosylceramide | nLcOse$_8$Cer | nLc8 |

Animals
Globotetraosylceramide having ceramide based on dihydrosphingosine-backbone and stearic acid
Lactotetraosylceramide having ceramide based on dihydroshingosine-backbone and stearic acid

C

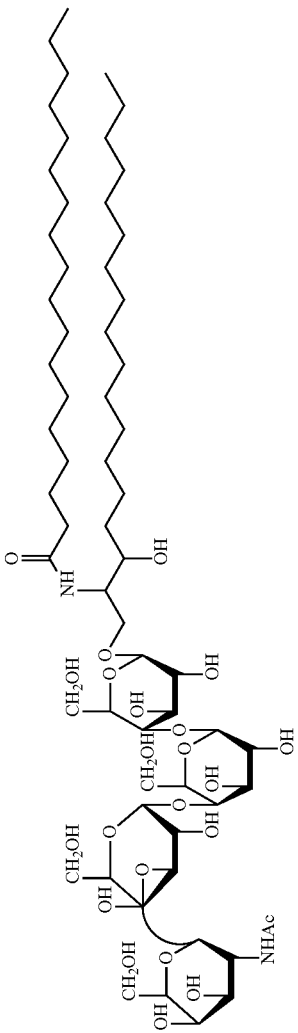

D

TABLE 2-continued

List of neutral glycosphingolipids in mammals (Source: Glycoscience III: Chemistry and Chemical Biology) Reiner, B.; Tatsuta, K; Thiem, J. (Ed.), Springer Verlag, 2001, ISBN 3-540-67765-8).

| Structure | Trivial name | Symbol[1] | Abbreviation |
|---|---|---|---|
| 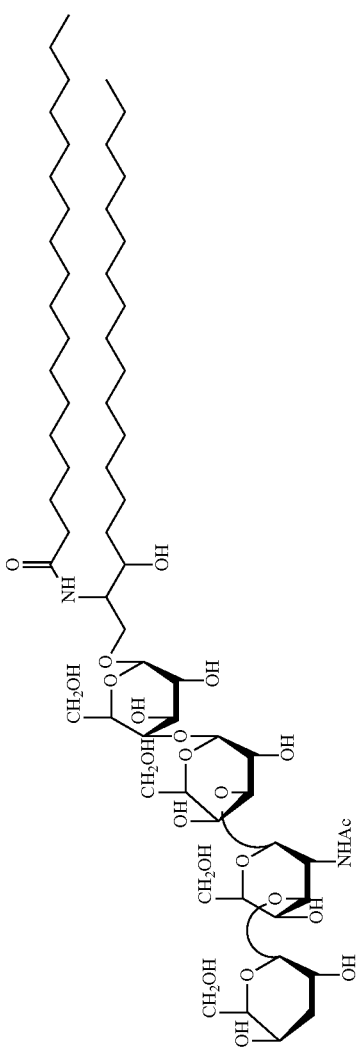 | | | |
| Plants 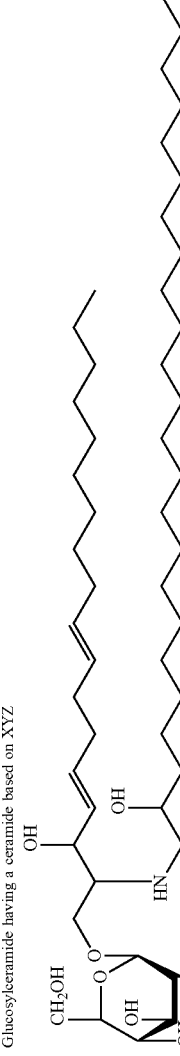 (6) RCO = acyl; R' = H (6') RCO = acyl; R' = Glcpβ (6'') RCO = acyl; R' = Manpβ (6''') RCO = acyl; R' = Manpβ1,4Manpβ | Glucosylceramide having a ceramide based on XYZ | | |
| 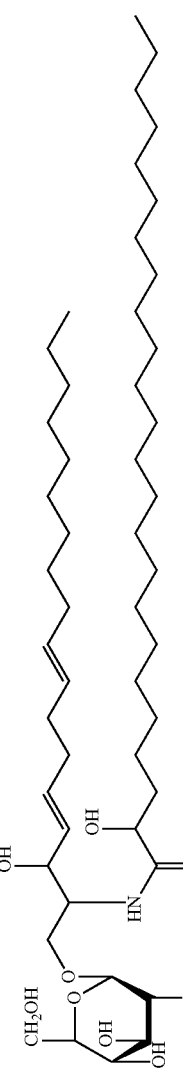 | Glucocerebroside having ceramide based on 4,8-sphingadienine and 2-hydroxy-tetracosanoic acid | | |

II) Mono-, oligo-, and polyglycosylphingoids

The glycosylsphingoides form a further group of the neutral glycosphingolipids, in which at least one saccharide residue is linked glycosidically to a sphingoid backbone, but this is not linked to a fatty acid at its amino group. They are also called deacetylated glycosylceramides. These include, for example, the O-sphingosyl galactosides (formerly referred to as psychosines) occurring in the brain of vertebrates.

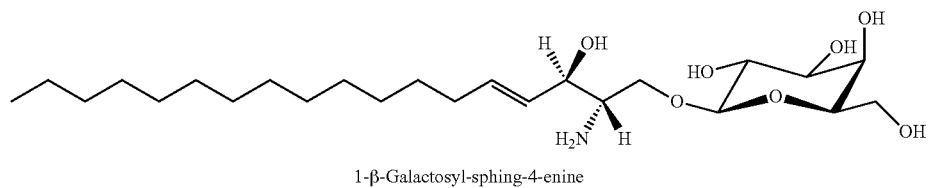

1-β-Galactosyl-sphing-4-enine

III) Acidic Glycosphingolipids: Glycosphingolipids having a sulfate residue, a phosphate residue, or a carboxyl residue as acidic group. The following subgroups belong to them:

IV) Sialoglycosphingolipids:

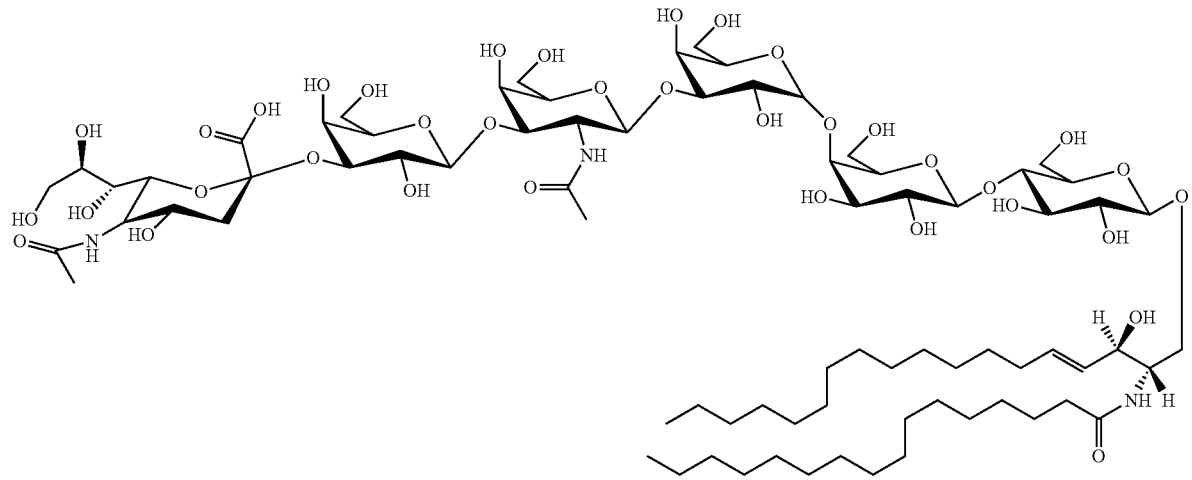

NeuAcα2-3Galβ1-3GalNAcβ1-3Galα1-4Galβ1-4Glcβ-Cer(d18:1/16:0)

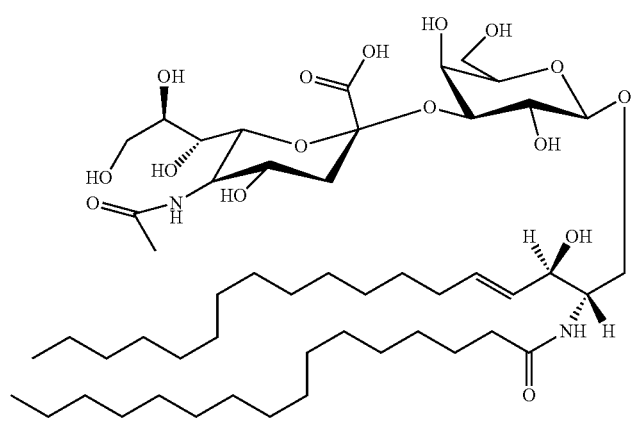

NeuAcα2-3Galβ-Cer(d18:1/16:0)

Glycuronoglycosphingolipids: Glycuronoglycosphingolipids are sphingolipids containing one or more uronic acid residues.

VI) Phosphoglycosphingolipids: Phosphoglycosphingolipids are sphingolipids containing one or more phosphomonoester or phosphodiester groups. As a rule, a ceramide is linked via its hydroxyl group at position 1 to an inositol phosphate. One therefore speaks in part of "inositol phosphorylceramides". In plants, the inositol phosphoceramide backbone may carry additional N-acetylglucosamine, glucosamine, fucose, glucuronic, arabinose, mannose, or galactose residues which may be attached to either the carbon atom in position 2 and position 6 of the inositol.

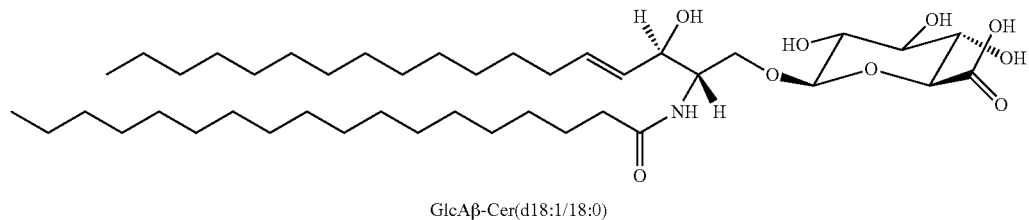

GlcAβ-Cer(d18:1/18:0)

V) Sulfoglycosphingolipids: sphingolipids containing one or more sulfate esters of saccharide residues. These are generally galactosylcerebroside, the galactose at position 3 being esterified with a sulfate group. Further saccharide residues, which are preferably glucose residues, may be linked to this sulfated galactose residue. A prominent representative is the 3-O-sulfogalactosylcerebroside occurring in the myelin sheath of mammalian neurons.

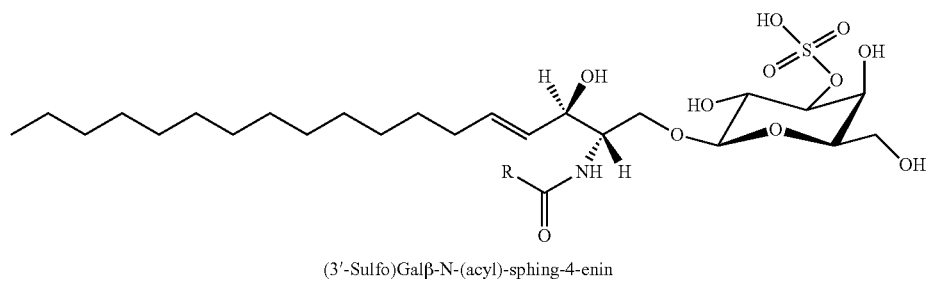

(3'-Sulfo)Galβ-N-(acyl)-sphing-4-enin

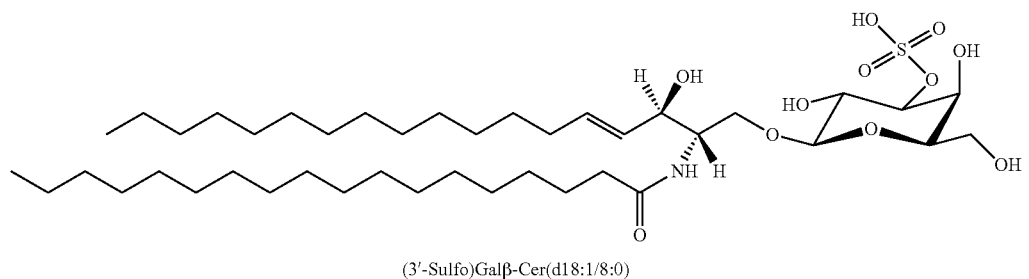

(3'-Sulfo)Galβ-Cer(d18:1/8:0)

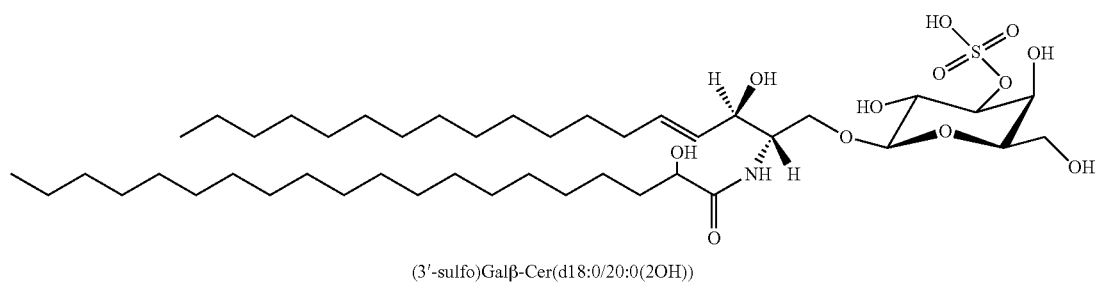

(3'-sulfo)Galβ-Cer(d18:0/20:0(2OH))

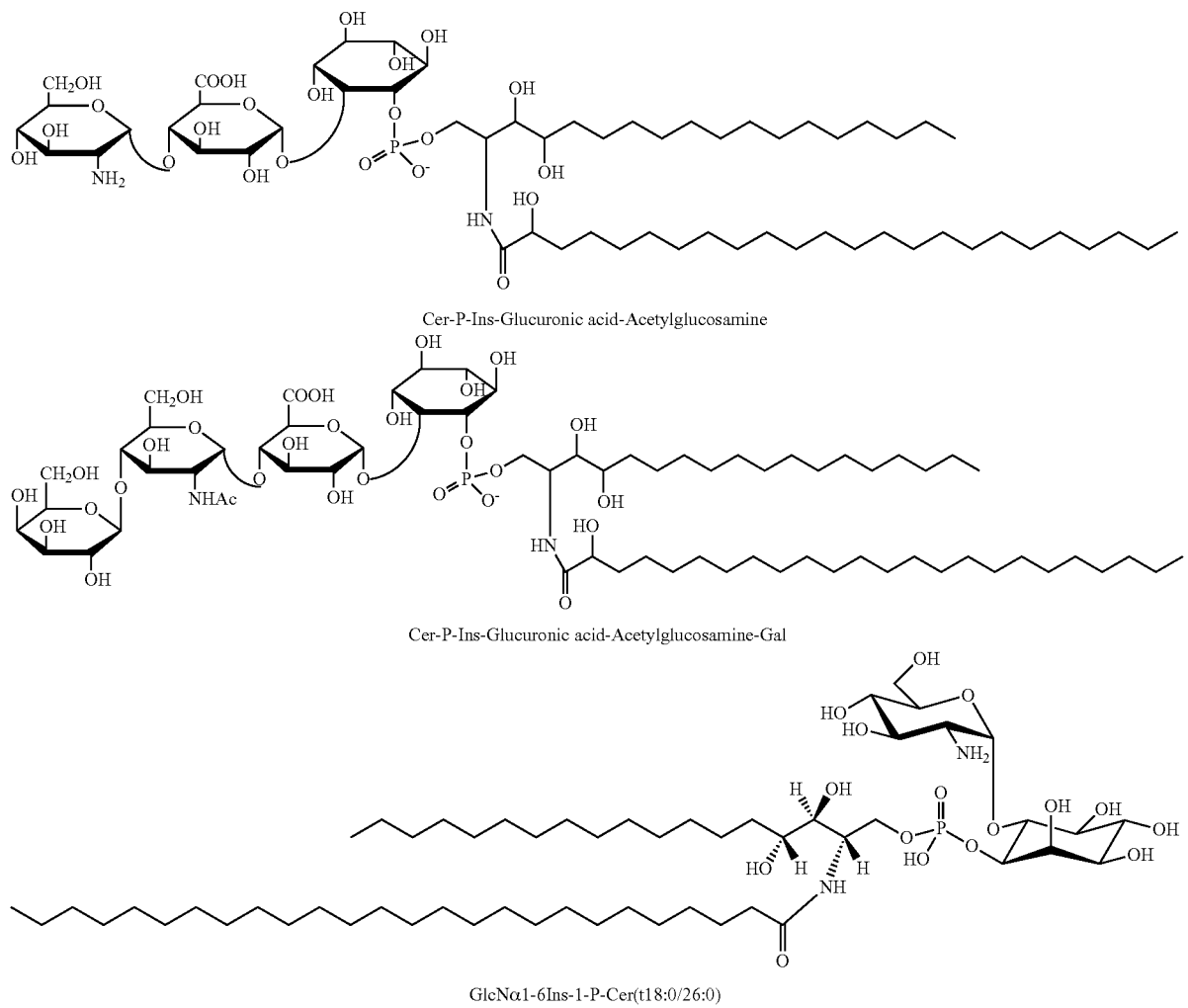

Cer-P-Ins-Glucuronic acid-Acetylglucosamine

Cer-P-Ins-Glucuronic acid-Acetylglucosamine-Gal

GlcNα1-6Ins-1-P-Cer(t18:0/26:0)

VII) Phosphonoglycosphingolipids are sphingolipids which predominantly occur in invertebrate and are characterized by at least one phosphonic ester bond.

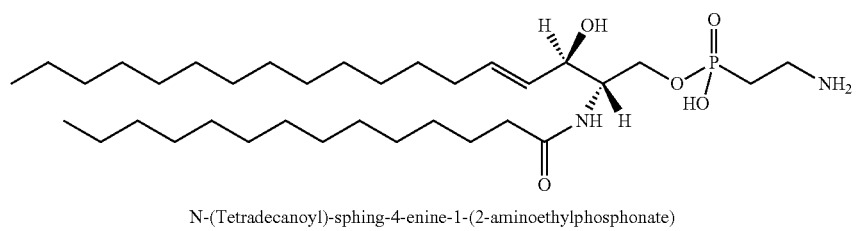 [SMILES: CCCCCCCCCCCCC/C=C/[C@@H](O)[C@H](COP(=O)(O)CCN)NC(=O)CCCCCCCCCCCCC]

N-(Tetradecanoyl)-sphing-4-enine-1-(2-aminoethylphosphonate)

Glycophosphatidylinositols: Glycophosphatidylinositols are glycolipids in which saccharides are linked glycosidically to the inositol group of phosphatidylinositols. They comprise both the corresponding lyso forms of the glycophosphatidylinositols as well as glycophosphatidylinositols with substituted glycerol or inositol residues, e.g., by O-acyl, O-alkyl or O-alk-1-en-1-yl substitutions.

Rhamnolipids:

Rhamnolipids consist of one or two rhamnose units which are attached to a hydroxyl group of a hydroxylated fatty acid, which in turn is esterified with another hydroxylated fatty acid, the fatty acids having a chain length of preferably 8 to 12 carbon atoms, but more preferably of 10 carbon atoms. Rhamnolipids are preferably formed by bacteria of the genus *Pseudomonas* which grow on a hydrocarbon source and have antifungal properties.

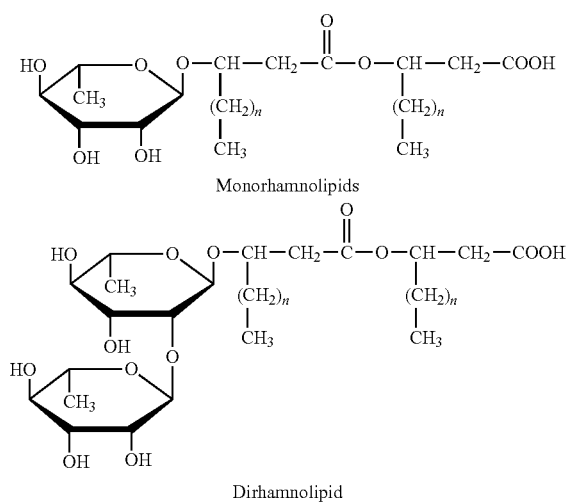

Monorhamnolipids

Dirhamnolipid

Sophorolipids: Sophorolipids consist of the disaccharide sophorose (also 2-O-glucopyranosyl-D-glucopyranose) linked to the hydroxy group of a hydroxylated fatty acid, the hydroxyl group being located either at the terminal carbon atom (position n) or at an immediately preceding position (position n−1). Sophorose can also be acetylated at one or both hydroxyl groups at position 6. A subgroup of the sophorolipids are the lactonic sophorolipids in which the carboxyl group of the hydroxylated fatty acid is esterified with the hydroxyl group at the 4'-position of the glucose subunit of the sophorose. Sophorolipids are preferably formed and excreted from yeasts of the genus *Candida*, particularly preferably *Candida bombicola* and *Candida apicola*.

Acidic sophorolipid

Lactonic sophorolipid

It should be noted at this point that some fatty acid glycosides could also be detected in plants in which a saccharide residue is linked to a hydroxylated fatty acid via a glycosidic bond between two hydroxyl groups. An example of this is, e.g. the tuberonic acid glycoside from the potato plant, in which the fatty acid tuberic acid (12-hydroxy-jasmonic acid) is glycosidically linked to the hydroxyl group at position 1 of glucose via the hydroxyl group at position 12.

In addition to the abovementioned fatty acid glycosides, in which a saccharide residue is bound to a fatty acid via a glycosidic bond between two hydroxy groups, there are also fatty acid glycosides which are formed by an ester linkage between a saccharide residue and a fatty acid. The following structural formula shows a fatty acid glycoside from cyanobacteria.

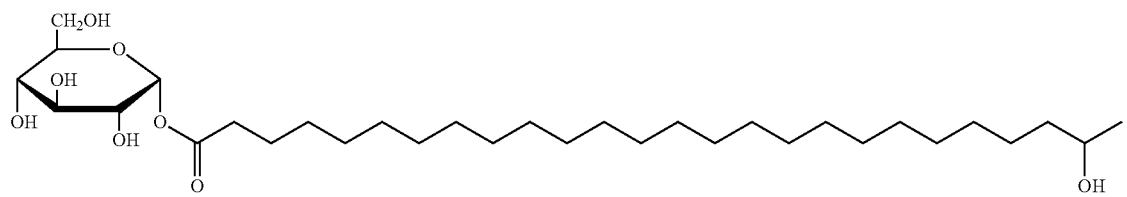

1-α-Glucosyl-25-hydroxy-hexacosanoic acid

For example, fatty acid glycosides in which a glucose residue or a sucrose residue is acylated to two to five hydroxyl groups, the chain length of the acyl groups being preferably 2 to 12 carbon atoms, are present in solanums. Examples include 2,3-diacylglucose, 1,2,3-triacylglucose, 2,3,4-triacylglucose, 2,3,4-triacylsucrose, 2,3,6-triacylsucrose, 2,3,1'-triacylsucrose, 1, 2,3,4-tetraacylglucose, 2,3,4, 6-tetraacylglucose, 2,3,4,6-tetraacylsucrose, 2,3,4,1'-tetraacylsucrose, 2,3,4,3'-tetraacylsucrose, 1,2,3,4,6-pentaacylglucose and 2,3,4,6,3'-pentaacylsucrose.

Trehalose Lipids:

Trehalose lipids consist of the disaccharide trehalose (1-α-glucopyranosyl-1-α-glucopyranoside or Glc (α1→1) Glc) which is linked to a fatty acid which is branched at least at position 2 and is hydroxylated at position 3. These fatty acids are preferably mycollic acids or their derivatives corynomolycolic acid or nocardomiccolic acid. If only the hydroxyl group at position 6 of one of the two glucose units of trehalose is esterified, it is referred to as monomycolates. However, if both glucose units of trehalose are esterified at their hydroxyl group in position 6, the term used is dimy colates. One of the best known representatives of trehalose lipids is the so-called cord factor (a trehalose 6-6'-dimycolate) from *Mycobacterium tuberculosis*, which appears to be important for the virulence and the drug resistance of the bacterium. In addition, polyacylated forms of trehalose lipids are known in which more than two fatty acid residues are linked to trehalose (e.g., triacyltrehaloses and pentaacyltrehaloses). The trehalose lipids are therefore complex glycolipids which can contain long and, in addition, also complex-branched fatty acid residues.

Trehalose lipids are preferred in bacteria of the genera *Mycobacterium*, *Rhodococcus*, and *Corynebacterium* as well as in fungi, algae, and also in insects.

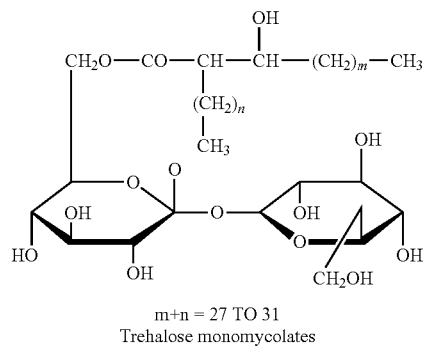

m+n = 27 TO 31
Trehalose monomycolates

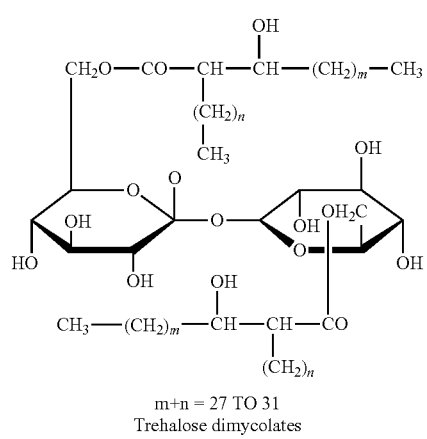

m+n = 27 TO 31
Trehalose dimycolates

Lipopolysaccharides:

The lipopolysaccharides are highly complex bacterial glycolipids consisting of lipid A and a polysaccharide complex attached thereto, which in turn can be subdivided into a core region and an associated O-specific polysaccharide. Lipid A is a fatty acid glycoside from a disaccharide of two N-acetylglucosamine phosphate units, this disaccharide having several fatty acid residues esterified. The most common fatty acids are caproic, lauric, myristic, palmitic, and stearic acids. Via the hydroxyl group in position 6 of the second N-acetylglucosamine phosphate, the lipid A is linked to the core region of the subsequent polysaccharide complex.

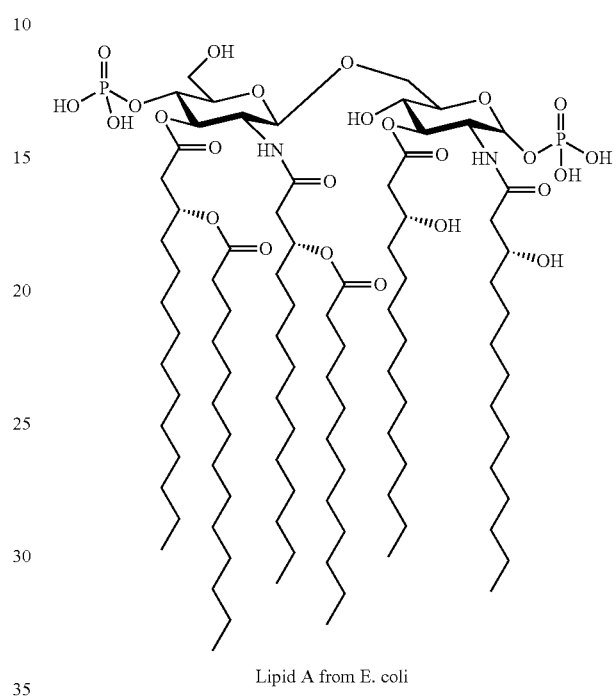

Lipid A from E. coli

Sterylglycosides:

The sterylglycosides are sterols which are linked via a hydroxy group to at least one saccharide residue. Sterylglycosides are found in plants, animals, fungi, and also in some bacteria. In animals, for example, there exists the cholesterol glucuronide, in which a cholesterol residue is linked to a glucuronic acid residue. In plants, the sterol residue is preferably campesterol, stigmasterol, sitosterol, brassicasterol, or dihydrositosterol, and the saccharide residue is preferably glucose, galactose, mannose, glucuronic acid, xylose, rhamnose, or arabinose. The saccharide residue in plant sterylglycosides is linked to the sterol via the hydroxy group at C3 of the A-ring of the sterol. Further saccharide residues can be linked to this first saccharide residue via a β-1,4-glycosidic bond or a β-1,6-glycosidic bond. There are the acylated sterylglycosides (ASGs) in which a saccharide residue at its hydroxyl group at position 6 is esterified with a fatty acid. In many plants, acylated sterylglycosides could be detected in virtually all plant components in up to 0.125% by weight. The proportion of nonacylated and acylated sterylglycosides in palm and soybean oil is particularly high. In the production of biodiesel, a high proportion of sterylglycosides is discussed in connection with poorer filterability.

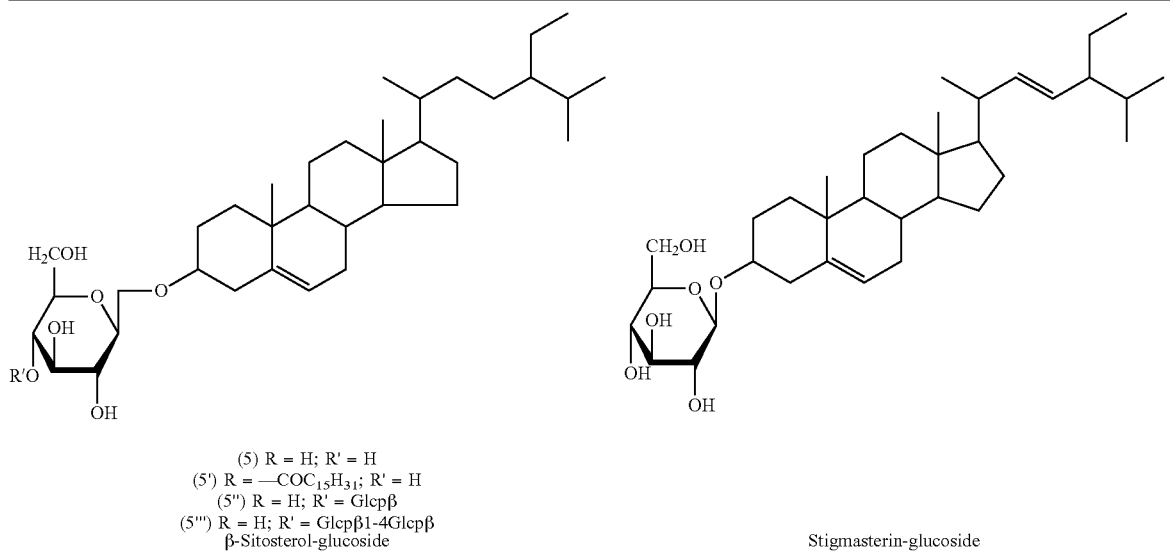

EXAMPLES

Methods

Figure 1:
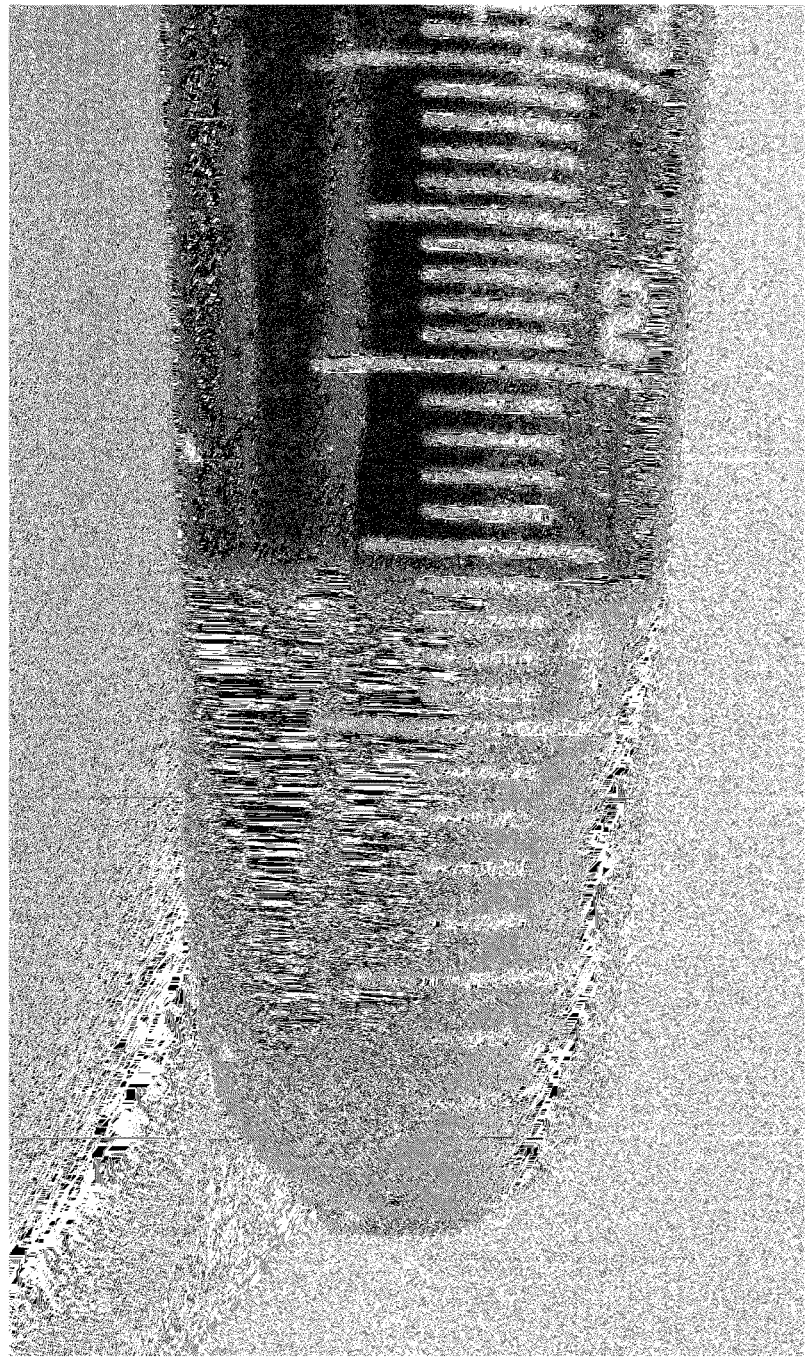
FIG. 1: shows a typical image of a glycoglycerolipid-poor lipid phase (top) separated from the aqueous phase (below) by centrifugation in step B1) in a sample vessel.
Figure 2:
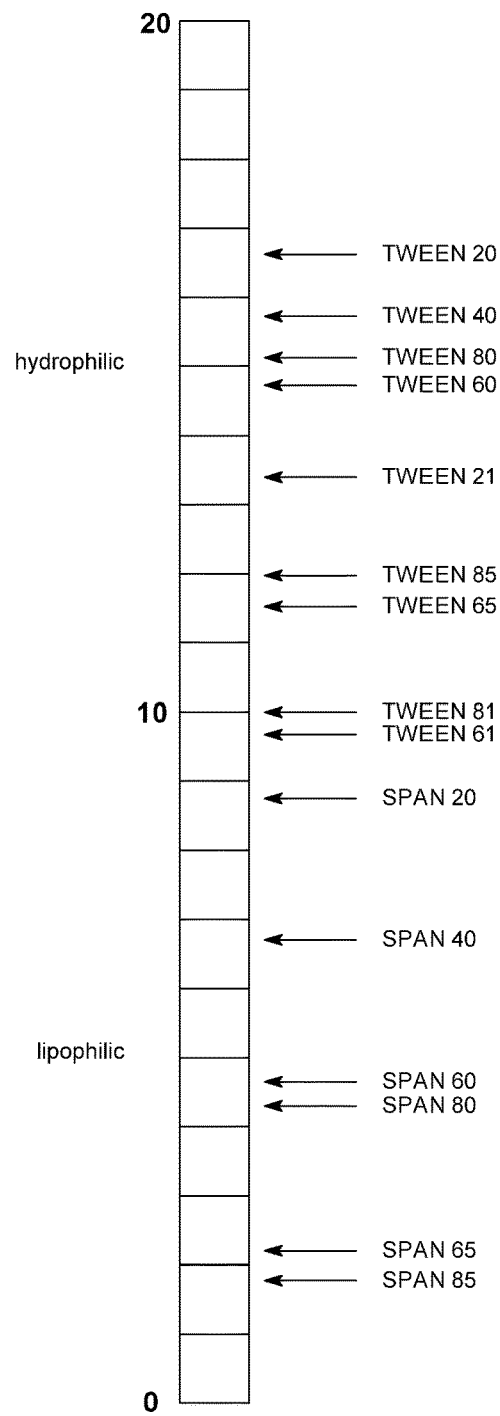
FIG. 2: shows the HLB lipophilicity scale wherein the lipophilicity of a substance increases in the range from 10 to 0 and hydrophilicity increases in the range from 10 to 20, and at a value of 10 the substances are equally lipophilic as hydrophilic; thus, they are equi-amphiphilic. For example, the value according to the HLB lipophilicity scale is given for various TWEEN and SPAN emulsifiers.

The efficiency of the inventive technique for separating a glycoglycerolipid-rich fraction from lipid phases can be examined by various methods from the prior art.

Viscometry

It has been shown that the separation of the glycolipid fraction significantly reduces the viscosity of the purified lipid phase. Therefore, a reduction in the viscosity of the purified lipid phase of at least 10%, more preferably at least 20%, and most preferably at least 30% as compared to the viscosity of the raw lipid phases considered to be a result according to the invention.

Alkaline Earth Metal and Metal Salt Binding Capacity

Alkaline earth metal ions and metal ions virtually do not distribute in an apolar lipid phase. However, sugar residues of glycoglycerolipids and glycosphingolipids are capable of fixating such ions via hydrogen bonds, which is why many lipid phases, such as vegetable oils, are contaminated with these ions. The binding capacity of a glycoglycerolipid-containing lipid phase for such ions can therefore be used to estimate the content of sugar compounds. The binding capacity for alkaline earth metal ions as well as metal ions is preferably reduced by 80%, more preferably by >90% and most preferably by >95% with the methods according to the invention.

The physico-chemical properties of the separated glycoglycerolipid-containing fraction can be investigated by established methods such as, HLB chromatography, tensiometry, and determination of the critical micellar concentration (CMC).

Qualitative detection of glycoglycerolipids and glycosphingolipids can be performed by methods such as atomic emission spectroscopy and thin-layer chromatography (TLC). By means of the latter, separation into different compound classes is possible with subsequent differentiation of the sugar residues present. A narrow and sharp delineation of the bands indicates a high uniformity of the compounds present therein, whereas a broadening and unspecific limitation of the bands indicates a heterogeneity of the compounds and, in particular, of the sugar residues, and thus this criterion is suitable for the detection of a hydrolysis.

ABBREVIATIONS

FFA: free fatty acids
ppm: parts per million
na: not applicable/not tested
nd: not investigated/determined
rpm: revolutions per minute

Example 1

Recovery of a Glycoglycerolipid Lipid Fraction after Degumming of a Press Oil

For testing whether after the degumming of a press oil or separation of fatty acids which still remain in the lipid phase by means of an aqueous solution containing guanidino compounds, a crude oil of a screw pressing of stored jatropha nuts obtained at a temperature of 60° C. with the following key values: total phosphorus content 248 ppm, FFA 1.8 wt %, calcium 70 ppm, is refined according to the following scheme:
- a) 3% addition of a 0.5-1.0 molar NaOH solution
- b) 3% addition of a 75 wt % phosphoric acid solution
- a1) refined oil after step a) 0.3% addition of a 0.6 molar arginine solution
- b1) refined oil after step b) 0.3% addition of a 0.6 molar arginine solution The refined oils obtained after the above-described steps were then further treated with the following steps:
- c) 5% addition of a 10% sodium metasilicate solution
- d) 4% addition of a 15% potassium carbonate solution For each experiment, 200 ml was used for each refining step. The aqueous solutions were admixed by homogenization with an Ultrathurrax at 24,000 rpm for 3 minutes that was carried out by cycling movement of the container at room temperature. The resulting emulsions were centrifuged in a beaker centrifuge at 3,800 rpm for 5 minutes. Then upper phases were separated by decanting or withdrawing the phase.

In the oil phases, contents of phosphorus, free fatty acids, and calcium were determined, and the quantity of dry mass of compounds that were contained in the aqueous phases was determined after steps C) and C). For the latter, the water was removed by vacuum drying. Furthermore, the water-binding capacity of the previously treated oils A1) and A1) and of the glycoglycerolipid-poor lipid phases obtained after performing steps: A1)+C); A1)+D); B1)+C); B1)+D), according to the invention, were investigated by admixture of deionized water (1 ml to 50 ml) with an Ultrathurrax (20,000 rpm for 2 minutes) to the obtained oil phases and then the mixture was separated with a centrifuge at 4,000 rpm. The water content of the oils was determined by the Karl Fischer method. The dried organic materials from the separated water phases were dissolved in chloroform, followed by centrifugation at 5,000 rpm for 5 minutes. Then, the solvent phase was withdrawn and the organic matter was dried by means of a vacuum evaporator. Each of 20 mg of the obtained dry matter was dissolved in 1 L of deionized water. Samples therefrom were used for determination of the surface tension by means of a tensiometer (K 100, Krüss, Germany).

Results:

The degumming procedures resulted in a substantial removal of hydratable phospholipids, free fatty acids, and a marked reduction of alkaline earth metal ions. Significant amounts of lipophilic organic compounds were separated into the aqueous medium by treatment with solutions of the salt compounds according to the invention which were admixed with an intensive mixing procedure; those compounds could then be removed. The amounts of the obtained dry substance were considerably greater than the calculated sum of the residual amounts of phospholipids, fatty acids, and alkaline earth metals which had also been separated. From the resulting dry mass, glycerolipids can be converted into an organic solvent and recovered therefrom. The obtained glycoglycerolipids exhibited extremely good surfactant properties in water.

Example 2

The oily fraction after sedimentation of the press liquid of the Accocromia palm fruit with the key values: phosphorus content 128 ppm, FFA 2.6 wt %, calcium 48.8 mg/kg were examined with regard to separable glycoglycerolipid lipid fractions.

For this purpose, 200 ml of the lipoid phase were pretreated by the following methods:
- a) addition of 5% of a low-ion water stirring with a propeller stirrer at 2,500 rpm while heating at 50° C. for 90 minutes.
- b) addition of 3% of a citric acid solution which is homogenized by means of an Ultrathurrax for 5 minutes at 24,000 rpm while heating the emulsion to about 50° C.

The lipid phases that have been refined with the above-described steps which were obtained after centrifugation were further treated by each of the following steps:
- c) addition of 8% of a 15 wt % copper acetate solution,
- d) addition of 4% of a 20 wt % sodium hydrogen carbonate solution.

The aqueous phases of c) and d) are homogenized with the lipoid phases by means of an Ultrathurrax for 5 minutes at 24,000 rpm while heating the emulsions to about 50° C. The resulting emulsions were centrifuged in a beaker centrifuge at 4,000 rpm for 5 minutes. Subsequently phase separation was carried out by decanting or withdrawing the lipoid phases.

The treated lipoid phases of refining steps c) and d) were reprocessed by the identical cleaning step as previously carried out and designated as c1) and d1). Thereafter the obtained lipoid phase c1) was treated according to process d) and the obtained lipoid phase d1) was treated according to process c).

The content of phosphorus, free fatty acids, and calcium was determined in the lipoid phases, and for the aqueous phases of refining steps c) and d) the amount of the organic mass after drying were determined; further for the latter samples the HLB value was determined. Determination of the HLB value was carried out with an Asahipak GF-310 HQ multiple solvent GPC column. Here, ionic and nonionic surfactants can be differentiated and classified according to their HLB value.

Thin layer chromatography was performed with silica gel G plates. Separation was carried out using a mixture of chloroform/acetone/water (30/60/2). These were developed using a naphthylenediamine reagent, whereby sugar residues of the glycerolipids can be color-coded.

Results:

The lipid phase of palm kernel peel material has a high content of nontriglyceride contaminants which consist largely of glycerol glycerides and sterols and contain only a small proportion of phospholipids. These accompanying substances cause turbidity and high viscosity of the oily phase. The residual values for phosphorus, free fatty acids, and alkaline earth metal ions were already significantly reduced by aqueous or acid degumming, but the lipoid phases remained highly viscous. An intensive mixing process of the aqueous solutions containing compounds according to the invention with the lipoid phase resulted in considerable formation of emulsions which further increased viscosity. However, further homogenization using a rotor-stator mixer enabled liquification of those emulsions which could be separated by centrifugation into a slightly turbid lipoid phase and a whitish semisolid mass. The amount of organic matter removed from the lipoid phase as achieved in the first separation step was largely independent of the previously performed degumming process and the salt dissolved in the aqueous phases according to the invention. It was found that even with a second separation, relevant amounts of oil contaminants could be separated. Then, in a further refining step using an intensive mixing process with the aqueous solutions of the salts according to the invention, virtually no additional accompanying substances could be separated. The total amounts of solids separated were far above the calculated sum of phospholipids, fatty acids, and metal ions separated. By thin layer chromatography, on the one hand, co-separation of relevant quantities of triacylglycerols could be excluded; on the other hand, digalactosyl- and monogalactosyldiglycerides as well as sterylglycosides could be detected. In the surfactant analysis, the presence of ionic surfactants in discrete amounts with an HLB value of 13 as well as a clear detection of nonionic surfactants with an average HLB value of 8 and 9 were found for the separated phase of c) and d).

Example 3

Linseed press cake was placed in an aqueous solution with addition of 5% isopropanol and was homogenized with an immersion blender. The slurry was then stirred at 50° C. for 30 minutes. This was followed by the addition of a 3-fold amount of petroleum ether. After further homogenization, a centrifugal phase separation was carried out. The separated organic phase (OP1) was reduced to half its initial volume by means of a vacuum evaporator. This was followed by the addition of 5 vol % of a methanol/water mixture (95/5) to OP1, mixing of the solution, and subsequent centrifugal phase separation. The lightly turbid alcohol-water phase was pipetted off. The remaining organic phase (OP2) is fractionated and the following volume fractions and concentrations of the substances according to the invention are provided to the resulting fractions:
A) potassium carbonate, B) sodium dihydrogen carbonate, C) mixture of sodium and potassium metasilicate, D) calcium acetate, E) aluminum acetate tartrate, F) sodium borate with concentrations of 3%, 10%, and 15% and a volumetric addition of 2%, 4%, and 8%, respectively.

To 100 ml each of the organic phases (OP2), the solutions according to the invention were added and homogenized with an Ultrathurrax at 24,000 rpm for 30 seconds. After 3 minutes standing time, phase separation was performed at 4,000 rpm over a period of 10 minutes. The supernatant (organic phase, OP3) was then separated. Each of the corresponding aqueous phases (WP3) was intensively mixed with 50 ml of n-heptane, followed by phase separation as described above. The resulting aqueous phase (WP4) was dried with a vacuum evaporator and the dry matter was weighed. Analyses of the content of phosphorus (atomic absorption analysis) and nitrogen (Kjeldahl's method) of the dry mass were carried out for the investigations with a volume addition of 10% from all investigated substances. Thin layer chromatography according to Example 2 was prepared using the dry substance from each batch.
Results:

The mixing of the organic phases (OP2) with the aqueous salt solutions A)-F) according to the invention resulted in considerable emulsion formation. Phase separation could be carried out by centrifugation obtaining a creamy colored semisolid (at 2 vol %) to a viscous (at 15 vol %) aqueous phases (WP3) and a slightly to moderately turbid organic phase (OP3). After extraction of di- and triacylglycerides by means of an n-heptane extraction, WP3 was dried by vacuum drying, resulting in a brownish sticky, highly viscous residue. Only of small amounts of nitrogen-containing compounds (e.g. sphingolipids or proteins) or phosphate-containing compounds (e.g. phospholipids) were in there. In thin layer chromatography, bands corresponding to digalactosyl- and monogalactosyldiglycerides and sterylglycosides were present in all samples. It thus has been shown that a selective separation of glycoglycerolipids and glycosphingolipids from a lipoid phase of a phytoextraction is possible with the method according to the invention.

Example 4

Rice bran from a standard process of rice processing with an oil content of 18% and a water content of 35% was stored at −8° C. after obtaining until lipid extraction. This starting material was mixed with 10% water and stirred at 30° C. for 2 hours. The mixture was extracted twice with n-hexane at 50° C. The aqueous phase (WP1) was concentrated to a highly viscous residue by means of a vacuum evaporator. Each of 100 g of the highly viscous mass was mixed with 300 ml of a mixture of chloroform and acetone (80:20), and the organic phase (OP2) was separated by means of centrifugal phase separation. Samples of 150 ml of OP2 were each mixed with either 20 ml aqueous solutions of a) sodium carbonate, b) sodium orthosilicate, c) copper acetate (Cu(OAc)$_2$), d) potassium tartrate or e) potassium borate, each at concentrations of 15%, and homogenized with an Ultrathurrax at 20,000 rpm for 20 s. After a standing period of 60 seconds, phase separation was carried out by a centrifuge at 5,000 rpm for 10 minutes. The respective organic phases (OP3) were separated and the respective aqueous phases (WP3), which had a highly viscous to semisolid consistency, were homogenized. From the homogenized aqueous phases (WP3), a 1 ml sample was separated, the remainder was dried by means of a vacuum evaporator and the quantity of substance which subsequently remained was weighed. The separated sample was hydrolyzed with sodium methoxide dissolved in methanol and then fractionated by means of silica gel chromatography. The fraction of glycosylceramides was dissolved in pyridine and MTPA-Cl (α-methoxy-α-trifluoromethylphenylacetic acid chloride) was added at 0° C. The solution was stirred and concentrated over 24 hours at room temperature. After further purification by means of silica gel column chromatography with hexane/ethyl acetate (1:1) as eluent, a white solid was obtained after evaporation of the eluent. Using ESI-TOF-MS (electrospray time-of-flight mass spectrometry), sugar esters (m/z 1195.52 [M+H]+) were detected. The organic phases (OP3) were completely evaporated and the resulting solids were hydrolyzed and processed by the same method as described above.
Results:

Aqueous extraction of OP2, organic matter with quantities of a) 8.4 g, b) 11.7 g, c) 10.2 g, d) 9.9 g, and e) 10.1 g could be separated. In the separated organic matter which has been obtained from WP3 sugar compounds could be detected after hydrolysis, so that the presence of various sugar-containing lipid compounds (glycoglycerolipids, glycosphingolipids) can be assumed. In the organic phases (OP3), practically no sugar compounds could be detected after the hydrolysis, so that separation of sugar-containing compounds by means of the aqueous extraction process according to the invention is largely complete.

Example 5

Examination on the extraction and recovery of glycoglycerolipids and glycosphingolipids from lipoid plant extracts and for their use as a baking aid.

Cold pressed fruit pulp from kernels of the Acrocomia palm with an oil content of approx. 70% was diluted 1:1 with a mixture of acetone, dichloromethane, and hexane (ratio 1:1:5) and mixed well mechanically. Thereafter, two extraction steps were carried out with an aqueous 0.4 molar arginine solution at a volume addition of 4% in each. Phase separation was achieved by centrifugation. The lipoid phase was first mixed twice with a 10% sodium carbonate solution with a volume addition of 4% and the mixture was stirred; while the first mixing procedure was performed with an stirrer at 500 rpm and 15 minutes, the mixing procedure in the second extraction was carried out with an Ultrathurrax at 18,000 rpm for 5 minutes using an aqueous solution with identical volume and concentration. Phase separation was carried out by centrifugation at 5,000 rpm over 15 minutes. Each of the aqueous phases of the two subsequent separations consisted of a white viscous emulsion. The emulsions were combined and then freeze-dried. Subsequently, the lyophilized mass was dissolved in a mixture of chloroform and methanol (5:1), and forwarded to preparative column chromatography (silica gel matrix 60). Elution was performed with acetone/chloroform (5:1). The eluate was dried by means of a vacuum evaporator. A dry mass of 56 g was obtained; the initial quantity was 800 g.

With the fraction thus obtained, containing glycoglycerolipids and glycosphingolipids, small-sized baking experiments were carried out according to a standard procedure: dough was prepared using 10 g flour, 7% fresh yeast, 2% of NaCl, 1% sucrose, 0.002% ascorbic acid, and water in which 30 mg of the mass containing glycoglycerolipids and glycosphingolipids had been dissolved by mixing (1200 rpm at 20° C. for 1 minute). The prepared samples were allowed to rise at 30° C. for 40 minutes, and were then baked at 185° C. for 10 minutes. Then the volume of the baked material was determined. For comparison, baking tests were carried out under identical conditions without addition of the mass containing glycoglycerolipids and glycosphingolipids and with addition of 0.3% of a pure lecithin powder (Jean-Puetz, Germany), which had been dissolved in water.
Results:

The liquid obtained by pressing the palm kernel fruit from palm trees of the genus Acrocomia is a lipoid phase in which a high proportion of glycoglycerolipids and glycosphingolipids, waxes, free fatty acids and fibers are present. Mixing with water results in formation of stable emulsions which cannot be broken by physical measures. It has been found that the separation of the free fatty acids is possible by means of an aqueous arginine solution while simultaneous dissolving of other lipoid substances in organic solvents and that subsequently a fraction containing glycoglycerolipids and glycosphingolipids can be separated off by aqueous extraction according to the invention. During the first addition of the solution with an intensive mixer, strong emulsion formation resulted; here subsequently performed phase separation had a poor result. When the aqueous solution was initially admixed by stirring with a propeller mixer, whereby input of air was avoided, there was also a marked formation of aggregates; however, phase separation was possible. After the first depletion of the lipoid phase, repeated admixture of the salt solution by means of an intensive mixer resulted in formation of an emulsion also, separation by means of centrifugal phase separation into a clear oil phase and a water phase containing solids was possible. The obtained aqueous fractions were combined, from this fraction a mixture of glycoglycerolipids and glycosphingolipids was obtained after preparative purification that was readily dissolvable in water. In the baking tests, a significant increase in the volume of the baking product was observed compared to baking results without addition of the mass containing glycoglycerolipids and glycosphingolipids (+300%) and compared to the result with lecithin added (+120%).

Example 6

Investigations of the effect of process parameters on the extraction efficiency and hydrolysis stability of fractions containing glycoglycerolipids and glycosphingolipids Camelina oil, obtained by means of a screw press at 50° C., was intensively stirred with 3% deionized water for 1 hour at 45° C. Subsequently, the water phase was separated by means of a separator. To each 200 ml of the water-degummed oil (oil1), 4 vol % of an aqueous solution of potassium hydrogen carbonate, anhydrous sodium metasilicate, and calcium acetate (in each case 15 wt %) was added and homogenized with an Ultrathurrax for 5 minutes at 25,000 rpm. Immediately thereafter, centrifugation was performed at 5,000 rpm for 10 minutes, separating the oil phase (oil2) and the aqueous phase (WP1), from which oil-associated residues were removed by layering hexane and subsequent centrifugation, and then removing the organic phase. The thus obtained aqueous phase (WP2) had a highly viscous consistency. The WP2 was shaken and divided in 2 equal volume fractions; one of which was subjected to vacuum drying, then the dry weight was determined. Thin layer chromatographic studies were carried out from a sample of the degummed oil (oil1) and of the oil phase (oil2) obtained after the aqueous extraction. The degummed oil (oil1) showed distinct and sharply defined bands corresponding to monogalactosyldigigcerides, digalactosyldiglycerides, and glycosphingolipids. There were virtually no bands visible in the TLC of the oil phases (oil 2), which were treated with the above-mentioned aqueous solutions. The second volume fraction of WP 2 was intensively shaken immediately after preparation with a solvent mixture (chloroform/methanol/acetic acid, 90/8/2) and the organic phases (OP 1) were removed. The solvents of the obtained organic phases were removed by vacuum drying and the dry substance, which remained from the organic phase (OP1), was dissolved in the solvent mixture to subsequently perform thin layer chromatography. The chromatographic analyses were carried out in order to detect bands for glycoglycerolipids and glycosphingolipids and in respect of the width of the respective bands. Then aliquots of 100 ml each of oil phase 2 (oil 2) were homogenized with each of the previously used salt solutions by means of an Ultrathurrax for 5 minutes. Subsequently, phase separation was performed and the quantity of dry matter of organic compounds in the water phases was determined as described above.

Various test modifications using 100 ml aliquots of the oil were performed using aqueous solutions of the above-mentioned salts according to the invention. Variations of the process temperatures (35, 55, and 75° C.) and the intensity of the mixing procedure after addition of the aqueous solutions with the above-mentioned salts according to the invention were performed. Furthermore, mixing devices differing in the achievable mixing intensities thereof were used: A) Ultrathurrax 25,000 rpm, B) Propeller mixer 2500 rpm, C) Ultrasonic. The mixing procedures were carried out for 5 minutes under continuous temperature control.

In other investigations the mixing process was performed with mixer B) and C) for a duration of 10 and 20 minutes.
Results:

The intensive introduction of the aqueous solution with the substances according to the invention which was established in preliminary studies was applied in corresponding reference investigations, and it could be shown that an almost complete separation of glycoglycerolipids and glycosphingolipids was enabled. Moreover, thin layer chromatography results of the fractions obtained from the aqueous phases (WP2) resulted in identification of bands that correspond to glycoglycerolipids and glycosphingolipids, and which exhibited sharp boundaries, i.e., no relevant hydrolysis had taken place.

The amounts of the separated dry matter obtained after a mixing procedure with a propeller mixer were markedly lower than those obtained by an intensive mixing procedure. In the same way, the amount of glycoglycerolipids and glycosphingolipids found in the oil treated in this way was also clearly discernible. By a renewed treatment by admixture of the respective salt solutions by means of an intensive mixer, further organic material was extracted; the quantities of the dry matter of both extractions were comparable to that obtained from an extraction by using an intensive mixer only.

Chromatographic bands corresponding to glycoglycerolipids and glycosphingolipids were present in all samples of the dry masses obtained by the extractions with the above-mentioned salt solutions. There was no broadening of the boundaries of the chromatographic bands for the investigations that were performed with durations <5 minutes, indicating the absence of hydrolysis products. A longer duration of the mixing process with the propeller mixer increased the amounts of extractable organic matter to an amount comparable with that obtained by an intensive mixing process. While at a mixing temperature of 35° C., only a treatment time of more than 10 minutes caused slight signs of a hydrolysis of the glycoglycerolipids and glycosphingolipids, hydrolysis-induced widening of the bands of the glycoglycerolipids and glycosphingolipids could be seen already after 5 minutes at higher treatment temperatures which increased significantly when mixing was performed longer at these temperatures.

Example 7

Grape press residues were microbially decomposed in a fermentation tank under continuous percolation conditions and addition of carboxylic acids. After 7 days, a sample of 1 liter was taken and intensively mixed with 1 liter of biodiesel (C8 to C18-methyl ester). The mixture was centrifuged and the heavily turbid organic phase (OP1) was removed. Then 100 ml of the organic phase (ON) was mixed with 5 ml of magnesium hydrogen carbonate or potassium acetate (10% strength aqueous solution) at 30° C. using a propeller mixer at 1,000 rpm for 7 minutes. This was followed by centrifugation at 4,000 rpm for 10 minutes. The resulting organic phase (OP2) was only slightly turbid; the aqueous phase (WP2) consists of a cream-colored semisolid mass. After carefully decanting the organic phase (OP2), the aqueous phase (WP2) was added to 100 ml of chloroform and mixed (OP3). Then 2 ml of 0.1 molar HCl (in deionized water) were added to WP2 and intensely mixed. The resulting mixture was centrifuged and the aqueous phase (WP3) pipetted off. Thereafter, 2 ml of a methanol-water mixture (80:20) were admixed and mixture was then centrifuged. After pipetting off the slightly turbid methanol phase, the solvent of the organic phase (OP4) was removed by means of a vacuum evaporator and the dry substance was weighed. A 5 µg sample thereof was separated and dissolved with a mixture of chloroform and methanol (90:10) and subsequently applied to a thin layer chromatography plate (Macherey-Nagel, Germany); for the development a mixture of chloroform:methanol:water (70:28:2) was used as eluent.

Development and dyeing of the plates was performed with anisaldehyde reagent (Sigma, Germany) at 200° C. For reference, concentrates from vegetable mono- and diglycoglycerolipids were applied separately. The cleaved sugar-containing compounds can be classified based on the color reaction: glycoglycerolipids—green/blue-green, glycosphingolipids—blue, glycerophospholipids—gray or violet, hydrolyzed glycoglycerophospholipids—intensely red or violet.

Results:

From a lipid substance mixture which was converted into an organic phase, relevant amounts of the glycoglycerolipids and glycosphingolipids dissolved therein were separated into an aqueous phase (with magnesium carbonate 8 g and with potassium acetate 7 g) by means of the aqueous extraction process according to the invention. By means of thin layer chromatography, the presence of ceramides, sphingolipids, and glycosphingolipids as well as glycoglycerolipids could be identified, whereby monoglycosyl-glycero- and diglycosylglycerolipids could be detected for the latter. Only bands suggesting glycophospholipids were shown.

The CMC (critical micelle formation concentration) was 55 mg/l for both extracts. The determined surface tension was 28.1 mN/m.

Example 8: Single Steps

For the steps described in the following, 200 kg of lipoid phase (cold-pressed camelina oil) were used.

Example 8A: Step A2') Treatment with Citric Acid Solution

The lipoid phase in the feed tank is heated to 60° C. and then 0.1 wt % of citric acid (33 wt %, at room temperature) is added and the mixture is intensively stirred for 30 seconds and then stirred for 10 minutes at about 100 to 150 rpm. Then, 0.3 wt % of water is added.

The mixture of lipoid phase and dilute citric acid is then pumped into the separator and the aqueous phase is separated from the oily phase at a capacity of 200 l/h. For further processing, the oily phase is transferred to a further receiving tank (receiving tank 2).

Example 8B: Step A2) Treatment with Water

The lipoid phase in the feed tank is heated to 65° C. and then 3 wt % of water (at room temperature) is added and stirred intensively for 30 seconds and then stirred for 10 minutes at about 100 to 150 rpm.

The mixture of lipophilic phase and water is then pumped into the separation separator and the aqueous phase is separated from the oily phase at a capacity of 200 l/h. For further processing, the oily phase is transferred to a further master tank (master tank 2).

Example 8C: Step B1) Treatment with Sodium Bicarbonate/Sodium Acetate Solution

The lipoid phase is brought to a process temperature of 45° C. to 50° C. and a sufficient volume of 8% sodium hydrogen carbonate solution/sodium acetate solution is added. Subsequently, a fraction (A)) is intensively stirred for 30 seconds by means of a Ystral mixer and then stirred normally for 10 minutes. A second fraction is homogenized with the intensive mixer (B)) according to the invention for 2 minutes.

The mixture of A) is then pumped into a standard separation separator and the aqueous phase is separated from the oily phase at a capacity of 200 l/h. The oily phase is transferred to a master tank for further processing.

Figure 3:
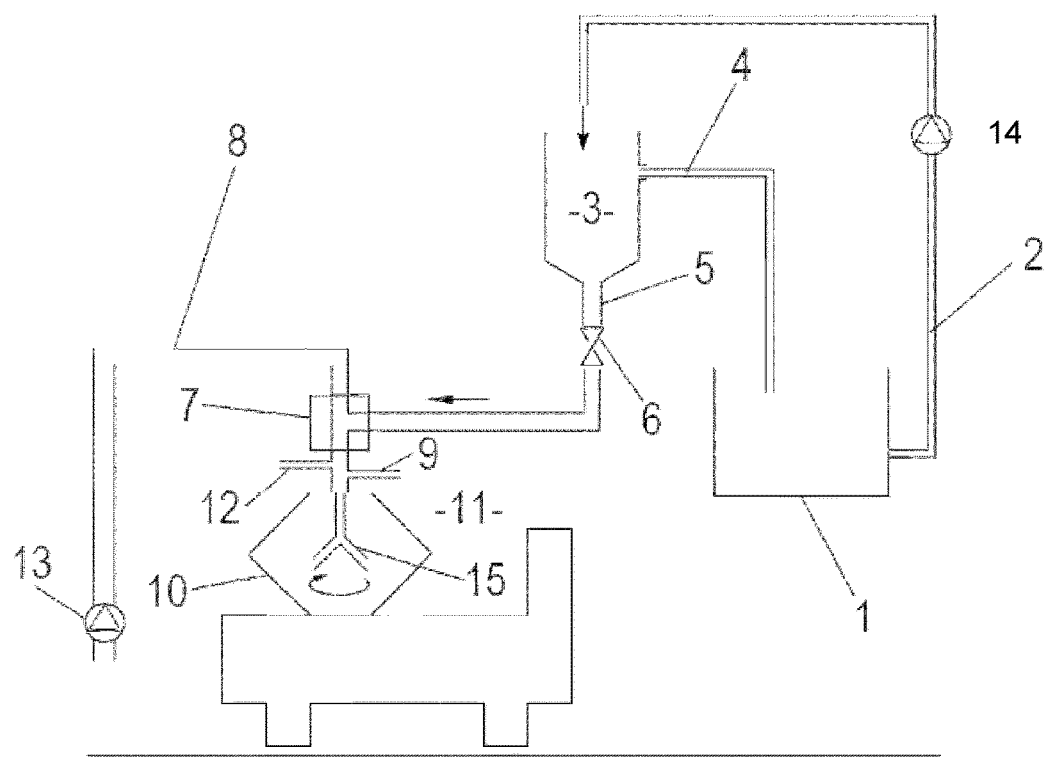
FIG. 3: shows a device according to the invention for carrying out the methods described herein. 1 is a receiving vessel for receiving the aqueous phase containing the mentioned salts, 2 stands for a line (pipe), 3 is a container, 4 is an overflow return, 5 is a discharge line, 6 is a valve, 7 is a mixer, 8 is a feed line, 9 discharge line, 10 a centrifuge, 11 and 12 are two outlets from the centrifuge, 13 a pump, 14 a further pump, and 15 a distributor.

The mixture of B) is then pumped into the separation separator according to FIG. 3 and thus the aqueous phase is separated from the oily phase at a capacity of 200 l/h. The oily phase is transferred to the master tank (master tank 1) for further processing.

Example 8D: Step E1) Treatment with Arginine Solution

The lipoid phase is brought to a process temperature of 40° C. to 45° C., and a volume of 0.6 M arginine solution is added, in such a way that 1.5 moles of arginine per mole of free fatty acids are present. The mixture is then carefully stirred for 10 minutes.

The mixture is then pumped into the separation separator and the aqueous phase is separated from the oily phase at a capacity of 200 l/h. The oily phase is collected.

Results:

The oily phases had a significant turbidity after the steps A2 and a slight turbidity after A2') and had a concentrations of: FFA 0.31%, iron 0.23 ppm, phosphorus 34 ppm and a content of $H_2O$ of 0.55% after A2), and of: FFA 0.42%, iron 0.15 ppm, phosphorus 19.6 ppm, and a content of $H_2O$ of 0.30% after A2').

The intensive mixing with a standard mixer in the course of process step B1) resulted in a significant emulsion formation, which was associated with an increase in viscosity. An introduction into a standard separating separator could only be made possible by increasing the temperature in the receiving container to 60° C. The aqueous phase obtained with the standard separating separator has a slightly yellowish color and had a cream-like consistency. The dry matter obtained from the aqueous phases of the separation according to process step A2) amounted to 2.3 kg and of the separation according to process step A2') 2.1 kg. It was found that about 20% of the anhydrous residue corresponded to triacylglycerides. The oily phases were markedly turbid.

Under the application of the intensive mixer according to the invention, as shown in FIG. 3, in process step B1) there was virtually no formation of emulsion of the lipoid phase. The introduction of such a air-introduction-free mixed lipoid phase in the separator was possible at low temperature conditions without any problems. The aqueous phase obtained by means of the separator had a whitish color and a milky texture. The determination of the dry matter resulted in values of 2.1 kg for the separation according to process step A2) and 2.0 kg for the separation according to process step A2'). The oily phases were considerably turbid.

The following values are determined in the chemical analysis:

B1) with standard mixer/separator: FFA 0.21%, $H_2O$ content 0.65%, iron 0.15 ppm, phosphorus 20 ppm after A2), and FFA 0.22%, $H_2O$ content 0.52%, iron 0.1 ppm, phosphorus 15 ppm after A2');

B1) with mixer/separator according to FIG. 3: FFA 0.20%, $H_2O$ content 0.35%, iron 0.14 Ppm, phosphorus 16 ppm after A2), and FFA 0.18%, $H_2O$ content 0.28%, iron 0.1 ppm, phosphorus 12 ppm after A2').

The process step E1) was carried out with the lipid phase obtained from the process B1) with the mixer/separator system according to FIG. 1. The admixture of the aqueous solution was possible without relevant emulsion formation. The lipoid phases treated in this way could easily be separated with a conventional separator to give clear oil phases and turbid water phases.

The following values are determined in the chemical analysis:

Lipoid phase from process step A2): FFA 0.13%, $H_2O$ content 0.25%, iron content 0.1 ppm, phosphorus content 5 ppm;

Lipoid phase from process step A2'): FFA 0.12%, $H_2O$ content 0.20%, iron 0.1 ppm, phosphorus 3 ppm.

All percentages (%) made herein are by weight (wt %) unless otherwise specified in the respective specification.

Example 9: Two-Stage Methods

Example 9A: Steps B1) and E1)

130 kg of rapeseed oil (FFA content 1.40%, $H_2O$ content 0.17%, iron content 0.44 ppm, phosphorus content 65.0 ppm) are filled into the master tank (master tank 1).

Subsequently, the crude oil in the receiving tank 1 is brought to a process temperature of 45° C. and mixed with 3.9 kg of 10% sodium metasilicate solution. The mixture is then intensively stirred for 30 seconds by means of a Ystral mixer and then stirred normally for 10 minutes.

The resulting mixture is then pumped into the separation separator and the aqueous phase A is separated from the oily phase A at a capacity of 200 l/h. The aqueous phase A is collected and stored until further use. The oily phase A is transferred back into the master tank 1 for further processing. 125 ml of oily phase A were used for chemical analysis (FFA content 0.10%, $H_2O$ content 0.15%).

The oily phase A is brought to a process temperature of 40 to 45° C. and a volume of 0.6 M arginine solution is added in such a way that 1.5 moles of arginine per mole of free fatty acids are present and an introduction of air was avoided during addition. The mixture is then carefully stirred for 10 minutes. The resulting mixture is then pumped into the separation separator and the aqueous phase B is separated from the oily phase B at a capacity of 200 l/h. The aqueous phase B and the oily phase B are collected separately. 125 ml of oily phase B were used for chemical analysis (FFA content 0.1%, $H_2O$ content 0.2%).

Example 9B: Steps B1) and E1)

200 to 350 kg of rapeseed oil (FFA content 0.42%, $H_2O$ content 0.03%, iron content 0.42 ppm, phosphorus content 66.6 ppm) are filled into the master tank (master tank 1).

The crude oil is brought to a process temperature of 45 to 50° C. and a sufficient volume of 8% sodium hydrogen carbonate solution is added. The mixture is then intensively stirred for 30 seconds by means of a Ystral mixer and then stirred normally for 10 minutes. The resulting mixture is then pumped into a separation separator and the aqueous phase A is separated from the oily phase A at a capacity of 200 l/h. The aqueous phase A is collected and stored until further use. The oily phase A is transferred back into the master tank 1 for further processing. 125 ml of oily phase A were used for chemical analysis (FFA content 0.31%, $H_2O$ content 0.30%, iron content 0.15 ppm, phosphorus content 19.6 ppm).

The oily phase A is brought to a process temperature of 40 to 45° C. and a volume of 0.6 M arginine solution is added in such way that 1.5 moles of arginine per mole of free fatty acids are present and an introduction of air was avoided during addition. The mixture is then carefully stirred for 10 minutes. The resulting mixture is then pumped into the separation separator and the aqueous phase B is separated from the oily phase B at a capacity of 200 l/h. The aqueous phase B and the oily phase C are collected separately. 125 ml of oily phase B were used for chemical analysis (FFA content 0.13%, $H_2O$ content 0.41%, iron content 0.09 ppm, phosphorus content 12.8 ppm).

Example 9C: Steps B1) and E1)

200 to 350 kg of rapeseed oil (FFA content 0.42%, $H_2O$ content 0.01%, iron content 0.42 ppm, phosphorus content 67.9 ppm) are filled into the master tank (master tank 1).

The crude oil is brought to a process temperature of 45 to 50° C. and a sufficient volume of 8% strength sodium acetate solution is added. The mixture is then intensively stirred for 30 seconds by means of a Ystral mixer and then stirred normally for 10 minutes. The resulting mixture is then pumped into the separation separator and the aqueous phase A is separated from the oily phase A at a capacity of 200 l/h. The aqueous phase A is collected and stored until further use. The oily phase A is transferred back into the master tank 1 for further processing. 125 ml of oily phase A were used for chemical analysis (FFA content 0.42%, $H_2O$ content 0.55%, iron content 0.23 ppm, phosphorus content 34 ppm).

The oily phase A is brought to a process temperature of 40° C. to 45° C. and a volume of 0.6 M arginine solution is added in such a way that 1.5 moles of arginine per mole of free fatty acids are present and an introduction of air was avoided during addition. The mixture is then carefully stirred for 10 minutes. The resulting mixture is then pumped into the separation separator and the aqueous phase B is separated from the oily phase B at a power of 200 l/h. The aqueous phase B and the oily phase B are collected separately. 125 ml of oily phase B were used for chemical analysis (FFA content 0.16%, $H_2O$ content 0.45%, iron content 0.1 ppm, phosphorus content 11.8 ppm).

Example 9D: Steps B1) and E1)

200 to 350 kg of rapeseed oil (FFA content 0.43%, $H_2O$ content 0.12%, iron content 1.15 ppm, phosphorus content 57.4 ppm) are filled into the master tank (master tank 1).

The crude oil is brought to a process temperature of 45 to 50° C. and a sufficient volume of 8% strength sodium carbonate solution is added. The mixture is then intensively stirred for 30 seconds by means of a Ystral mixer and then stirred normally for 10 minutes. The resulting mixture is then pumped into the separation separator and the aqueous phase A is separated from the oily phase A at a capacity of 200 l/h. The aqueous phase A is collected and stored until further use. The oily phase A is transferred back into the master tank 1 for further processing. 125 ml of the oily phase A were used for chemical analysis (FFA content 0.26%, $H_2O$ content 0.25%, iron content 0.16 ppm, phosphorus content 18.75 Ppm).

The oily phase A is brought to a process temperature of 40 to 45° C. and a volume of 0.6 M arginine solution is added in such a way that 1.5 moles of arginine per mole of free fatty acids are present and an introduction of air was avoided during addition. The mixture is then carefully stirred for 10 minutes. The resulting mixture is then pumped into the separation separator and the aqueous phase B is separated from the oily phase B at a capacity of 200 l/h. The aqueous phase B and the oily phase B are collected separately. 125 ml of oily phase B were used for chemical analysis (FFA content 0.11%, $H_2O$ content 0.32%, iron content 0.11 ppm, phosphorus content 9.0 ppm).

The following Table 3 describes the type and appearance of the reduced lipoid phase as well as of the aqueous phase after separation by centrifugation after step B1) and before step E1) in a series of tests with rape seed oil (FFA content 0.43%, $H_2O$ content 0, 12%, iron content 1.15 ppm, phosphorus content 57.4 ppm) according to the instructions above:

| | | | Spinning test 1 min./20° C. | | | |
|---|---|---|---|---|---|---|
| | | Added | Oil phase | | | |
| Substance | conc. | volume | water-% | FFA-% | appearance | Vol % heavy phase |
| MS | 10% | 0.5% | 0.28 | 0.65 | turbid | 6 (brown) |
| | | 1.0%* | 0.12 | 0.21 | blank | 10 (brown) |
| pH = 13 | | 3.0%* | 0.07 | 0.07 | sl. turbid | 10 (nougat-brown) |
| | | 5.0% | 0.18 | 0.04 | turbid | 9 (nougat-brown) |
| NC | 10% ig | 0.5% | 0.24 | 0.56 | turbid | 7(brown) |
| | | 1.0%* | 0.14 | 0.36 | blank | 6 (brown) |
| pH = 11 | | 3.0%* | 0.16 | 0.07 | sl. turbid | 8 (light-brown) |
| | | 5.0% | 0.18 | 0.05 | turbid | 9 (light-brown) |
| NAc | 10% ig | 0.5% | 0.39 | 0.96 | turbid | 0.3 (brown) |
| | | 1.0% | 0.12 | 0.60 | blank | 13 (brown) |
| pH = 8.1 | | 3.0%* | 0.15 | 0.59 | blank | 6.5 (light-brown) |
| | | 5.0% | 0.15 | 0.59 | sl. turbid | 7.5 (light-brown) |
| NHC | 8% ig | 0.5% | 0.09 | 0.65 | alm blank | 15/thereof 0.6 water (brown) |
| | | 1.0% | 0.09 | 0.62 | alm blank | 15/thereof 0.6 water (brown) |
| pH = 8.1 | | 3.0%* | 0.11 | 0.58 | blank | 8.5/thereof 0.6 water (brown) |
| | | 5.0% | 0.11 | 0.62 | blank | 7.5/thereof 2.5 water (brown) |

MS: Na metasilicate;
NC: Na Carbonate;
NAc: sodium acetate;
NHC: Na bicarbonate
FFA: free fatty acids;
alm blank: almost blank;
sl turbid: slightly turbid

Example 10 Three-Step Procedures

Example 10A: Steps A2) and B1) and E1)

130 kg of rapeseed oil (FFA content 1.40%, $H_2O$ content 0.17%, iron content 0.44 ppm, phosphorus content 65.0 ppm) are filled into the master tank (master tank 1).

The lipoid phase in the feed tank 1 is then heated to 50 to 55° C., and 6 kg of water are then added and the mixture is intensively stirred for 30 seconds and then stirred for 10 minutes at about 100 to 150 rpm. The mixture of lipophilic phase and water is then pumped into the separation separator and the aqueous phase A is separated from the oily phase A at a capacity of 200 l/h. The aqueous phase A is collected and stored until further use. For further processing, the oily phase A is transferred into a further master tank (master tank 2). 125 ml of oily phase A were used for chemical analysis (FFA content 1.05%, $H_2O$ content 0.18%).

49 kg of the thus obtained oily phase A are brought to a process temperature of 40 to 45° C. and 1.5 kg of 10% sodium metasilicate solution is added. The mixture is then stirred intensively for 30 seconds using a Ystral mixer, free of air entry and afterwards 10 minutes stirred normally without entry of air.

The resulting mixture is then pumped into the separation separator and the aqueous phase B is separated from the oily phase B at a power of 200 l/h. The aqueous phase B is collected and used to extract the separated glycoglycerolipids. The glycoglycerolipids were recovered from aqueous phase B by extraction with chloroform. 125 ml of oily phase B were used for chemical analysis (FFA content 0.13%, $H_2O$ content 0.2%).

The oily phase B is brought to a process temperature of 40° C. to 45° C. and a volume of 0.6 M arginine solution is added in such a way that 1.5 mol of arginine per mole of free fatty acids are present and an introduction of air was avoided during addition. The mixture is then carefully stirred for 10 minutes. The resulting mixture is then pumped into the separation separator and the aqueous phase C is separated from the oily phase C at a capacity of 200 l/h. The aqueous phase C and the oily phase C are collected separately. 125 ml of the oily phase C was used for chemical analysis. The content of free fatty acids could be reduced to 0.14% by weight. In addition, the amount of potassium, phosphorus, iron and calcium was reduced to less than 5 ppm (K<5 ppm, P<5 ppm, Fe<5 ppm, Ca<5 ppm).

Example 10B: Steps A2') and B1) and E1)

Approx. 200 kg of rapeseed oil (FFA content 0.5%, $H_2O$ content 0.04%, iron content 0.63 ppm, phosphorus content 74.8 ppm) are filled into the master tank (master tank 1).

The lipoid phase is then heated to 40 to 60° C. in the receiver tank 1 and then 0.1% by weight of citric acid (33 wt %, to room temperature) is added and the mixture is intensively stirred for 30 seconds and then stirred for 10 minutes at about 100° C. at 150 rpm; 0.3% by weight of water is added then.

The mixture of lipoid phase and dilute citric acid is then pumped into the separation separator and the aqueous phase A is then separated from the oily phase A at a capacity of 200 l/h. The aqueous phase A is collected and stored until further use. For further processing, the oily phase A is transferred into a further master tank (master tank 2). 125 ml of oily phase A were used for chemical analysis (FFA content 0.48%, $H_2O$ content 0.33%, iron content 0.13 ppm, phosphorus content 15.9 ppm).

The oily phase A obtained in this way is brought to a process temperature of 40 to 45° C. and a sufficient volume of 8% sodium hydrogen carbonate solution is added so that a theoretical degree of neutralization of the free fatty acids of 90% is achieved. Subsequently, intensive mixing by means of a Ystral mixer for 30 seconds, without entry of air, and then 10 minutes normal stirring still without entry of air, that means without introduction of gas. The resulting mixture is then pumped into the separation separator and the aqueous phase B is separated from the oily phase B at a capacity of 200 l/h.

The aqueous phase B is collected. In this, sterylglycosides were detected by means of DC. The oily phase B is transferred back into the master tank 1 for further processing. 125 ml of oily phase B were used for chemical analysis (FFA content 0.39%, $H_2O$ content 0.41%, iron content 0.06 ppm, phosphorus content 4.08 ppm).

The oily phase B is brought to a process temperature of 40 to 45° C., and a volume of 0.6 M arginine solution is added in such a way that 1.5 mol of arginine per mole of free fatty acids are present and an introduction of air was avoided during addition. The mixture is then carefully stirred for 10 minutes. The resulting mixture is then pumped into the separation separator and the aqueous phase C is separated from the oily phase C at a capacity of 200 l/h. The aqueous phase C and the oily phase C are collected separately. 125 ml of the oily phase C was used for chemical analysis. The content of free fatty acids could be reduced to 0.15% by weight. In addition, the amount of potassium and calcium was reduced to less than 0.5 ppm (K<1 ppm, Ca<1 ppm) and the amount of phosphorus was reduced to 0.8 ppm and the amounts of iron were reduced to 0.02 ppm.

Example 10C: Steps A2') and B1) and E1)

Approx. 250 kg rapeseed oil (FFA content 0.42%, $H_2O$ content 0.08%, iron content 0.43 ppm, phosphorus content 70 ppm) are filled into the receiving tank (receiving tank 1).

Subsequently, the lipid phase is heated to 50 to 55° C. in the receiving tank 1 and then 0.1% by weight of citric acid (33 wt %, to room temperature) is added and the mixture is intensively stirred for 30 seconds and then stirred for 10 minutes at about 100° C. at 150 rpm; 0.3% by weight of water is added then.

The mixture of lipoid phase and dilute citric acid is then pumped into the separation separator and the aqueous phase A is then separated from the oily phase A at a capacity of 200 l/h. The aqueous phase A is collected and stored until further use. For further processing, the oily phase A is transferred into a further master tank (master tank 2). 125 ml of oily phase A were used for chemical analysis (FFA content 0.4%, $H_2O$ content 0.30%, iron content 0.13 ppm, phosphorus content 17 ppm).

The oily phase A obtained in this way is brought to a process temperature of 45 to 50° C. and a sufficient volume of 8% sodium acetate solution is added so that a theoretical degree of neutralization of the free fatty acids of 90% is achieved. Subsequently, the mixture is stirred intensively and preferably without entry of gas by means of a Ystral mixer for 30 seconds and then stirred for 10 minutes normally and preferably without entrance of gas. The resulting mixture is then pumped into the separator and the aqueous phase B is separated from the oily phase B at a capacity of 200 l/h.

Sterylglycosides were detected in the aqueous phase B by means of TLC. The oily phase B is transferred back into the master tank 1 for further processing. 125 ml of oily phase B were used for chemical analysis (FFA content 0.37%, $H_2O$ content 0.40, iron content 0.07 ppm, phosphorus content 6 ppm).

The oily phase B is brought to a process temperature of 40 to 45° C., and a volume of 0.6 M arginine solution is added in such a way that 1.5 mol of arginine per mole of free fatty acids are present and an introduction of air was avoided during addition. Subsequently, the mixture is stirred gently for 10 min. The resulting mixture is then pumped into the separation separator and the aqueous phase C is separated from the oily phase C at a capacity of 200 l/h. The aqueous phase C and the oily phase C are collected separately. 125 ml of the oily phase C was used for chemical analysis. The content of free fatty acids could be reduced to 0.12% by weight. In addition, the amount of potassium and calcium was reduced to below 5 ppm (K<5 ppm, Ca<5 ppm) and the amount of phosphorus was reduced to 1.1 ppm and the amounts of iron were reduced to 0.05 ppm.

Example 10D: Steps A2') and B1) and E1)

Approx. 300 kg rapeseed oil (FFA content 0.47%, $H_2O$ content 0.04%, iron content 0.53 ppm, phosphorus content 85.1 ppm) are filled into the master tank (master tank 1).

Subsequently, the lipoid phase is heated to about 70° C. in the receiver tank 1 and then 0.1% by weight of citric acid (33%, to room temperature) is added and the mixture is intensively stirred for 30 seconds and then 10 minutes at about 100 to 150 rpm; 0.3% by weight of water is added then.

The mixture of lipid phase and dilute citric acid is then pumped into the separation separator and the aqueous phase A is then separated from the oily phase A at a capacity of 200 l/h. The aqueous phase A is collected and stored until further use. For further processing, the oily phase A is transferred into a further master tank (master tank 2). 125 ml of oily phase A were used for chemical analysis (FFA content 0.46%, $H_2O$ content 0.53%, iron content 0.13 ppm, phosphorus content 16.2 ppm).

The oily phase A obtained in this way is brought to a process temperature of 40 to 45° C. and a sufficient volume of 8% sodium carbonate solution is added so that a theoretical neutralization degree of the free fatty acids of 90% is achieved. The mixture is then stirred intensively and preferably without gassing by means of a Ystral mixer for 30 seconds and then stirred normally for 10 minutes, preferably without entry of air. The resulting mixture is then pumped into the separation separator and the aqueous phase B is separated from the oily phase B at a capacity of 200 l/h. The aqueous phase B is collected and used to extract the separated glycoglycerolipids. The glycoglycerolipids were recovered from aqueous phase B by extraction with chloroform. The oily phase B is transferred back into the master tank 1 for further processing. 125 ml of oily phase B were used for chemical analysis (FFA content 0.24%, $H_2O$ content 0.48%, iron content 0.03 ppm, phosphorus content 2.25 ppm).

The oily phase B is brought to a process temperature of 40 to 45° C., and a volume of 0.6 M arginine solution is added in such a way that 1.5 mol of arginine per mole of free fatty acids are present and an introduction of air was avoided during addition. Subsequently, the mixture is stirred gently for 10 minutes and free of air introduction. The resulting mixture is then pumped into the separation separator free of air and thus the aqueous phase C is separated from the oily phase C at a capacity of 200 l/h. The aqueous phase C and the oily phase C are collected separately. 125 ml of the oily phase C was used for chemical analysis. The content of free fatty acids could be reduced to 0.10% by weight. In addition, the amount of potassium and calcium was reduced to below 0.4 ppm (K<0.4 ppm, Ca<0.5 ppm), and the amount of phosphorus was reduced to 0.8 ppm and the amounts of iron to 0.02 ppm.

Example 10E

According to Example 10D), rapeseed oil was examined as a lipoid phase. The data are given in mg per kg lipoid phase except for FFA. For FFA, the data are in % by weight. "Raw" denotes the initial values of the lipid phase. A2 ') mean the values after step A2'). B1) are the values after step B1). E1) are the values after step E1).

|  | raw | A2') | B1) | E1) |
|---|---|---|---|---|
| FFA [%] | 0.58 | 0.55 | 0.28 | 0.18 |
| P [mg/kg] | 96.18 | 10.04 | 1.20 | 0.712 |
| Fe [mg/kg] | 0.64 | 0.15 | 0.032 | 0.012 |
| Ca [mg/kg] | 48.71 | 2.74 | 0.506 | 0.473 |
| Mg [mg/kg] | 8.62 | 0.56 | 0.131 | 0.109 |
| Cr [mg/kg] | 0.016 | 0.009 | 0.009 | 0.007 |
| Zn [mg/kg] | 0.167 | 0.027 | 0.015 | 0.007 |
| Mn [mg/kg] | 0.136 | 0.015 | 0.004 | 0.001 |

| Sample name | $H_2O$ | FFA % | P mg/kg | Fe mg/kg | Ca mg/kg | Mg mg/kg |
|---|---|---|---|---|---|---|
| Crude - NC | 0.05 | 0.54 | 78.32 | 0.53 | 33.04 | 5.70 |
| NC-Degumming = A2' | 0.53 | 0.48 | 16.57 | 0.15 | 1.78 | 0.28 |
| NC Lipoids = B1) | 0.49 | 0.25 | 2.21 | 0.15 | 0.32 | 0.07 |
| NC Native neutral = E1) | 0.59 | 0.23 | 0.90 | 0.04 | 0.34 | 0.09 |

Example 10F

According to Example 10C), rapeseed oil was examined as a lipoid phase. The data are given in mg per kg lipoid phase except for FFA. For FFA, the data are in % by weight. "Raw" denotes the initial values of the lipid phase. A2') mean the values after step A2'). B1) are the values after step B1). E1) are the values after step E1).

|  | raw | A2') | B1) | E1) |
|---|---|---|---|---|
| Mg [mg/kg] | 8.62 | 0.511 | 0.125 | 0.093 |
| Cr [mg/kg] | 0.016 | 0.007 | 0.009 | 0.006 |
| Mn [mg/kg] | 0.136 | 0.016 | 0.004 | 0.002 |

| Sample name | $H_2O$ | FFA % | P mg/kg | Fe mg/kg | Ca mg/kg | Mg mg/kg |
|---|---|---|---|---|---|---|
| Crude-NAc-means | 0.05 | 0.43 | 52.52 | 0.60 | 31.33 | 5.43 |
| NAc-Degumming = A2' | 0.26 | 0.43 | 12.49 | 0.17 | 1.85 | 0.40 |
| NAc-Lipoids = B1 | 0.24 | 0.44 | 5.79 | 0.09 | 0.89 | 0.25 |
| NAc-Native neutral = E1 | 0.37 | 0.13 | 0.80 | 0.00 | 0.21 | 0.07 |

What is claimed is:

1. A method for the hydrolysis-poor separation of glycoglycerolipids from a lipid phase which contains glycoglycerolipids and acylglycerides, comprising the steps:
   A1) providing a lipid phase containing glycoglycerolipids and acylglycerides,
   B1) adding to the lipid phase an aqueous phase containing anions of at least one salt which has a solubility of at least 30 g/l in water at 20° C. and which, upon dissociation in water, forms carbonate ($CO_3^{2-}$), bicarbonate ($HCO_3^-$), metasilicate ($SiO_3^{2-}$), orthosilicate ($SiO_4^{4-}$), disilicate ($Si_2O_5^{2-}$), trisilicate ($Si_3O_7^{2-}$), acetate ($CH_3COO^-$), borate ($BO_3^{3-}$), and/or tartrate ($C_4H_4O_6^{2-}$);
   C1) mixing the lipid phase and the aqueous phase;
   D1) separating the glycoglycerolipid-rich aqueous phase and obtaining a glycoglycerolipid-poor lipid phase; and
   D2) recovering the glycoglycerolipids from the separated glycoglycerolipid-rich aqueous phase.

2. The method according to claim 1, comprising the following step E1) after step D1):
   E1) adding second aqueous phase containing at least one compound which has at least one amidino group and/or at least one guanidino group to the glycoglycerolipid-poor lipid phase, followed by mixing the glycoglycerolipid-poor lipid phase and the second aqueous phase and separating the second aqueous phase.

3. The method according to claim 1, wherein the glycoglycerolipids are lipophilic glycoglycerolipids having a lipophilicity index GL of $1.0 \leq GL \leq 6.0$, wherein the lipophilicity index GL is calculated according to the following formula:

$$GL = \frac{\text{Sum of the carbon atoms of the acyl residues}}{\text{Sum of hydroxy and amino groups}}.$$

4. The method according to claim 1, wherein the glycoglycerolipids are glycosyldiacylglycerols, glycosylylalkylglycerols, and glycosyldialkylglycerols.

5. The method according to claim 1, wherein the glycoglycerolipid-rich aqueous phase do not contain any carboxylate, sulfate, sultanate, or phosphate group(s).

6. The method according to claim 1, wherein the lipid phase in step A1) further comprises sterylglycosides which are separated in the aqueous phase in step D1).

7. The method according to claim 1, wherein in step B1) an aqueous phase which contains cations of a salt which has a solubility of at least 30 g/l in water at 20° C. and which, upon dissociation in water, forms $Mg^{2+}$, $Ca^{2+}$, $Ti^{2+}$, $Ti^{4+}$, $Co^{2+}$, $Co^{3+}$, $Ni^{2+}$, $Cu^{2+}$, $Zn^{2+}$, $Sn^{2+}$, or $Sn^{4+}$ ions is added to the lipid phase.

8. The method according to claim 1, wherein if phospholipids and/or fatty acids are contained in the lipid phase, a phospholipid-free and/or fatty acid-free glycoglycerolipid-rich phase is obtained if the following step A2 or A2') is carried out after step A1) and before step B1):
   A2) adding water phase as aqueous phase to the lipoid, followed by mixing the lipoid phase and the aqueous phase and separating the aqueous phase, or
   A2') adding an aqueous carboxylic acid solution or an aqueous solution of an inorganic acid having a pH between 3.0 and 5.0 as aqueous phase to the lipoid phase, followed by mixing the lipoid phase and the aqueous phase and separating the aqueous phase.

9. The method according to claim 8, wherein the lipoid phase and the aqueous phase are intensively mixed in step C1) and/or A2) or A2').

10. The method according to claim 1, comprising the following step E1) after step D2):
    E1) adding an aqueous phase containing at least one compound which has at least one amidino group and/or at least one guanidino group to the lipid glycoglycerolipid-poor phase, followed by mixing the lipid glycoglycerolipid-poor phase and the aqueous phase and separating the aqueous phase.

11. A method for recovering hydrolysis-poor glycoglycerolipids and glycosphingolipids from a lipid phase which contains glycoglycerolipids, glycosphingolipids, and acylglycerides, comprising the steps of:
    A1) providing a lipid phase containing glycoglycerolipids, glycosphingolipids, and acylglycerides;
    B1) adding to the lipid phase an aqueous phase containing anions of at least one salt which has a solubility of at least 30 g/l in water at 20° C. and which upon dissociation in water, forms carbonate ($CO_3^{2-}$), bicarbonate ($HCO_3^-$), metasilicate ($SiO_3^{2-}$), orthosilicate ($SiO_4^{4-}$), disilicate ($Si_2O_5^{2-}$), trisilicate ($Si_3O_7^{2-}$), acetate ($CH_3COO^-$), borate ($BO_3^{3-}$), Or tartrate ($C_4H_4O_6^{2-}$);
    C1) mixing the lipid phase and the aqueous phase;
    D1) separating the glycoglycerolipid-rich and/or glycosphingolipid-rich aqueous phase and obtaining a glycoglycerolipid-poor and/or glycosphingolipid-poor lipid phase; and
    D2) recovering the glycoglycerolipids from the separated glycoglycerolipid-rich aqueous phase.

12. The method according to claim 11, wherein the glycosphingolipids are lipophilic glycosphingolipids having a lipophilicity index SL of 1.0≤SL≤7.0, wherein the lipophilicity index SL is calculated according to the following formula:

$$SL = \frac{\text{Sum of carbon atoms of the ceramide residue}}{\text{Sum of hydroxy and amino and amido groups}}.$$

13. The method according to claim 11, wherein the glycoglycerolipids do not contain any carboxylate, sulfate, sulfonate, or phosphate group(s).

14. A method according to claim 11, wherein the lipoid phase in step
   A1) further comprises sterylglycosides which are separated in the aqueous phase in step D1).

15. The method according to claim 11, wherein in step Bib) an aqueous phase which contains cations of a salt which has a solubility of at least 30 g/l in water at 20° C. and which, upon dissociation in water, forms $Mg^{2+}$, $Ca^{2+}$, $Ti^{2+}$, $Ti^{4+}$, $Co^{2+}$, $Co^{3+}$, $Ni^{2+}$, $Cu^{2+}$, $Zn^{2+}$, $Sn^{2+}$, or $Sn^{4+}$ ions is added to the lipoid phase.

* * * * *